US012630607B2

(12) United States Patent
Weis et al.

(10) Patent No.: US 12,630,607 B2
(45) Date of Patent: May 19, 2026

(54) PRAME TCR RECEPTORS AND USES THEREOF

(71) Applicant: BioNTech SE, Mainz (DE)

(72) Inventors: Manon Weis, Sankt Wolfgang (DE); Patrik Kehler, Planegg (DE); Maria Gerget, Munich (DE); Christian Krendl, Graefelfing (DE); Susanne Wilde, Germering (DE)

(73) Assignee: BioNTech SE, Mainz (DE)

( * ) Notice: Subject to any disclaimer, the term of this patent is extended or adjusted under 35 U.S.C. 154(b) by 1037 days.

(21) Appl. No.: 17/777,977

(22) PCT Filed: Nov. 18, 2020

(86) PCT No.: PCT/EP2020/082488

§ 371 (c)(1),
(2) Date: May 18, 2022

(87) PCT Pub. No.: WO2021/099360

PCT Pub. Date: May 27, 2021

(65) Prior Publication Data

US 2022/0401484 A1     Dec. 22, 2022

(30) Foreign Application Priority Data

Nov. 18, 2019     (EP) ..................................... 19209757

(51) Int. Cl.
C07K 14/705          (2006.01)
A61K 38/00           (2006.01)
(Continued)

(52) U.S. Cl.
CPC .... *C07K 14/70596* (2013.01); *A61K 38/1774* (2013.01); *A61K 39/3955* (2013.01);
(Continued)

(58) Field of Classification Search
None
See application file for complete search history.

(56) References Cited

U.S. PATENT DOCUMENTS

2018/0282808 A1*  10/2018  Milla ................. A61K 40/4243

FOREIGN PATENT DOCUMENTS

CN        106699874         5/2017
JP        2008263950 A  *  11/2008
              (Continued)

OTHER PUBLICATIONS

Wong, et al., Comparative analysis of the CDR loops of antigen receptors. Frontiers in Immunology (Oct. 2019), 10:2454, p. 1-11.*

(Continued)

*Primary Examiner* — Joanne Hama
*Assistant Examiner* — Jami Michelle Gurley
(74) *Attorney, Agent, or Firm* — Armstrong Teasdale LLP

(57)          ABSTRACT

The present invention relates to a T cell receptor (TCR) capable of binding to a PRAME peptide having the amino acid sequence SLLQHLIGL (SEQ ID NO: 1) or a portion thereof, or its HLA-A2 bound form. Also encompassed in the present invention is a nucleic acid encoding a TCR, a vector comprising the nucleic acid, and a host cell comprising the TCR, the nucleic acid sequence, or the vector. Comprised is further, a method for obtaining a TCR described herein, a pharmaceutical or diagnostic composition, and a method of detecting the presence of a cancer in a subject in vitro. Furthermore, the present invention relates to the use of a TCR, a nucleic acid and/or a vector for generating modified lymphocytes.

17 Claims, 29 Drawing Sheets

Specification includes a Sequence Listing.

(51) Int. Cl.

| | |
|---|---|
| *A61K 38/17* | (2006.01) |
| *A61K 39/395* | (2006.01) |
| *A61K 40/11* | (2025.01) |
| *A61K 40/32* | (2025.01) |
| *A61K 40/42* | (2025.01) |
| *A61P 35/00* | (2006.01) |
| *C07K 14/54* | (2006.01) |
| *C07K 14/55* | (2006.01) |
| *C07K 14/725* | (2006.01) |
| *C07K 16/28* | (2006.01) |
| *G01N 33/50* | (2006.01) |
| *G01N 33/574* | (2006.01) |
| *G01N 33/575* | (2026.01) |

(52) U.S. Cl.

CPC .............. *A61K 40/11* (2025.01); *A61K 40/32* (2025.01); *A61K 40/427* (2025.01); *A61P 35/00* (2018.01); *C07K 14/5443* (2013.01); *C07K 14/55* (2013.01); *C07K 14/7051* (2013.01); *C07K 14/70521* (2013.01); *C07K 16/2803* (2013.01); *C07K 16/2809* (2013.01); *C07K 16/2818* (2013.01); *C07K 16/2896* (2013.01); *G01N 33/5091* (2013.01); *G01N 33/5759* (2026.01); *A61K 38/00* (2013.01); *C07K 2317/622* (2013.01); *C07K 2319/30* (2013.01)

(56) References Cited

FOREIGN PATENT DOCUMENTS

| | | |
|---|---|---|
| WO | 2016142783 | 9/2016 |
| WO | 2017216324 | 12/2017 |
| WO | 2018234319 | 12/2018 |
| WO | 2019036688 | 2/2019 |
| WO | 2019133853 | 7/2019 |

OTHER PUBLICATIONS

Garcia and Adams. How the T cell receptor sees antigen - A structural view. Cell (2005), 122, p. 333-336.*

Goyarts, et al. Point mutations in the β chain CDR3 can alter the T cell receptor recognition pattern on an MHE class I/peptide complex over a broad interface area. Mol. Immunology (1998), 35:10, p. 593-607.*

Xue et al., "Exploiting T cell receptor genes for cancer immunotherapy", Clin Exp Immunol, 2005, 139(2), pp. 167-172.

Schmitt et al., "T cell receptor gene therapy for cancer", Hum Gene Ther, 2009, 20(11), pp. 1240-1248.

Misurin, "Prognostic significance of prame gene expression in solid tumors", Immunologiya, 2018, 39(1), pp. 67-73.

Rudikoff et al., "Single amino acid substation altering antigenbinding specificity", Immunology, 1982, 78, pp. 1979-1983.

Kussie et al., "A single engineered amino acid substitution changes antibody fine specificity", J Immunol, 1994, 152 (1), pp. 146-152.

Nakauchi et al., "Characterization of Monoclonal Antibodies to Junin Virus Nucleocapsid Protein and Application to the Diagnosis of Hemorrhagic Fever Caused by South American Arenaviruses", Clinical and Vaccine Immunology, 2009, 16(80, pp. 1132-1138.

Belin et al., "Toxicity-based selection of Escherichia coli mutants for functional recombinant protein production: application to an antibody fragment", Protein Engineering Design and Selection, 2004, 17(5), pp. 491-500.

Schmidt, "Fusion-proteins as biopharmaceuticals—applications and challenges", Current opinion in drug discovery & development, 2009, 12(2), pp. 284-295.

Gezgin et al., "PRAME as a Potential Target for Immunotherapy in Metastatic Uveal Melanoma", JAMA Ophthalmology, 2017, 135(6), pp. 541-549.

Yamaguchi et al., "Different Response to Nivolumab in a Patient with Synchronous Double Primary Carcinomas of Hypopharyngeal Cancer and Non-Small-Cell Lung Cancer", Case Rep Oncol, 2018, 10(3), pp. 802-808.

* cited by examiner

Figure 5 (cont.)

MelA375
(PRAME-pos)

027-004
3825
UT

Cell count (1/mm²)

time in hours

**SKMel23
(PRAME-pos)**

Figure 7

| Allele | Frequency [decimals] |
|---|---|
| HLA-A*02:01 | 0,27600 |
| HLA-A*02:05 | 0,00966 |
| HLA-A*02:06 | 0,00182 |
| HLA-A*02:02 | 0,00087 |
| HLA-A*02:17 | 0,00035 |

| Allele | Frequency [decimals] |
|---|---|
| HLA-A*02:07 | 0,00004 |
| HLA-A*02:04 | 0,00001 |
| HLA-A*02:08 | 0,00001 |
| HLA-A*02:10 | n.a. |
| HLA-A*02:16 | n.a. |

Figure 10

| TCR | HLA recognition | | |
|---|---|---|---|
| 027-004 | 02:01 | 02:02 | 02:04 |
| 3825 | 02:01 | | |

NCI-H1650

PRAME TCR RECEPTORS AND USES THEREOF

FIELD OF THE INVENTION

The present invention relates to a T cell receptor (TCR) capable of binding to a PRAME peptide having the amino acid sequence SLLQHLIGL (SEQ ID NO: 1) or a portion thereof, or its HLA-A2 bound form. Also encompassed in the present invention is a nucleic acid encoding a TCR, a vector comprising the nucleic acid, and a host cell comprising the TCR, the nucleic acid sequence, or the vector. Comprised is further, a method for obtaining a TCR described herein, a pharmaceutical or diagnostic composition, and a method of detecting the presence of a cancer in a subject in vitro. Furthermore, the present invention relates to the use of a TCR, a nucleic acid and/or a vector for generating modified lymphocytes.

BACKGROUND OF THE INVENTION

T lymphocytes (or T cells) which form a part of the cell mediated immune system play a major role in the eradication of pathogens. T cells develop in the thymus and express T cell receptor molecules on their surface that allow the recognition of peptides presented on major histocompatibility complex (MHC) molecules which are expressed on nucleated cells (antigen presentation). Antigens of pathogens, i.e. foreign antigens presented by MHC molecules will elicit a powerful T cell response whereas self-antigens usually do not lead to a T cell response due to a negative selection of self-antigen specific T cells in the thymus during the development of such T cells. The immune system can thus discriminate between nucleated cells presenting foreign-or self-antigens and specifically target and eradicate infected cells via potent cytokine release and cellular cytotoxicity mechanisms of the T cells.

The power of the immune system has been recognized as a promising tool for future cancer therapies. In the last decade, research has begun to exploit the unique properties of T cells by using adoptive cell transfer (ACT), which involves the administration of donor-derived lymphocytes, expanded ex vivo. ACT is an attractive concept for the treatment of cancer because it does not require immune-competence of patients, and the specificity of transferred lymphocytes can be targeted against non-mutated and thus poorly immunogenic tumor antigens that typically fail to effectively trigger autologous T cell responses. Although ACT has been shown to be a promising treatment for various types of cancer, its broad application as clinical treatment has been hampered by the need for custom isolation and characterization of tumor-specific T cells from each patient—a process that can be difficult and time-consuming but also often fails to yield high-avidity T cells (Xue et al., Clin Exp Immunol. 2005 February; 139 (2): 167-172; Schmitt et al., Hum Gene Ther. 2009 November; 20 (11): 1240-1248).

The genetic transfer of tumor antigen-specific T cell receptors (TCRs) into primary T cells can overcome some of the current limitations of ACT, as it allows for the rapid generation of tumor-reactive T lymphocytes with defined antigen specificity even in immunocompromised patients. However, the identification of suitable T cell clones bearing TCRs that specifically recognize tumor antigens and exhibit the desired anti-tumor effects in vivo is still the topic of ongoing research. Considering that in 2012 about 14.1 million new cases of cancer occurred globally and that cancer currently is the cause of about 14.6% of all human deaths worldwide, novel and efficient treatment options are urgently needed. It is the object of the present invention to comply with the needs set out above.

PRAME is a tumor-associated antigen expressed in a wide variety of tumors, preferably melanoma. Further, PRAME has been described as an independent biomarker for metastasis, such as uveal melanoma (Fiedl et al., Clin Cancer Res 2016 March; 22 (5): 1234-1242) and as a prognostic marker for DLBCL (Mitsuhashi et al., Hematology 2014, January 2014). It is not expressed in normal tissues, except testis. This expression pattern is similar to that of other cancer testis (CT) antigens, such as MAGE, BAGE and GAGE. However, unlike these other CT antigens, this gene is also expressed in acute leukemia. The encoded protein acts as a repressor of retinoic acid receptor, and likely confers a growth advantage to cancer cells via this function. Alternative splicing results in multiple transcript variants. PRAME overexpression in triple negative breast cancer has also been found to promote cancer cell motility through induction of the epithelial-to-mesenchymal transition (Al-Khadairi et al., Journal of Translational Medicine 2019; 17:9). Deletion of PRAME has been reported in chronic lymphocytic leukemia, however, this is not functionally relevant since the gene is not expressed in B cells, and the deletion is a consequence of a physiological immunoglobulin light chain rearrangement.

SUMMARY OF THE INVENTION

The present invention refers to a novel T cell receptor (TCR) capable of specifically recognizing the tumor-associated antigen PRAME. In particular, the identified TCR specifically recognizes PRAME amino acid sequence SLLQHLIGL, also referred to as $PRAME_{SLL}$ peptide herein. The invention is based at least partly on the surprising finding that said isolated T cell receptors binding against the specific PRAME peptide have outstanding properties when compared to PRAME TCRs known in the prior art. Specifically, the T cell receptor of the present invention capable of binding to PRAME peptide SLLQHLIGL also provides high functional avidity and advantageous tumor cell recognition and killing properties. Contrary thereto, normal cells, and irrelevant peptides are not recognized by said TCR. Furthermore, the T cell receptor recognizes the peptide as presented on HLA molecules (Human Leukocyte Antigen, HLA), and especially on HLA molecules coded by the HLA sub-alleles HLA-A*02:01, HLA-A*02:02, and HLA-A*02:04, allowing even for the treatment of cancer patients expressing less frequent HLA-A*02 alleles that present $PRAME_{SLL}$.

In a first aspect, the present invention relates to a T cell receptor (TCR) capable of binding to a PRAME peptide having the amino acid sequence SLLQHLIGL (SEQ ID NO: 1) or a portion thereof, or its HLA-A2 bound form, wherein the TCR comprises: a CDR3 of the TCR alpha chain variable region comprising or consisting of the amino acid sequence of (SEQ ID NO: 6), or an amino acid sequence having at least 80% identity to SEQ ID NO: 6, preferably at least 85% identity, more preferably 90% or 95% identity, and/or a CDR3 of the TCR beta chain variable region comprising or consisting of the amino acid sequence of (SEQ ID NO: 7), or an amino acid sequence having at least 80% identity to SEQ ID NO: 7, preferably at least 85% identity, more preferably 90% or 95% identity.

In another aspect, the present invention relates to a T cell receptor (TCR) capable of binding to a PRAME peptide having the amino acid sequence SLLQHLIGL (SEQ ID NO: 1) or a portion thereof, or its HLA-A2 bound form, wherein the TCR comprises:

a) a CDR3 of the TCR alpha chain variable region comprising or consisting of the amino acid sequence of (SEQ ID NO: 6), or an amino acid sequence having at least 80% identity to SEQ ID NO: 6, preferably at least 85% identity, more preferably 90% or 95% identity, a CDR1 of the TCR alpha chain variable region comprising or consisting of the amino acid sequence of SEQ ID NO: 2, and a CDR2 of the TCR alpha chain variable region comprising or consisting of the amino acid sequence of SEQ ID NO: 4, and b) a CDR3 of the TCR beta chain variable region comprising or consisting of the amino acid sequence of (SEQ ID NO: 7), or an amino acid sequence having at least 80% identity to SEQ ID NO: 7, preferably at least 85% identity, more preferably 90% or 95% identity, a CDR1 of the TCR beta chain variable region comprising or consisting of the amino acid sequence of SEQ ID NO: 3, and a CDR2 of the TCR beta chain region comprising or consisting of the amino acid sequence of SEQ ID NO: 5.

It is envisaged that the HLA-A2 is a HLA-A*02:01, HLA-A*02:02 or HLA-A*02:04 encoded molecule.

In particular, it is envisaged that binding of the TCR to sequence SLLQHLIGL (SEQ ID NO: 1) or a preferably functional portion thereof, or its HLA-A2 bound form induces IFN-gamma secretion by cells transduced or transfected with the TCR.

Preferably, the half-maximal relative IFN-gamma secretion ($EC_{50}$ value) is less than 10-7 M, as measured by an IFN-gamma immunoassay.

It is also envisaged that the TCR of the present invention comprises:

a) a TCR alpha chain comprising a CDR1 having the amino acid sequence of SEQ ID NO: 2, a CDR2 having the amino acid sequence of SEQ ID NO: 4 and a CDR3 having the amino acid sequence of SEQ ID NO: 6, and/or b) a TCR beta chain comprising a CDR1 having the amino acid sequence of SEQ ID NO: 3, a CDR2 having the amino acid sequence of SEQ ID NO: 5 and a CDR3 having the amino acid sequence of SEQ ID NO: 7.

In view of the present invention, the TCR referred to herein may comprise a TCR alpha chain variable region comprising or consisting of the amino acid sequence of SEQ ID NO: 8, and/or a TCR beta chain variable region comprising or consisting of the amino acid sequence of SEQ ID NO: 9.

It is also envisaged that the TCR of the present invention comprises a TCR alpha chain constant region and/or a TCR beta chain constant region.

Preferably, the TCR of the present invention comprises a) a TCR alpha chain comprising or consisting of an amino acid sequence selected from SEQ ID NO: 10; or an amino acid sequence having at least 80% identity, preferably at least 85% identity, more preferably 90% or 95% to SEQ ID NO: 10; and/or b) a TCR beta chain comprising or consisting of an amino acid sequence selected from of SEQ ID NO: 11, or an amino acid sequence having at least 80% identity, preferably at least 85% identity, more preferably 90% or 95% to SEQ ID NO: 11.

It is also envisaged that the TCR of the present invention comprises at least one TCR alpha chain(s) and at least one TCR beta chain(s) covalently linked to each other to form TCR heterodimers or multimers.

In view of the present invention, it is envisaged that the TCR referred to herein may be selected from a native TCR, a TCR variant, a TCR fragment, or a TCR construct.

In some embodiments, the TCR of the present invention comprises one or more fusion component(s) optionally selected from Fc receptors; Fc domains, including IgA, IgD, IgG, IgE, and IgM; cytokines, including IL-2 or IL-15; toxins; antibodies or antigen-binding fragments thereof, including anti-CD3, anti-CD28, anti-CD5, anti-CD16 or anti-CD56 antibodies or antigen-binding fragments thereof; CD247 (CD3-zeta), CD28, CD137 or CD134 domains, or combinations thereof, optionally further comprising at least one linker.

The TCR referred to herein, preferably comprises at least one TCR alpha chain as defined herein; and/or at least one TCR beta chain as defined herein; and/or an antibody or a single chain antibody fragment (scFv) which is directed against an antigen or epitope on the surface of lymphocytes, wherein the TCR alpha chain(s) and TCR beta chain(s) are linked to each other and fused, optionally via a linker, to said antibody or scFv. Said antigen may be selected from CD3, CD28, CD5, CD16 or CD56.

The TCR of the present invention preferably comprises at least one molecular marker. Preferably, the TCR of the present invention is soluble.

In another aspect, the present invention relates to a nucleic acid encoding the TCR referred to herein.

Said nucleic acid may comprise the nucleic acid sequence of SEQ ID NOs: 13, 14, 15, 16, 17, 18, 19, 20, 21, or 22.

In another aspect, the present invention relates to a vector comprising the nucleic acid defined herein.

In another aspect, the present invention relates to a host cell comprising the TCR defined herein, the nucleic acid sequence defined herein or the vector defined herein. The host cell may be selected from lymphocytes including but not limited to cytotoxic T lymphocytes (CTLs), CD8+ T cells, CD4+ T cells, natural killer (NK) cells, natural killer T (NKT) cells, gamma/delta-T cells.

In another aspect, the present invention relates to a method for obtaining the TCR defined herein, wherein the method comprises incubating the host cell defined herein under conditions causing expression of said TCR, and purifying said TCR.

In another aspect, the present invention relates to a pharmaceutical or diagnostic composition comprising one or more of: the TCR defined herein; the nucleic acid defined herein; the vector defined herein; and/or the host cell defined herein, and, optionally, pharmaceutical excipient(s). The pharmaceutical composition may further comprise a checkpoint inhibitor. Said checkpoint inhibitor may be selected from the group consisting of a CTLA-4 inhibitor, a PD-1 inhibitor and a PD-L1 inhibitor, LAG3, ICOS, TIM3, VISTA and CEACAM1 inhibitors.

In another aspect, the present invention refers to the TCR defined herein, the nucleic acid defined herein, the vector defined herein and/or the host cell defined herein for use as a medicament. Preferably the use is in detection, diagnosis, prognosis, prevention and/or treatment of cancer. In this respect it is envisaged that the cancer is selected from the group consisting of melanoma, bladder carcinoma, colon carcinoma, and breast adenocarcinoma, sarcoma, prostate cancer, uterine cancer, uveal cancer, uveal melanoma, squamous head and neck cancer, synovial carcinoma, Ewing's sarcoma, triple negative breast cancer, thyroid cancer, testicular cancer, renal cancer, pancreatic cancer, ovarian cancer, esophageal cancer, non-small-cell lung cancer, non-Hodgkin's lymphoma, multiple myeloma, melanoma, hepatocellular carcinoma, head and neck cancer, gastric cancer, endometrial cancer, colorectal cancer, cholangiocarcinoma, breast cancer, bladder cancer, myeloid leukemia and acute lymphoblastic leukemia, preferably wherein the cancer is selected from the group consisting of NSCLC, SCLC, breast, ovarian or colorectal cancer, sarcoma or osteosarcoma.

Further, it is envisaged that the use of the TCR, the nucleic acid, the vector and/or the host cell as defined herein in the prevention and/or treatment of cancer comprises:

(a) providing one or more of (i) the TCR described somewhere else herein; (ii) the nucleic acid described somewhere else herein; (iii) the vector described somewhere else herein; (iv) the host cell described somewhere else herein; and (v) the pharmaceutical composition described somewhere else herein; and (b) administering at least one of (i) to (v) to a subject in need thereof.

Preferably, the TCR, nucleic acid, vector and/or host cell as defined herein for the use in prevention and/or treatment of cancer comprise:

(a) providing a sample of a subject, said sample comprising lymphocytes;

(b) providing one or more of (i) the TCR described somewhere else herein; (ii) the nucleic acid described somewhere else herein; (iii) the vector described somewhere else herein; (iv) the host cell described somewhere else herein; and (v) the pharmaceutical composition described somewhere else herein;

(c) introducing of one or more of (i) to (v) of step (b) into the lymphocytes of step (b) and, thereby, obtaining modified lymphocytes, (d) administering the modified lymphocytes of step (c) to a subject or patient in need thereof.

In another aspect, the present invention relates to a method of detecting the presence of a cancer in a subject in vitro, comprising:

(a) providing a sample of a subject, said sample comprising one or more cells;

(b) contacting said sample with (i) the TCR described somewhere else herein; (ii) the host cell described somewhere else herein; and/or (iii) the pharmaceutical composition described somewhere else herein; thereby forming a complex, and (c) detecting the complex, wherein detection of the complex is indicative of the presence of the cancer in the subject.

In still another aspect, the present invention relates to the use of a TCR defined herein, a nucleic acid defined herein and/or a vector defined herein for generating modified lymphocytes.

BRIEF DESCRIPTION OF THE FIGURES

FIG. 7: HLA-A*02 allele frequency. The allele frequency of US/European Caucasian populations (www.allelefrequencies.net).

The control TCR 3825 efficiently recognizes the PRAME peptide presented by 1 of 10 tested HLA-A2 sub-alleles (A*02:2), i.e. only the HLA-A2 sub-allele A*02:01 is recognized.

FIG. 10: Summary of the results shown in FIGS. 8 and 9.

Figure 11:
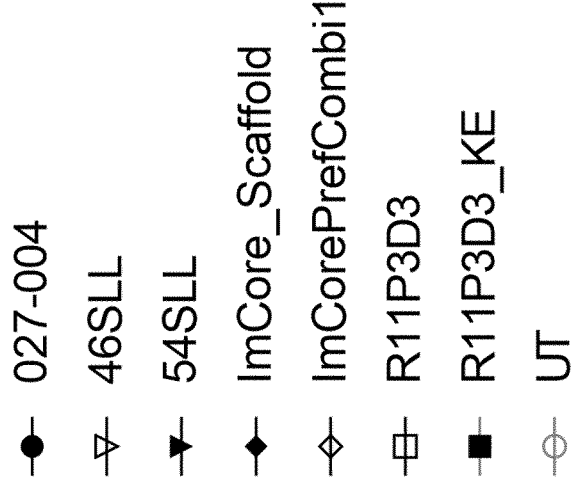
Figure 11:
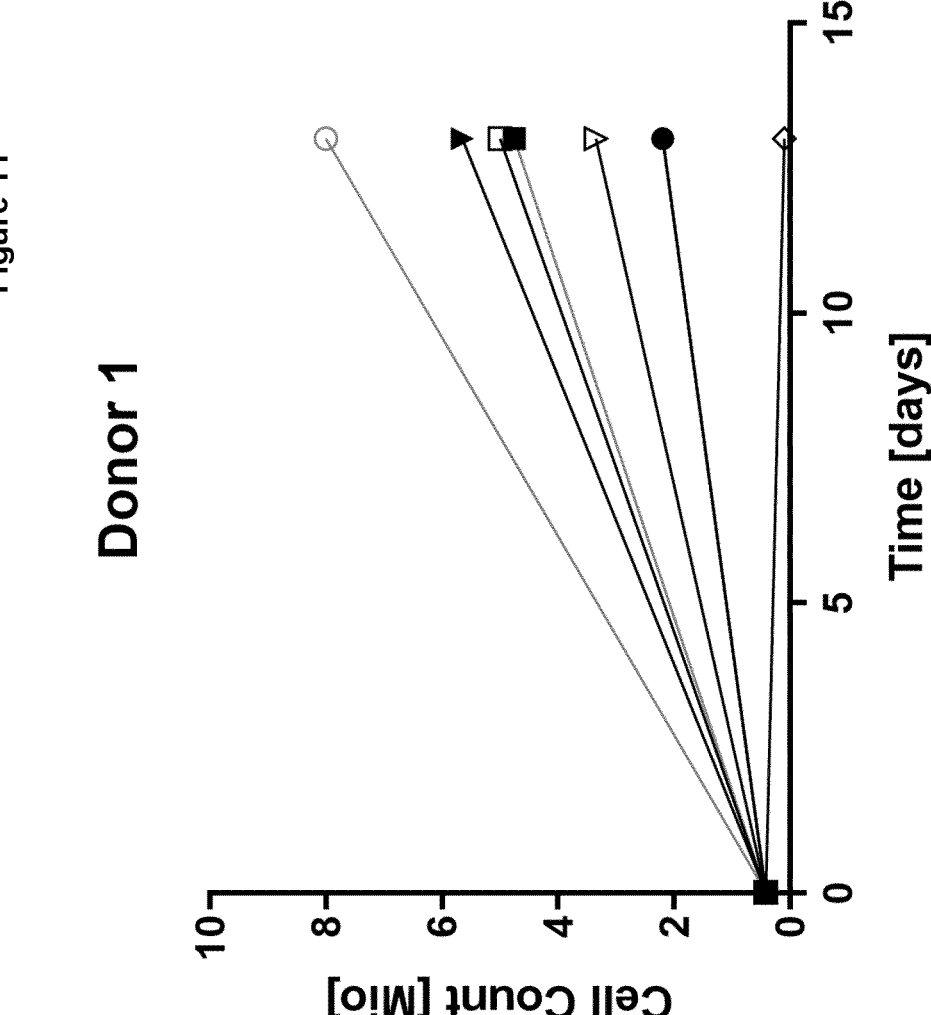
Figure 11:
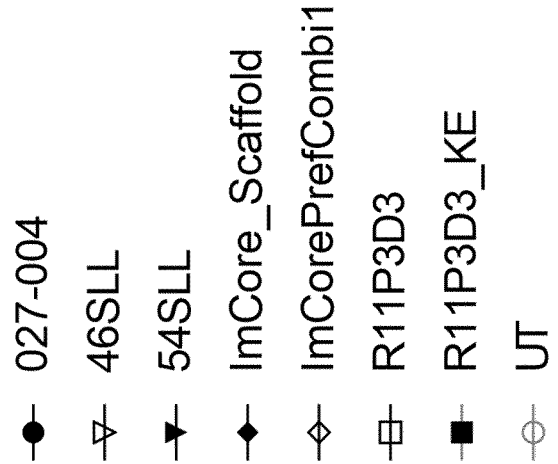
Figure 11:
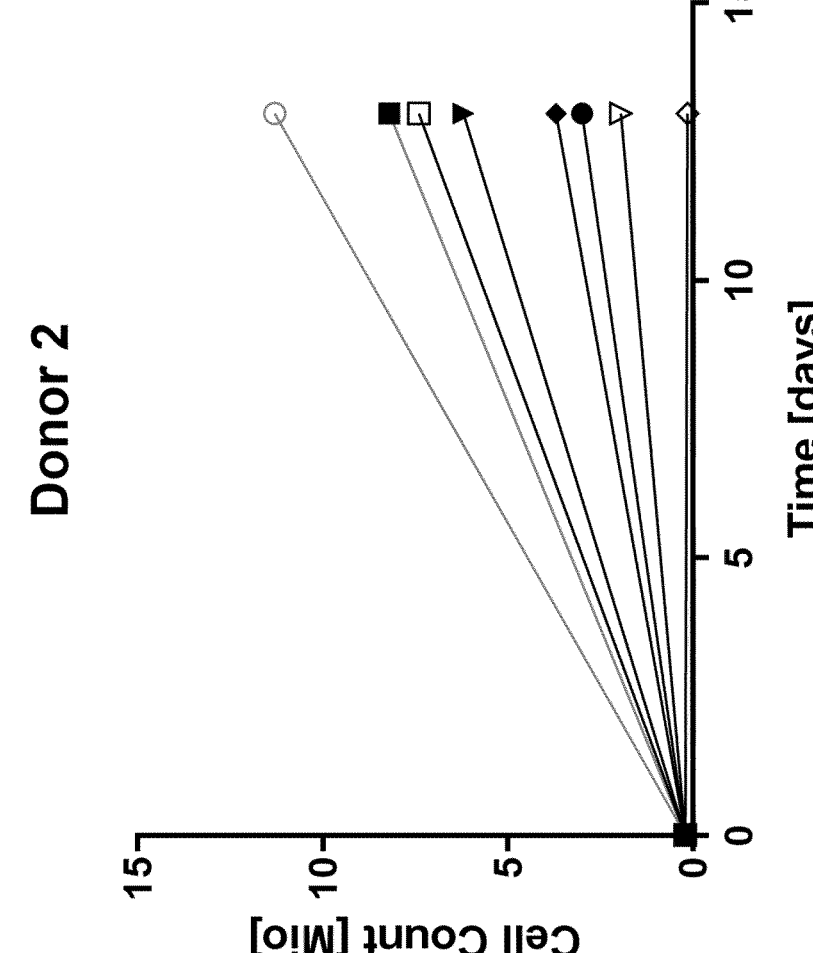

FIG. 11: Effector cell expansion after TCR transduction. Cell numbers of effector cells were determined at the day of transduction and subsequently after 13 days of expansion using a hemocytometer. Each graph represents one donor. TCR ImCorePrefCombi1 showed no effector cell expansion and could therefore not be included in further experiments.

Figure 12:
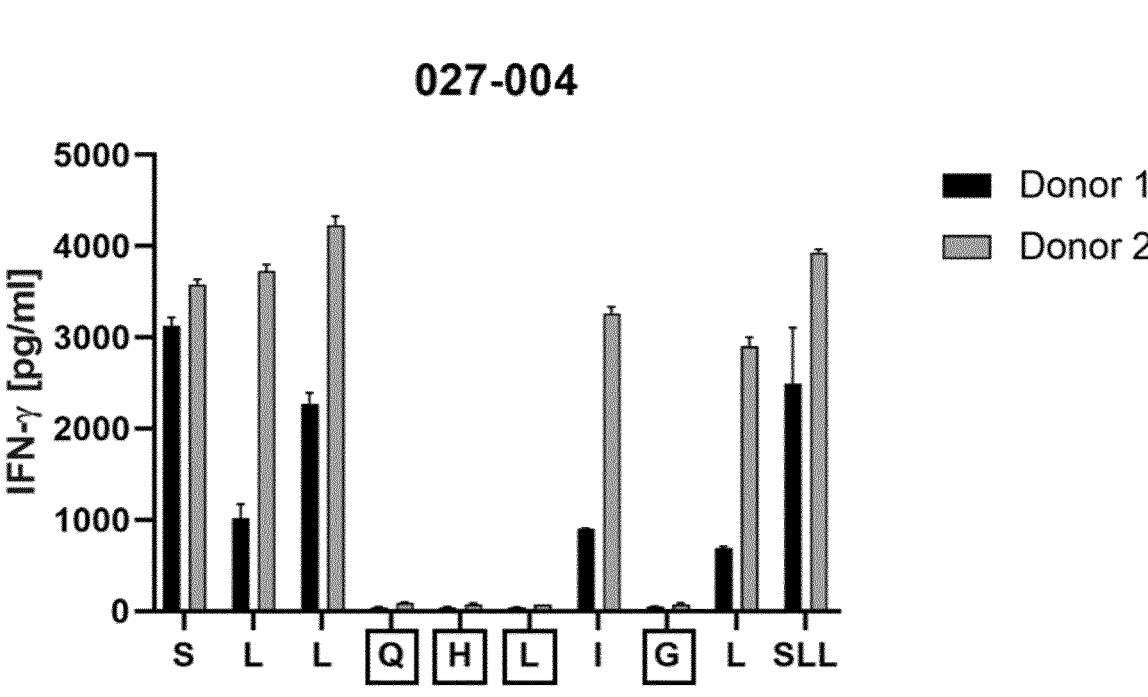
Figure 12:
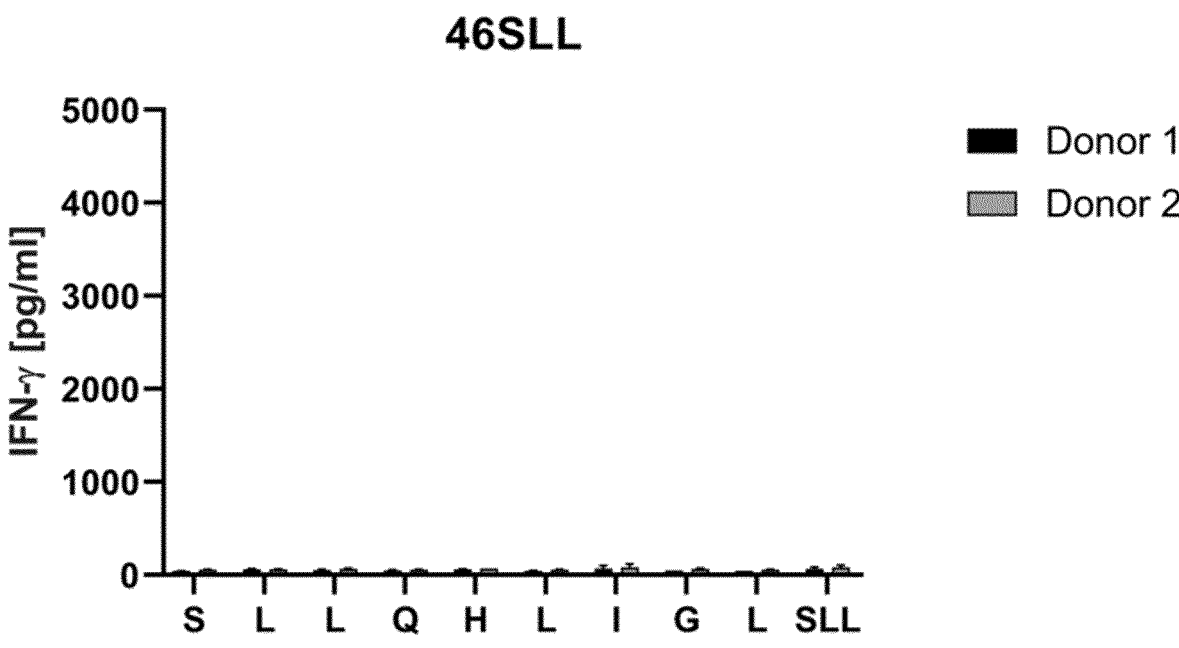
Figure 12:
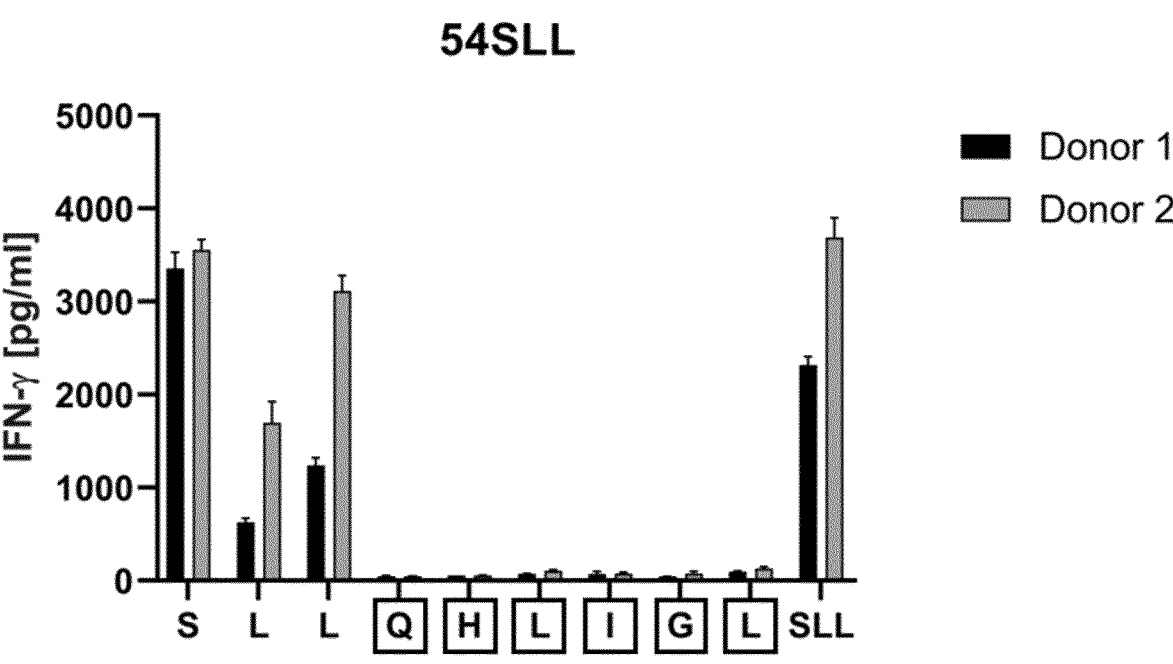
Figure 12:
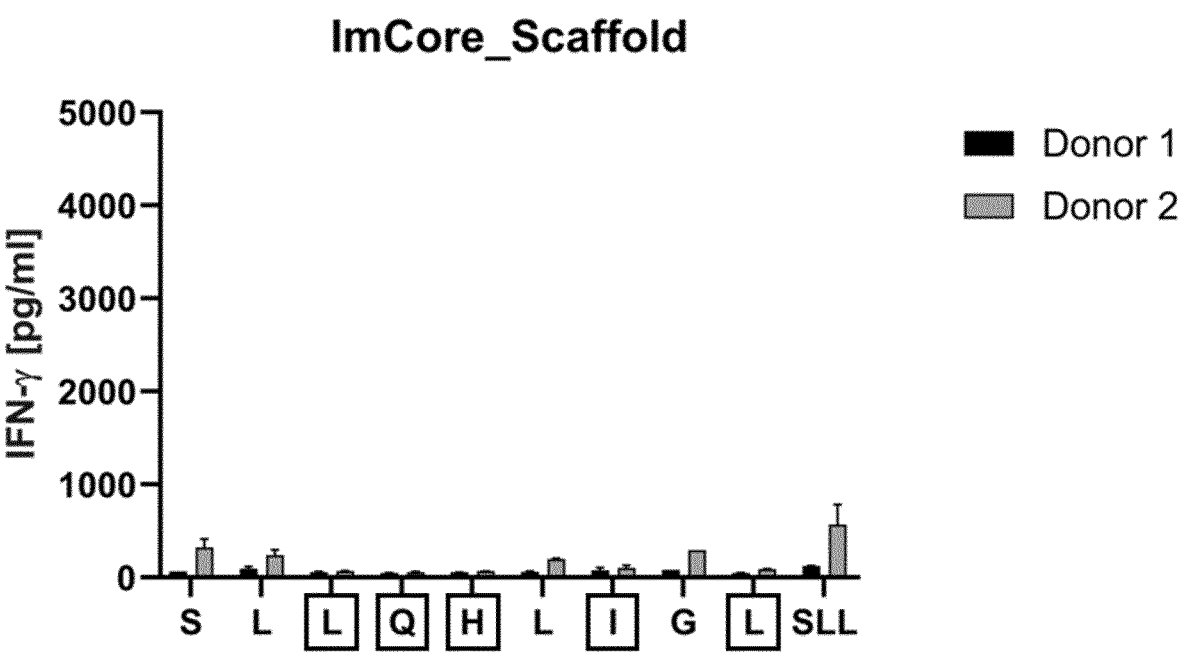
Figure 12:
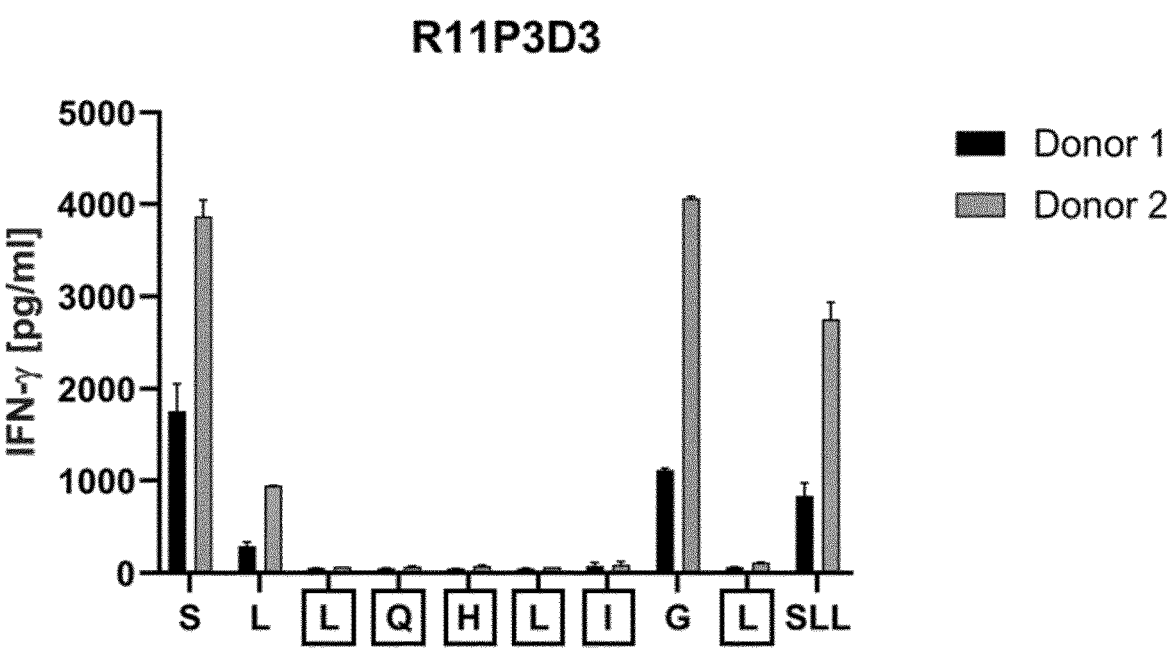
Figure 12:
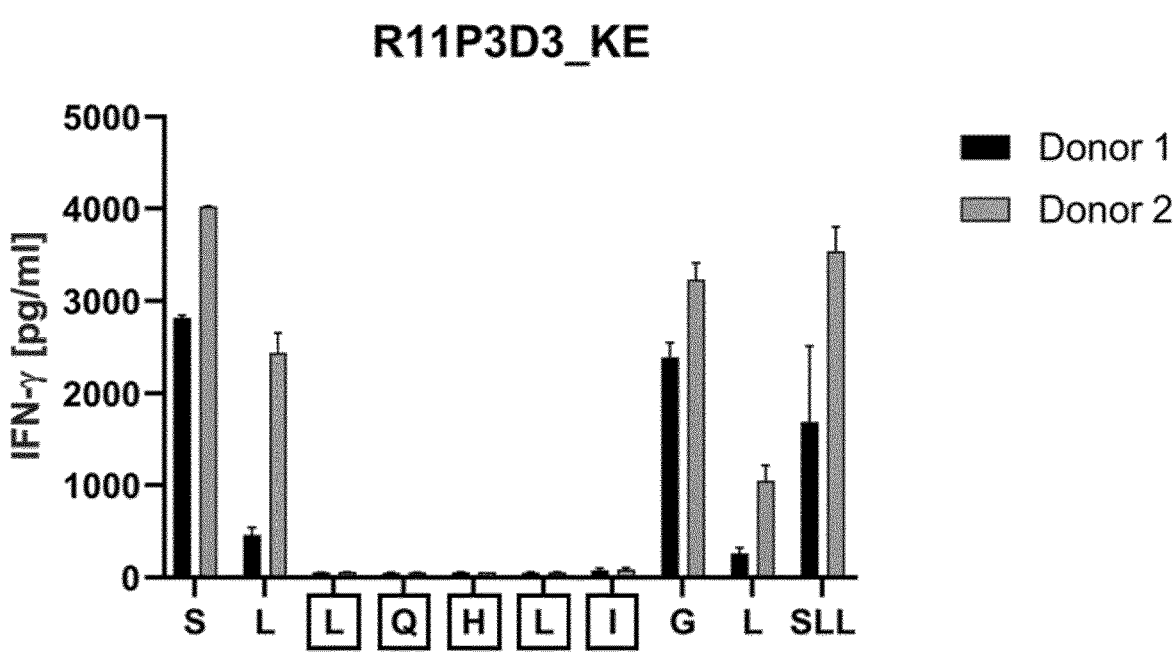

FIG. 12: TCR T23.8-2.1027-004 has a different recognition motif than state of the art TCRs. TCR-transduced effectors (effector cells) were co-cultured with T2 cells, loaded with the PRAME-SLL-peptide (far right) or SLL-peptide variants with single amino acid substitutions to threonine. As a read-out, supernatants were harvested after 20 h and analyzed by IFN-gamma ELISA. Each graph represents one TCR. Letters on X-axis indicate the position of amino acid substitution. "Fixed" positions of the recognition motif are highlighted by the boxes on the X-axis. TCR 46SLL did not show recognition of T2 cells loaded with the original PRAME-SLL peptide and TCR ImCore_Scaffold shows a reduced recognition of T2 cells loaded with PRAME-SLL. For the avoidance of doubt it is noted that within this description the inventive TCR is abbreviated TCR 027-004, wherein the full name is TCR T23.8-2.1-027-004.

Figure 13:
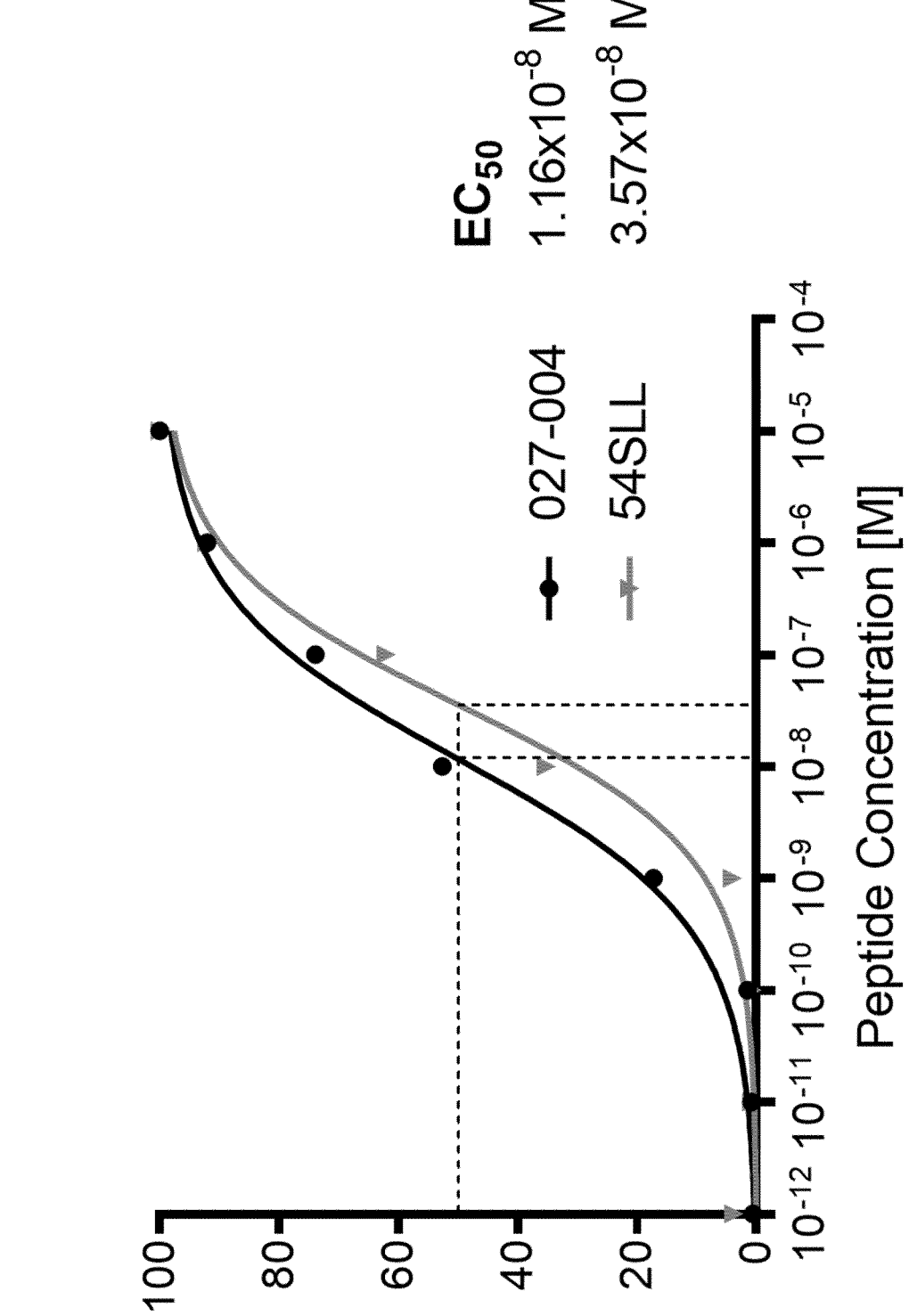
Figure 13:
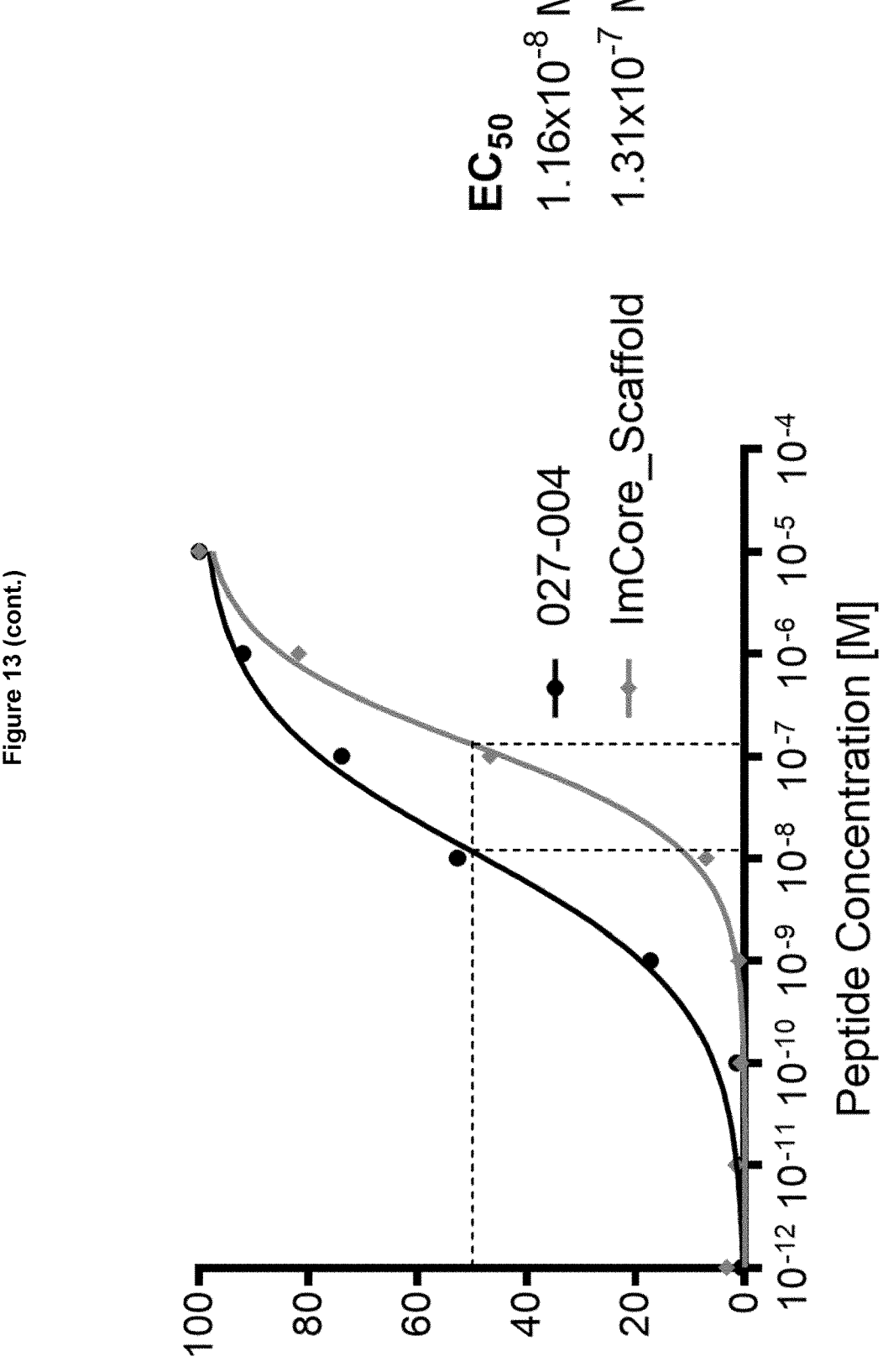
Figure 13:
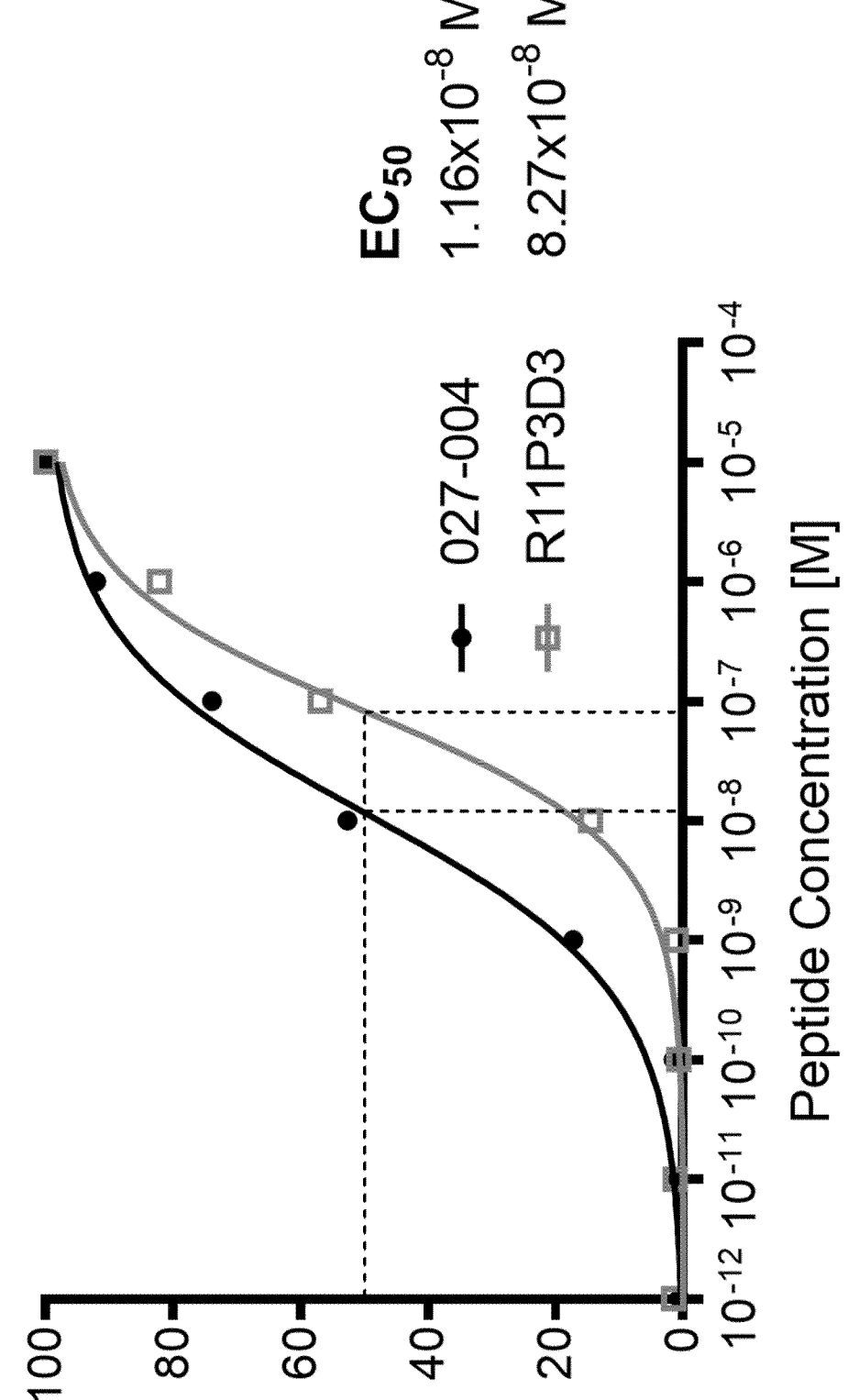
Figure 13:
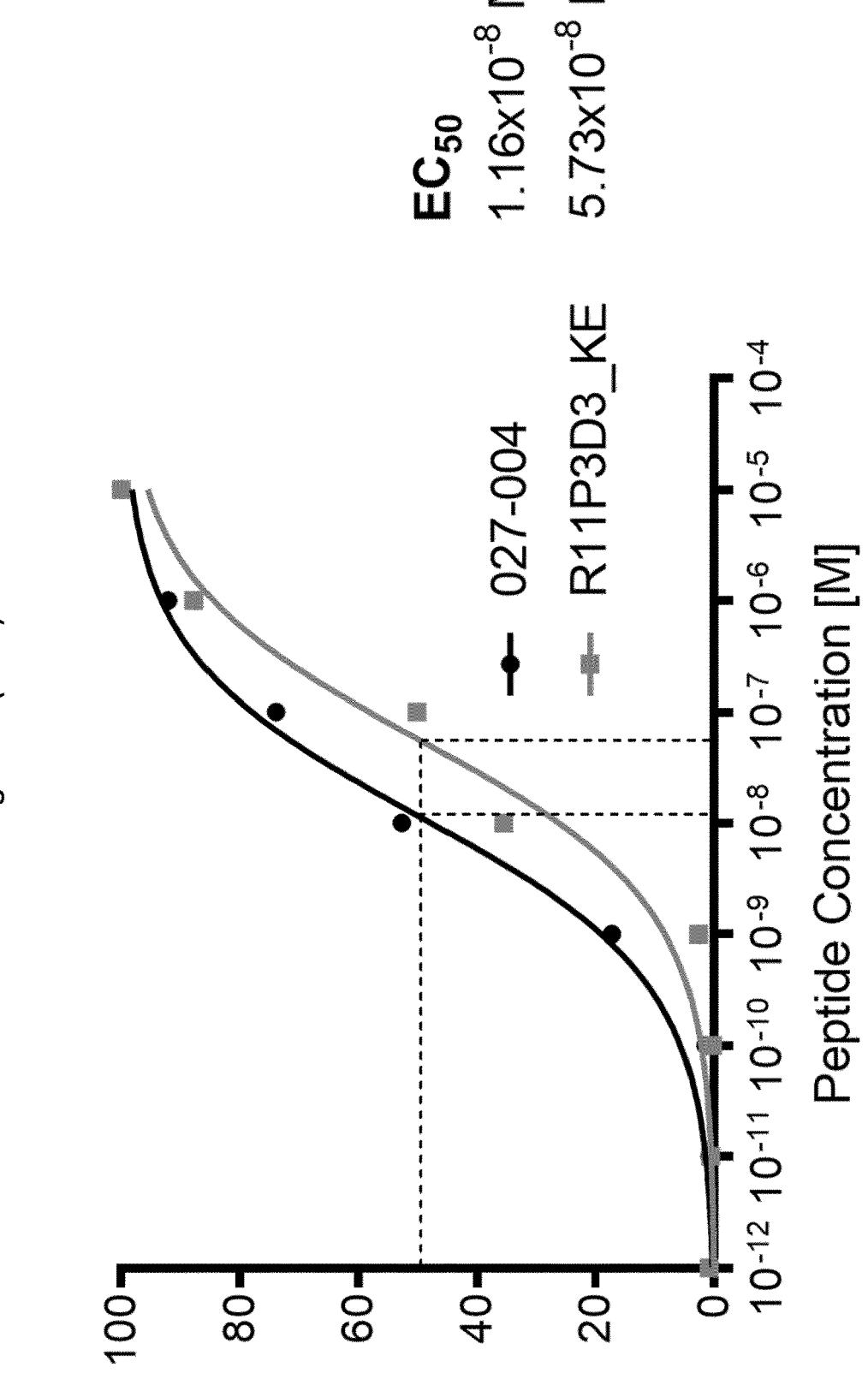

FIG. 13: TCR T23.8-2.1-027-004-transduced effectors have a higher functional avidity than effectors transduced with state of the art TCRs. TCR T23.8-2.1-027-004-transduced effectors (black) and other TCR-transduced effectors (grey) were co-cultured with T2 cells loaded with titrated amounts of the PRAME-SLL-peptide. As a read-out, supernatants were harvested after 20 h and analyzed by IFN-gamma ELISA. Peptide concentration needed for half maximal IFN-gamma secretion is indicated by dashed lines. The graph shows nonlinear regression curves representing O.D. values. A nonlinear regression analysis was used to calculate the $EC_{50}$ values for the different TCR-transduced effectors. Each graph represents the comparison of one state of the art TCR to TCR T23.8-2.1-027-004.

Figure 14:
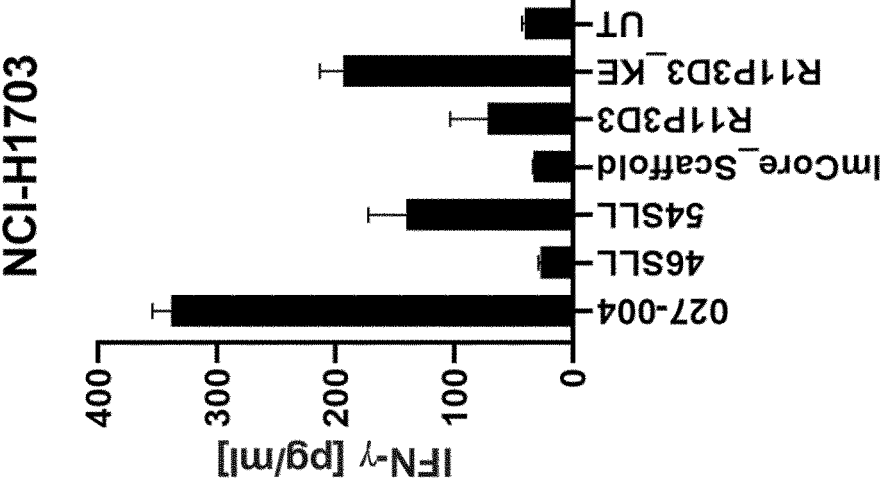
Figure 14:
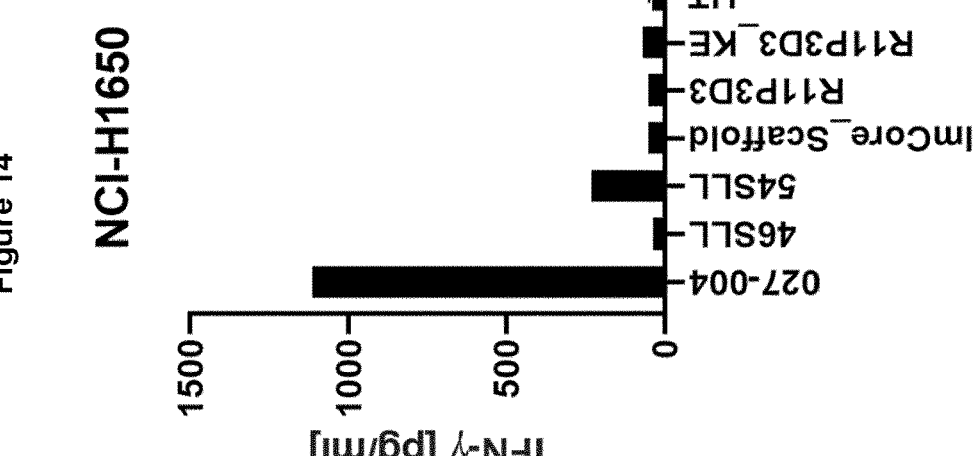
Figure 14:
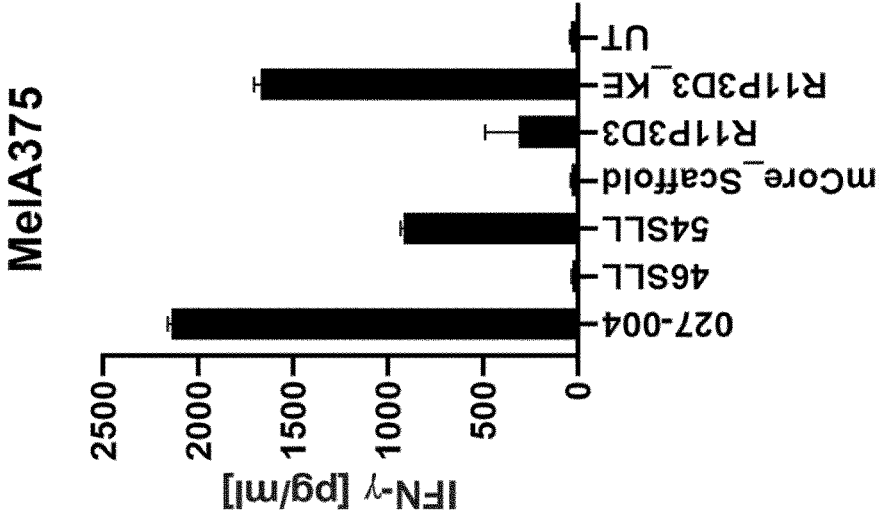

FIG. 14: T23.8-2.1-027-004-transduced effectors recognize HLA-A*02:01/PRAME double-positive tumor cell lines more strongly than effectors transduced with state of the art TCRs. Effectors transduced with six different TCRs, as well as untransduced control effectors, were co-cultured with the HLA-A*02:01/PRAME double-positive tumor cell lines MeIA375, NCI-H1650, and NCI-H1703. Supernatants of the co-culture were taken after 20 h and analyzed by ELISA to determine IFN-gamma secretion.

Figure 15:
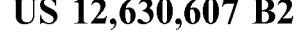
Figure 15:
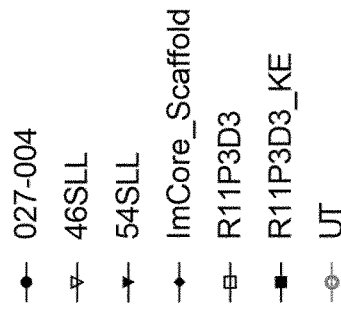
Figure 15:
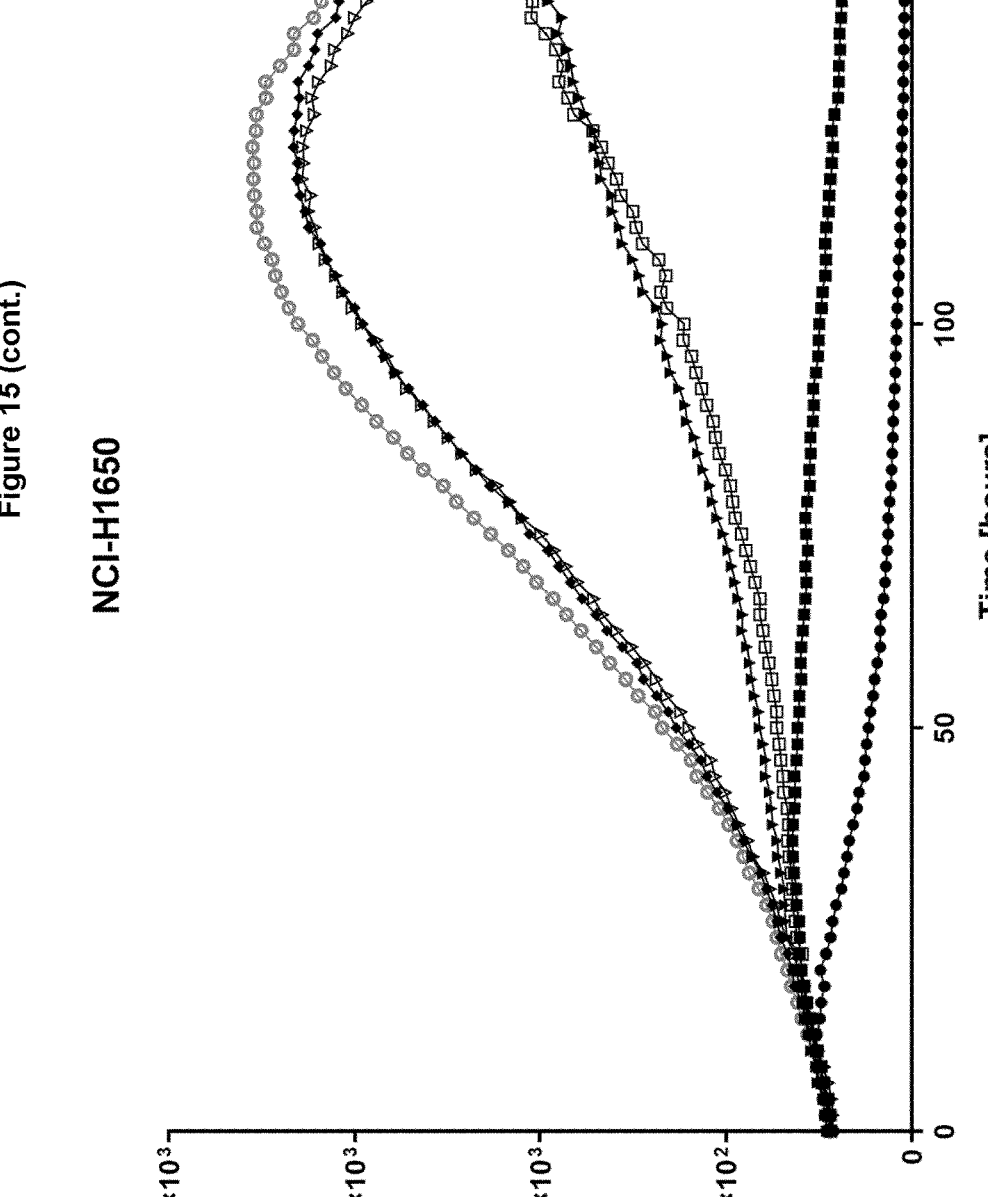

FIG. 15: T23.8-2.1-027-004-transduced effectors mediate lysis of PRAME-positive tumor cells more effectively than effectors transduced with state of the art TCRs. The NuclightRed-transduced tumor cell lines MelA375 and NCI-H1650 (HLA-A*02:01-positive/PRAME-positive), seeded in 96 well flat bottom plates, were co-cultured with untransduced effectors (represented in grey), T23.8-2.1-027-004-transduced effectors (black circles) or effectors transduced with other TCRs for 144 h. Loss of red fluorescence visualized tumor cell apoptosis. Untransduced effectors served as negative control. Shown are the red cell counts ($1/mm^2$) overtime of triplicates.

DETAILED DESCRIPTION OF THE INVENTION

Figure 1:
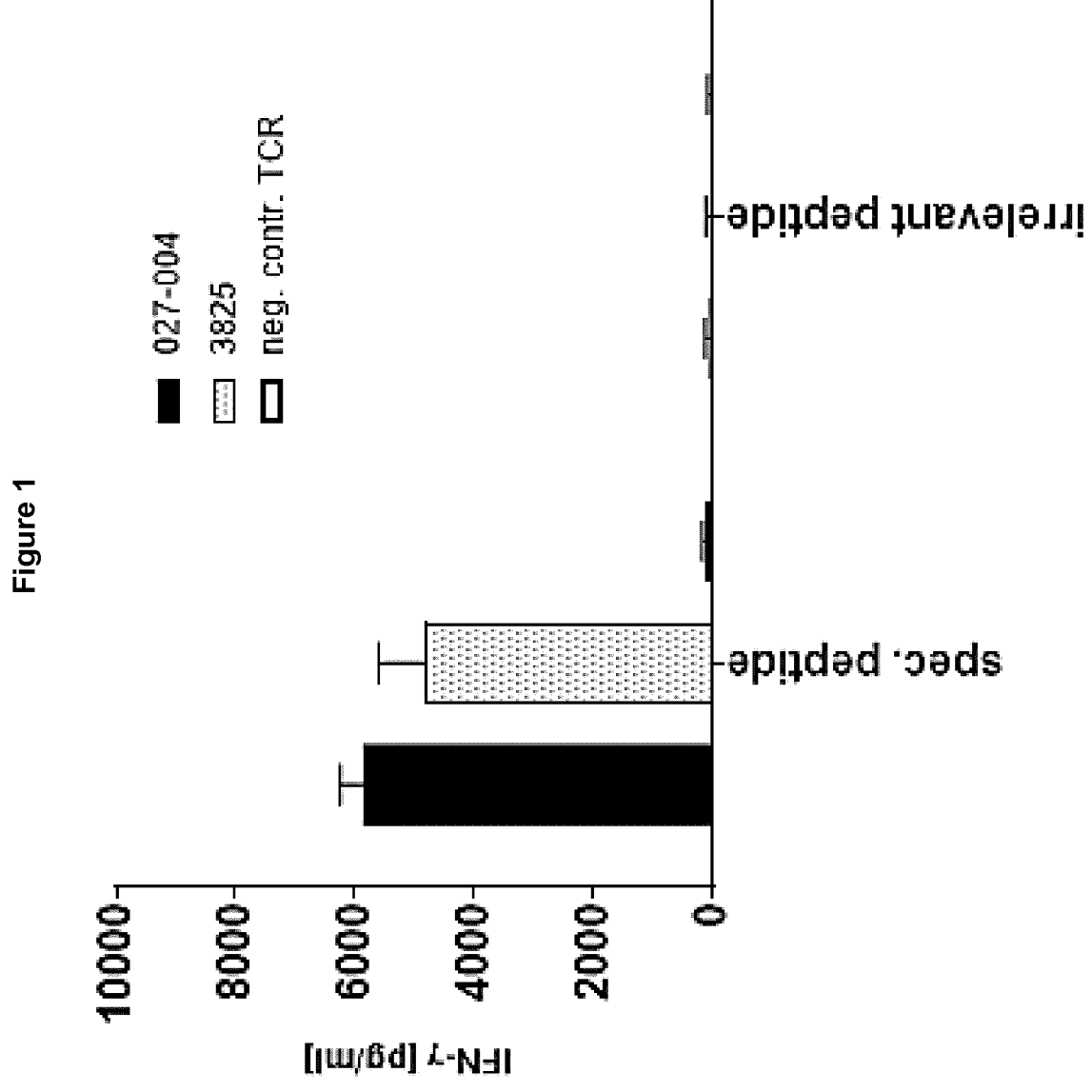
FIG. 1: Peptide specificity. T2 cells were either loaded with the specific SLL (SLLQHLIGL (SEQ ID NO: 1)) or an irrelevant peptide (GLSNTHVL (SEQ ID NO: 25)). These cells were then co-cultured with TCR transduced T cells. After 20 hours the IFN-gamma level in the cell culture supernatant was measured using an IFN-gamma ELISA. All TCR transduced effector cells, except the neg. contr. TCR, show recognition of the specific SLL peptide, but not the irrelevant peptide when loaded on T2 cells.
Figure 2:
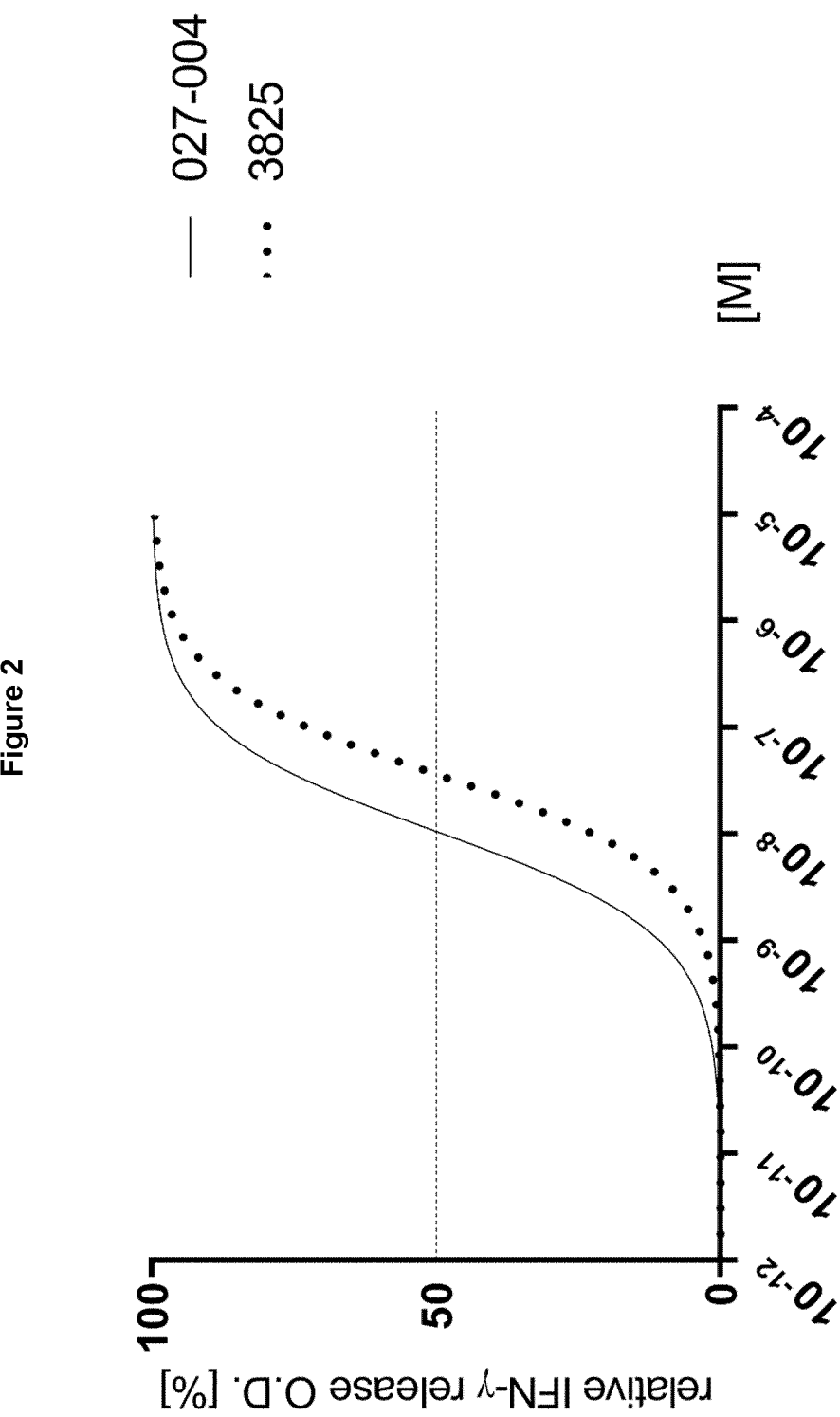
FIG. 2: Functional Avidity. Functional avidities of TCR-transgenic T cell populations are measured as the half-maximal relative IFN-gamma release ($EC_{50}$ values) in co-culture with T2 cells loaded with titrated amounts of SLL peptide ($10^{-5}$ M to $10^{-12}$ M). Cells transduced with the TCR 027-004 show higher functional avidity than TCR 3825 transduced T cells.
Figure 3:
FIGS. 3A and 3B: TCR recognition motif (Serine Scan). In vitro co-culture of TCR-transduced T cells with $10^{-5}$ M peptide-loaded T2 cells at an Effector:Target (E:T) ratio of 1:1 (10.000 effector cells/96-well). For this, T2 cells were loaded with peptides only varying in one amino-acid position being consecutively substituted by the amino-acid seine. T cells transduced with TCR 027-004 TCR (FIG. 3A) show a different recognition motif with less fixed positions compared to TCR clone 3825 transduced T cells (FIG. 3B).
Figure 3:
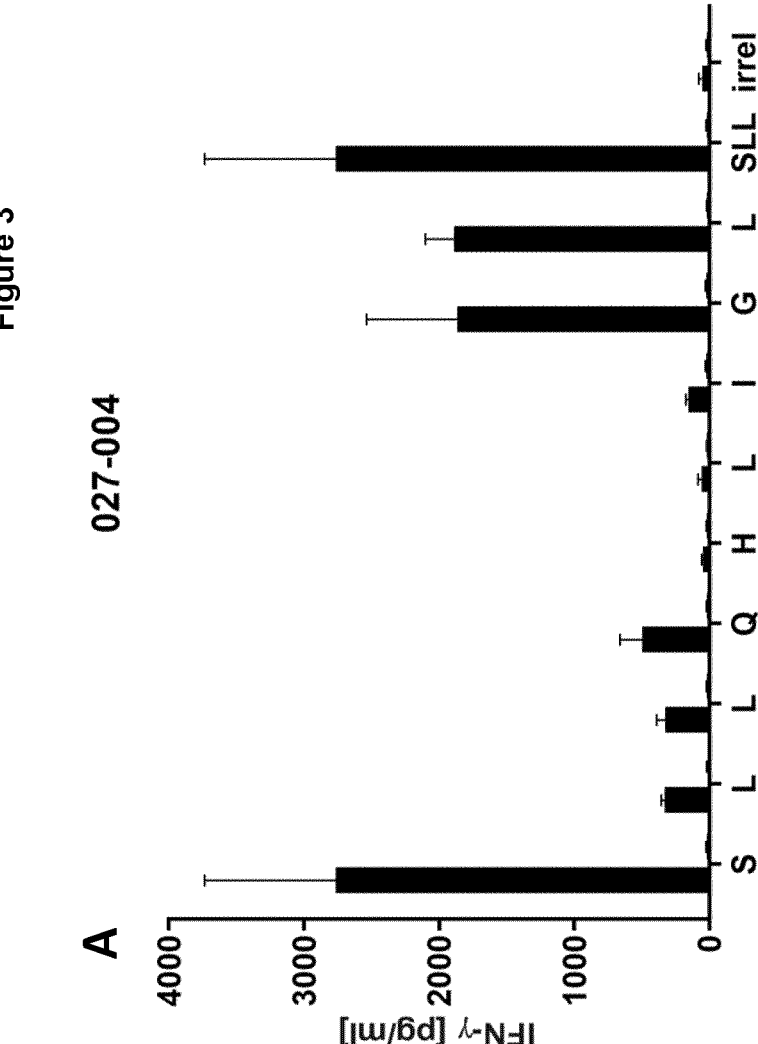
Figure 3:
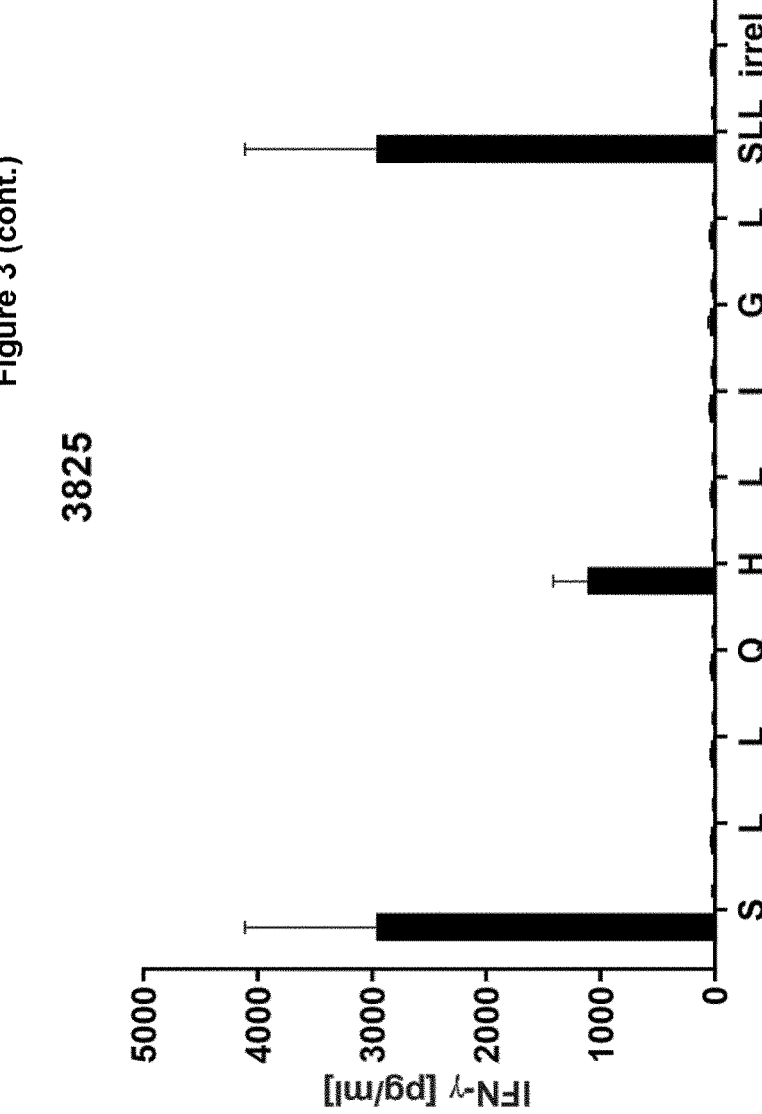
Figure 5:
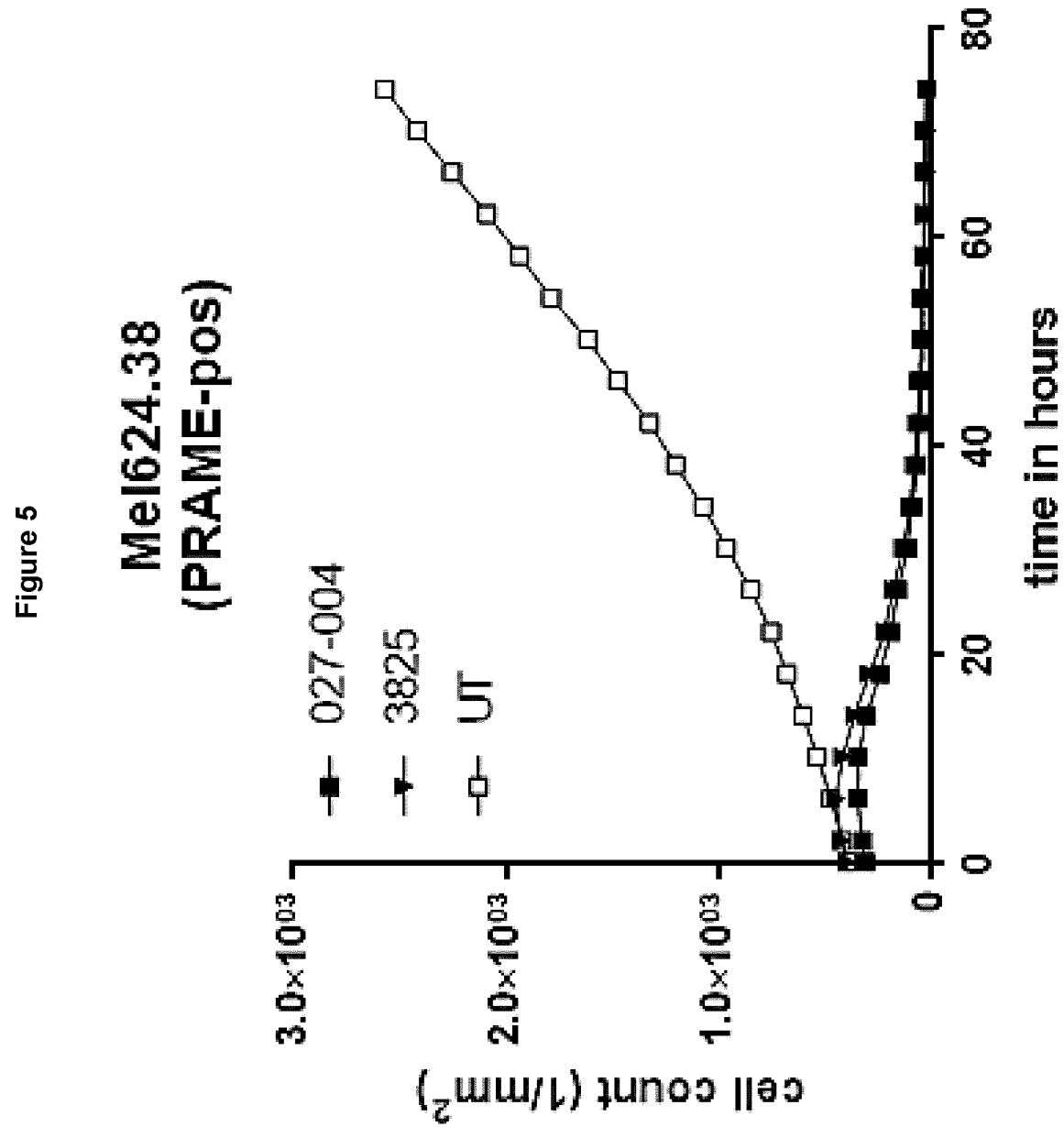
FIG. 5: Tumor cell killing. All TCR-transduced effector cells lyse $PRAME_{SLL}$ positive (PRAME-pos) tumor cells and do not influence the growth of $PRAME_{SLL}$-negative tumor cells (PRAME-neg). Effector cells transduced with TCR 027-004 show better killing of $PRAME_{SLL}$ positive cell lines compared to T cells transduced with TCR 3825.
Figure 5:
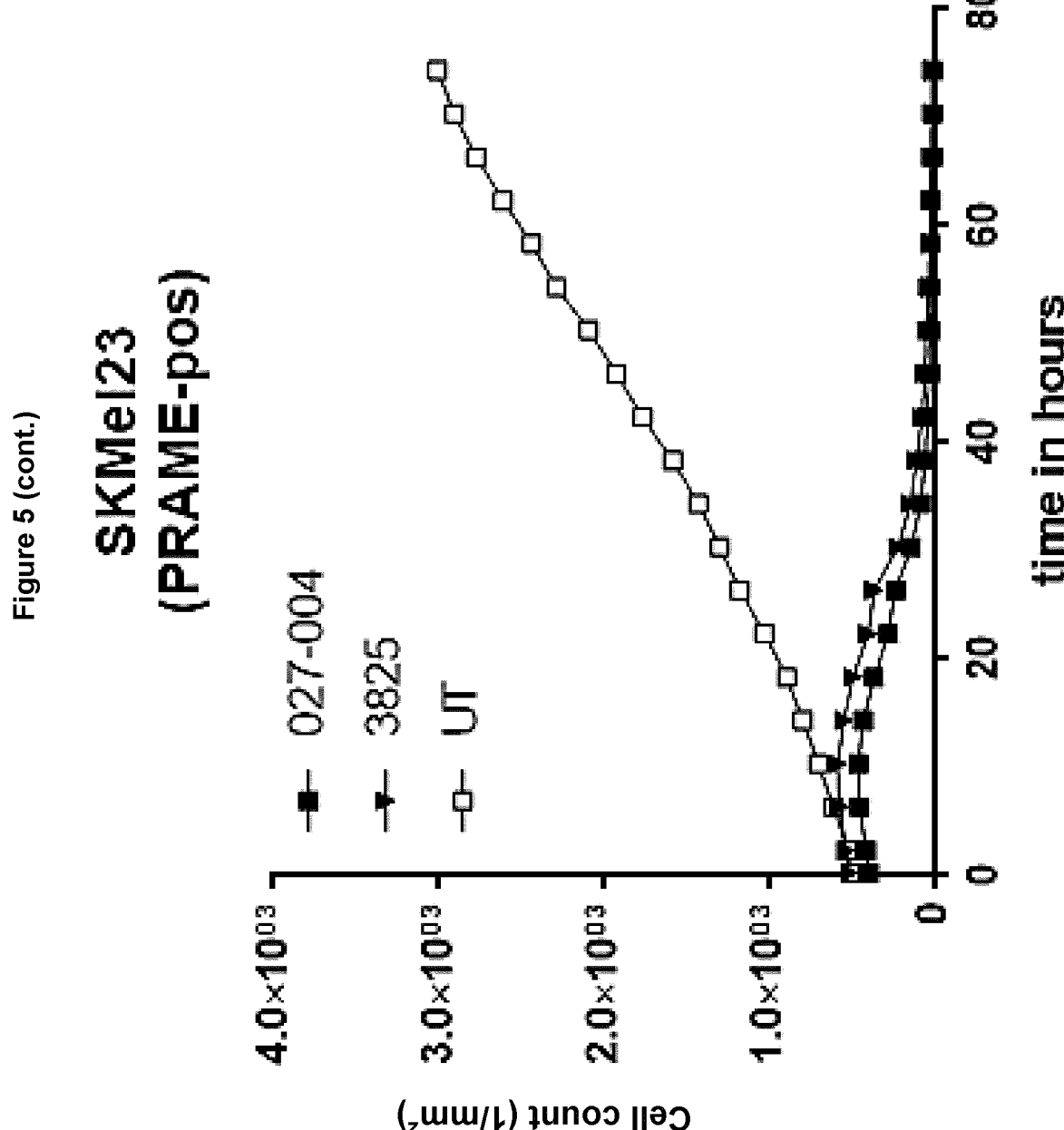
Figure 5:
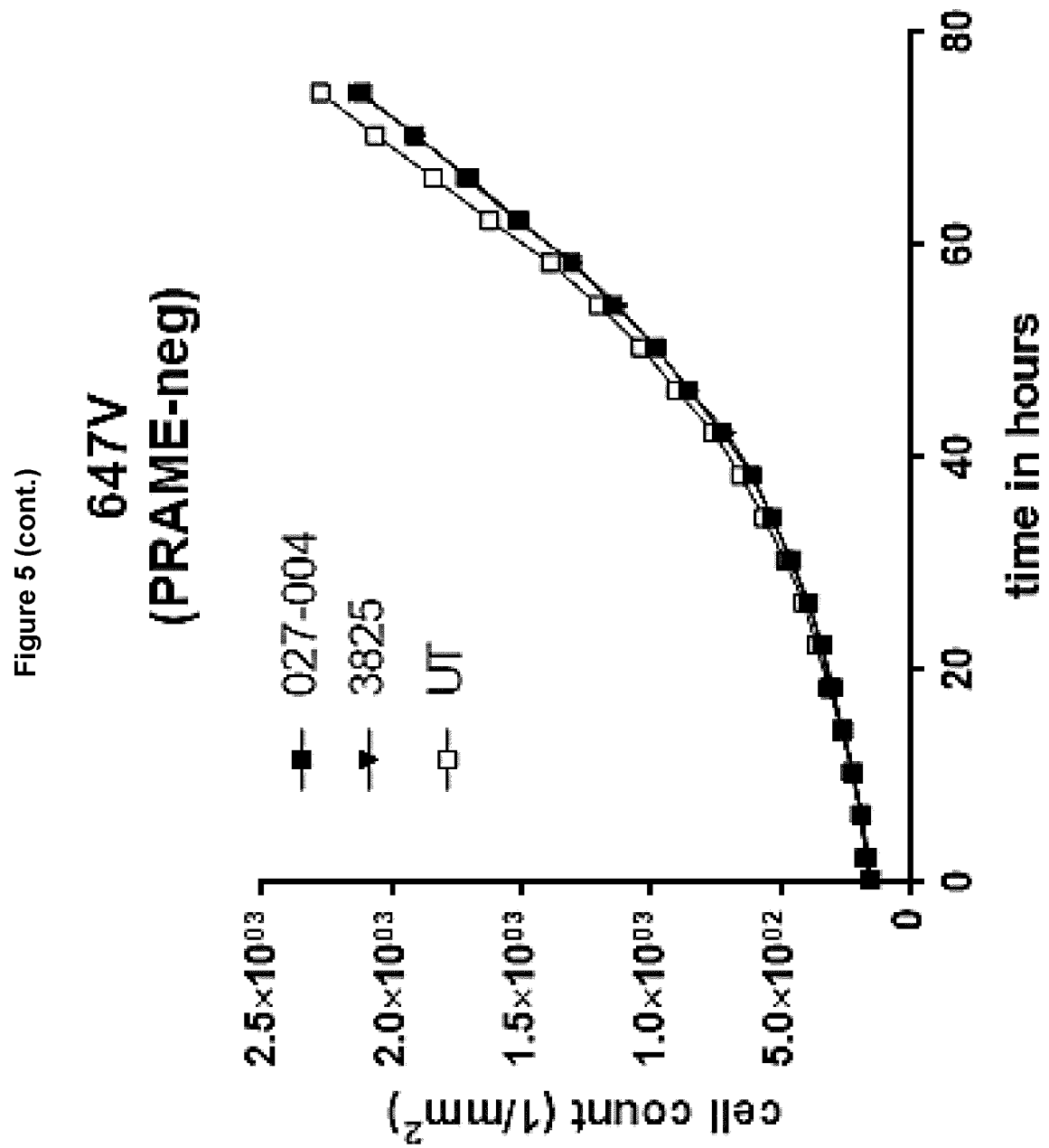
Figure 5:
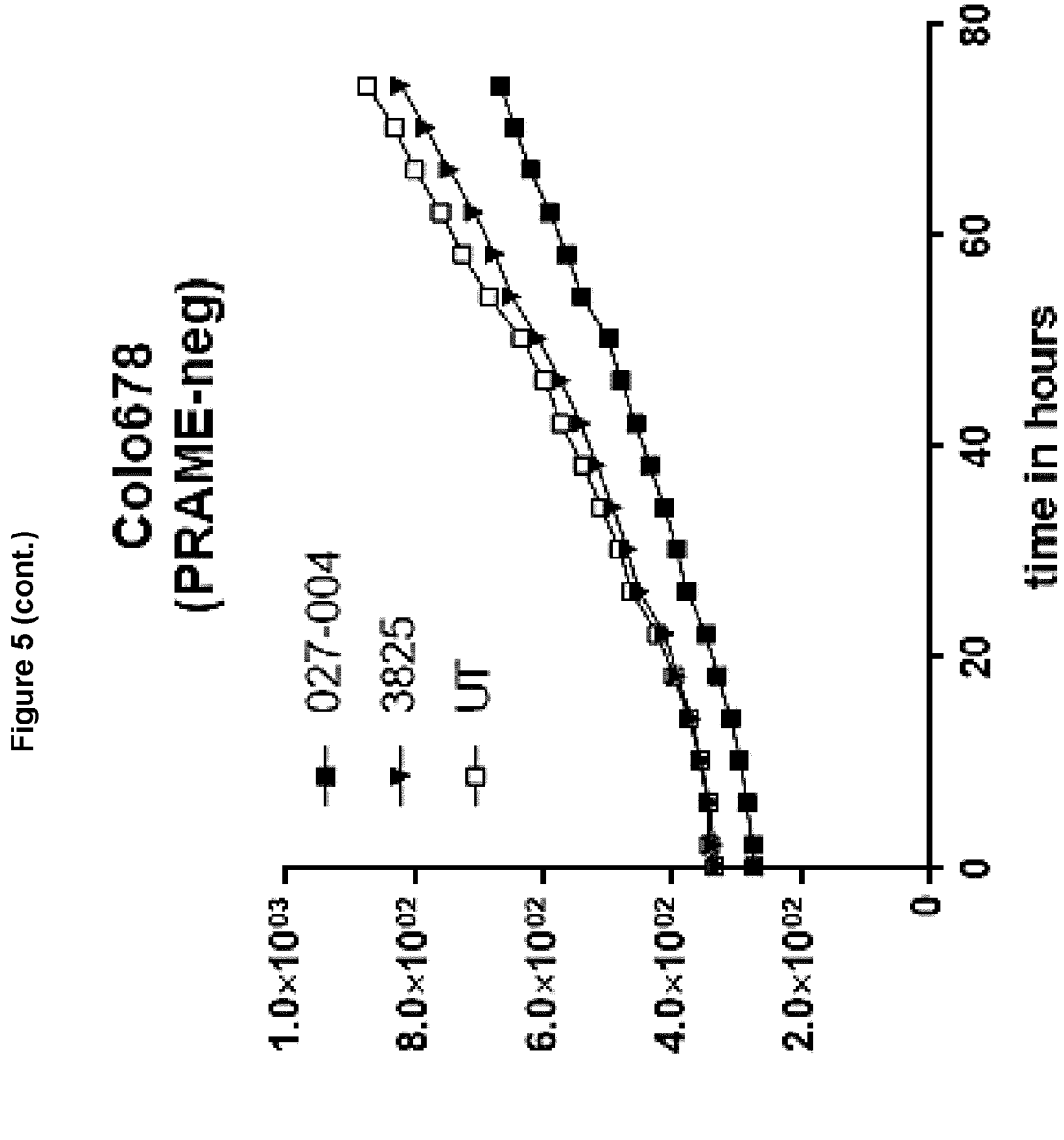
Figure 5:
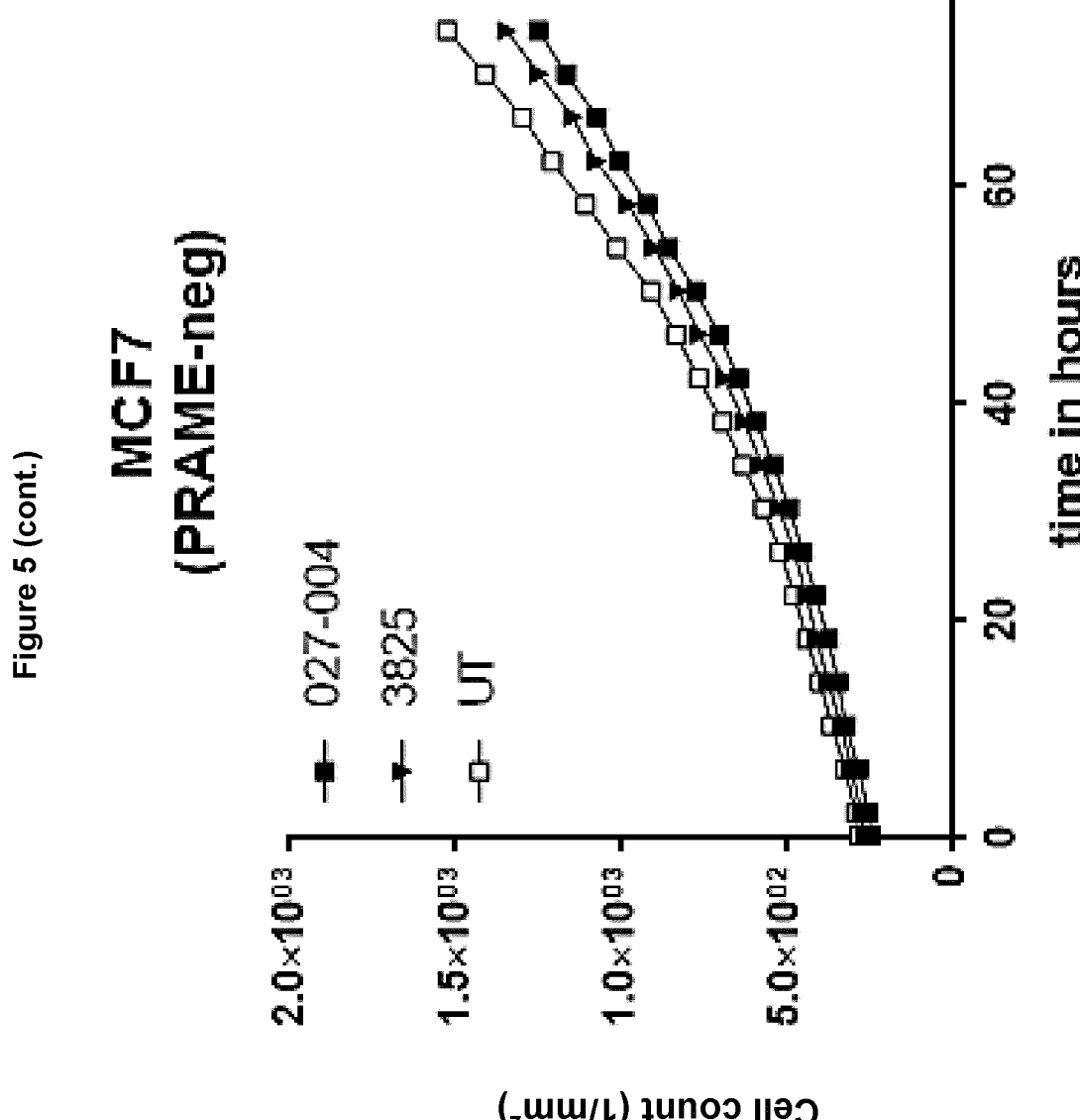
Figure 6:
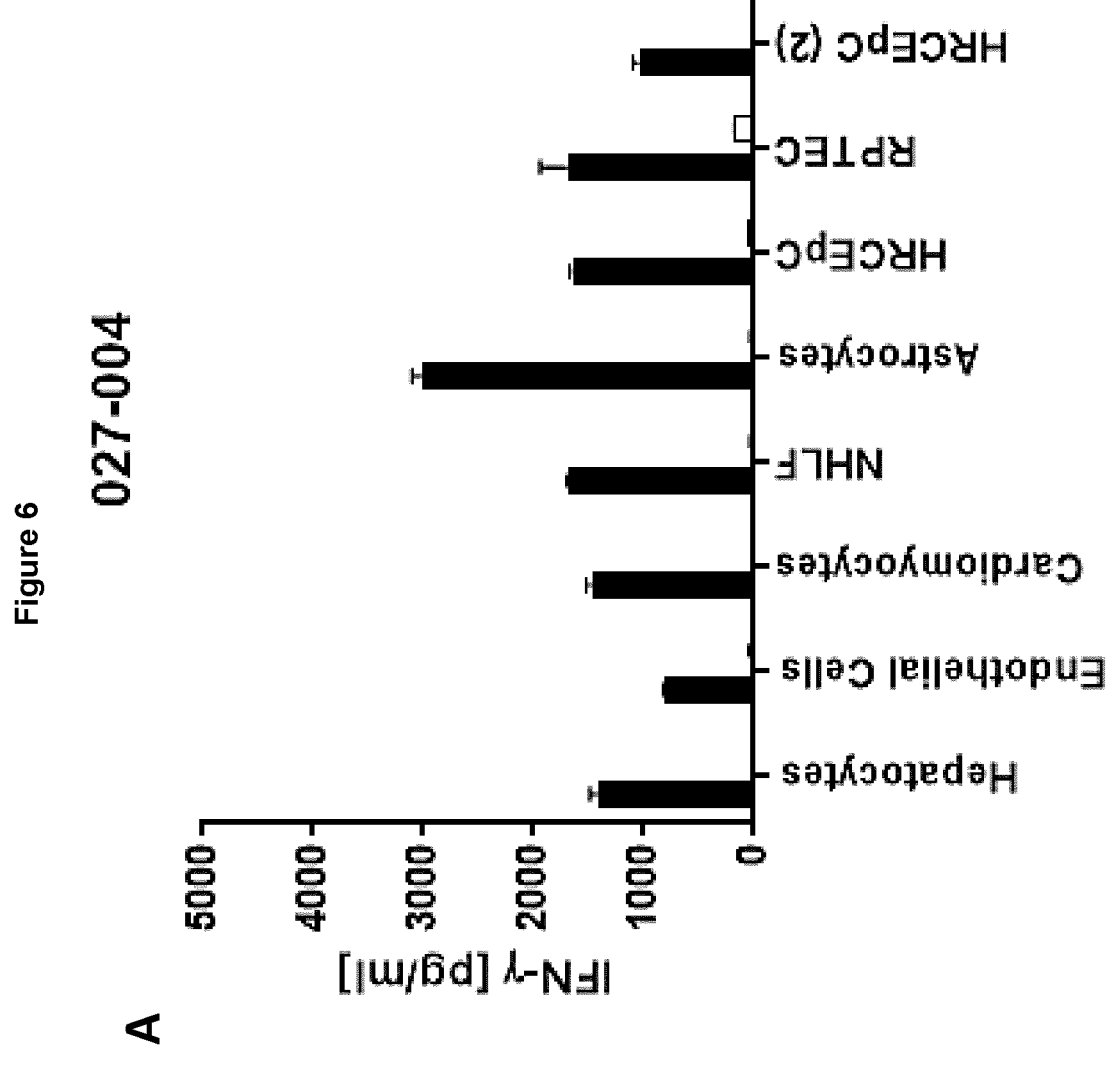
FIG. 6: Normal cell recognition. TCR transduced T cell populations do not recognize unloaded normal cells so that high levels of IFN-gamma are secreted. However, if the cells are loaded with the specific $PRAME_{SLL}$ peptide they are recognized by TCR 027-004. Only co-culture with the unloaded cell line RPTEC (endogenously PRAME-positive cell line) results in minimal IFN-gamma production in both effector preparations.
Figure 6:
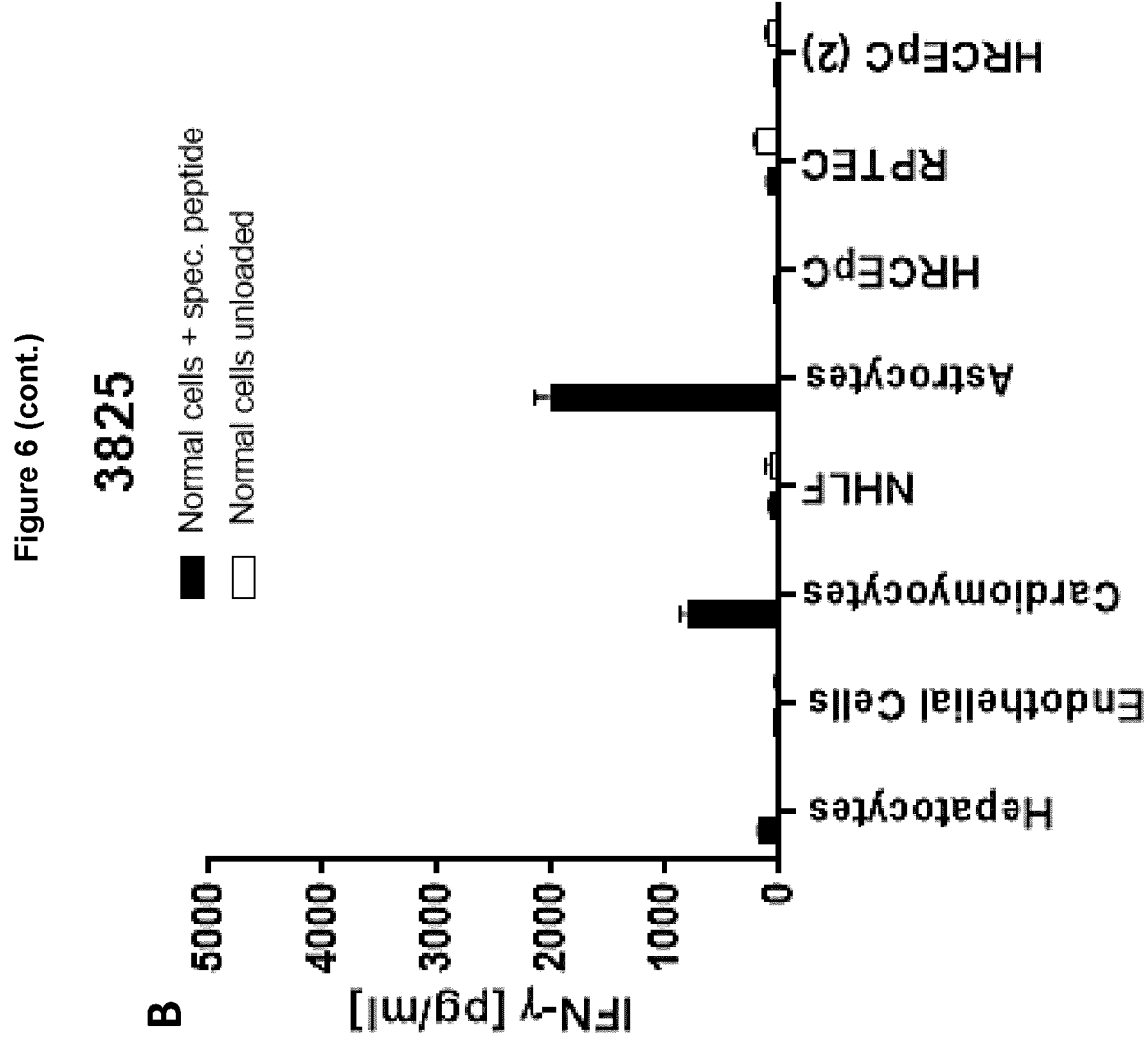

The inventors of the present invention have identified a T cell receptor (TCR) clone that is capable of recognizing cells expressing the tumor-associated antigen PRAME (PRAME full length as depicted in SEQ ID NO: 33), and especially the amino acid sequence SLLQHLIGL (SEQ ID NO: 1) also referred to as PRAME$_{SLL}$ herein. This sequence is recognized in a specific manner, while irrelevant peptides cannot be recognized (FIG. 1). Said specificity is expressed by the recognition of only PRAME-positive cancer cell lines (FIGS. 4 and 5), while PRAME-negative and unloaded normal cells are not recognized by said TCR receptor. However, normal cells will be recognized when loaded with PRAME$_{SLL}$ peptide (FIG. 6). This selective recognition can be obtained by the recognition motif of the T cell receptor, displaying only a few fixed positions (FIG. 3). The amino acids LLQ and especially HLI of the sequence SLLQHLIGL (SEQ ID NO: 1) are part of this recognition motif. These amino acids exhibit advantageous effector functions such as a high accumulated strength of multiple affinities (e.g. functional avidity, FIG. 2) for PRAME peptide.

Figure 4:
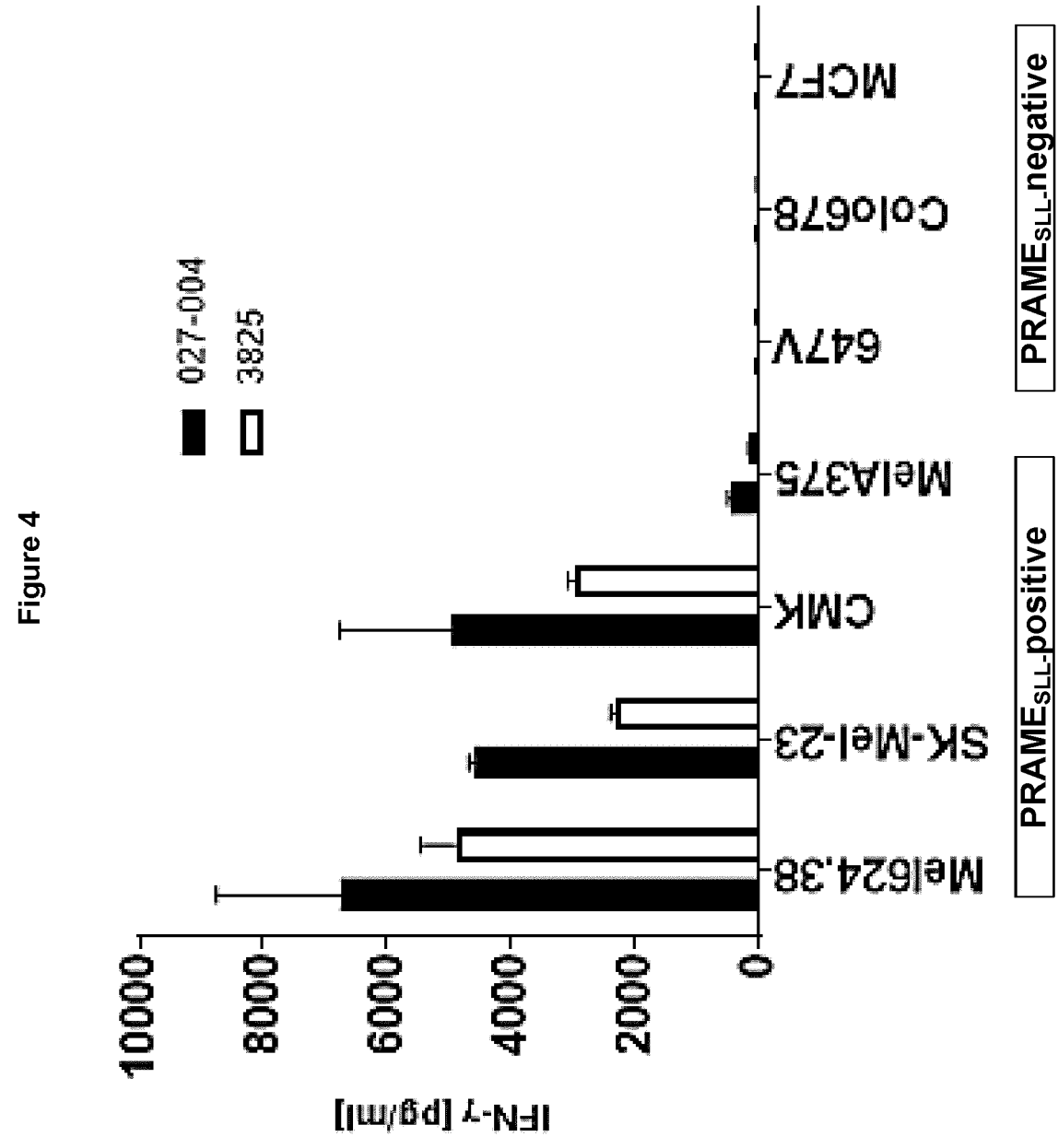
FIG. 4: Tumor cell recognition. Both TCR-transduced T cell populations (transduced with either TCR 027-004 or 3825) recognize $PRAME_{SLL}$ positive tumor cell lines. Recognition of the $PRAME_{SLL}$ positive cell line is higher with 027-004 TCR-transduced T cells compared to 3825 TCR-transduced T cells. $PRAME_{SLL}$ negative tumor cells are not recognized by any of the TCRs tested.
Figure 8:
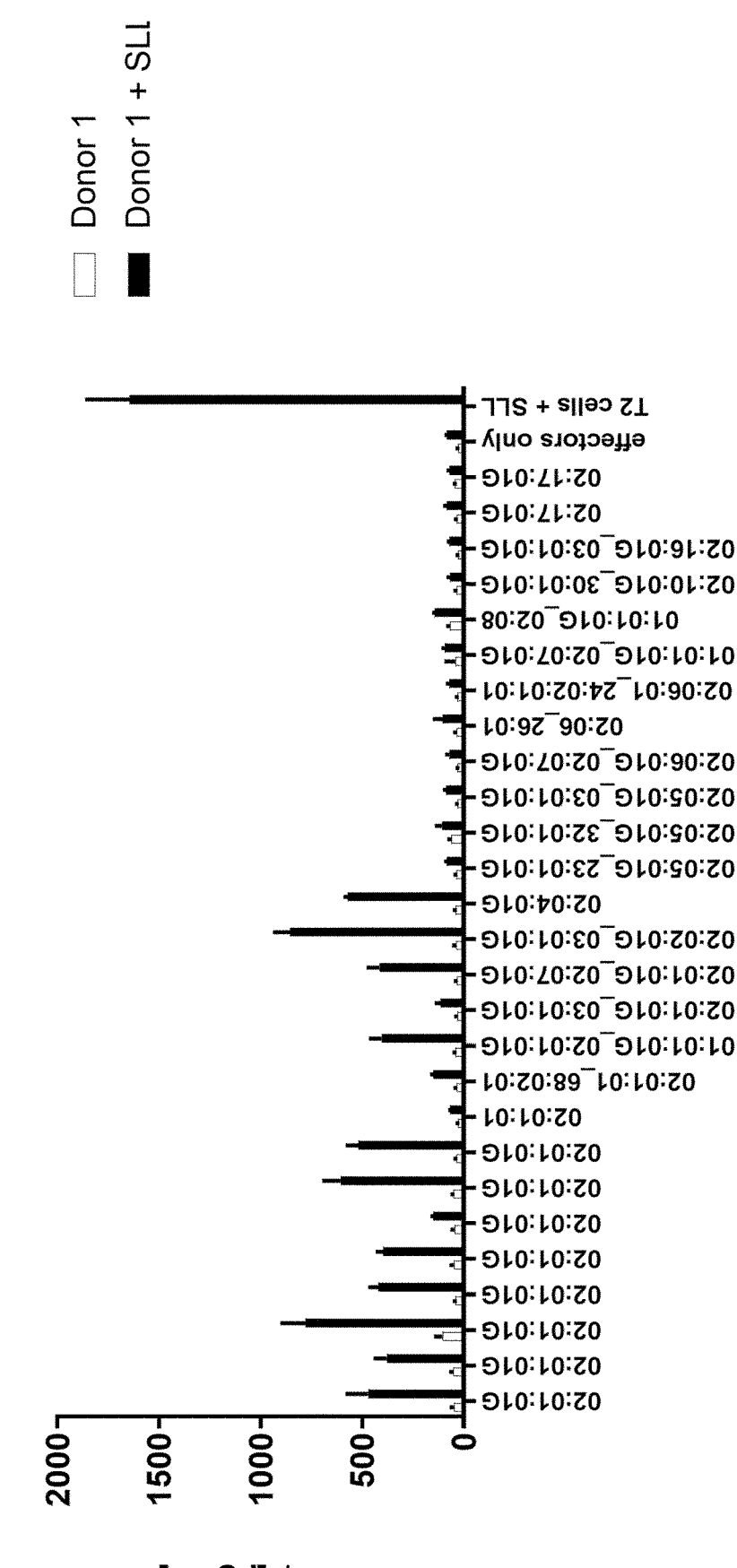
FIG. 8: HLA-A*02 fine typing of TCR 027-004. In vitro co-culture of T cells transduce with TCR 027-004 with selected HLA-A2 sub-allele-positive lymphoblastoid cell lines (LCL; EBV-transformed B cells) at an Effector:Target (E:T) ratio of 1:2 (10.000 effector cells/96-well). All individual LCLs are SLL peptide-loaded ($10^{-5}$ M) to determine the unique TCR sub-allele recognition. Unloaded target cells serve as negative control. IFN-gamma secretion was determined using standard ELISA after 20 hours of co-culture. The TCR 027-004 efficiently recognizes the PRAME peptide presented by 3 of 10 tested HLA-A2 sub-alleles (A*02: x), the HLA-A*02 sub-alleles A*02:02 and A*02:04 are recognized at comparable levels compared to A*02:01.
Figure 9:
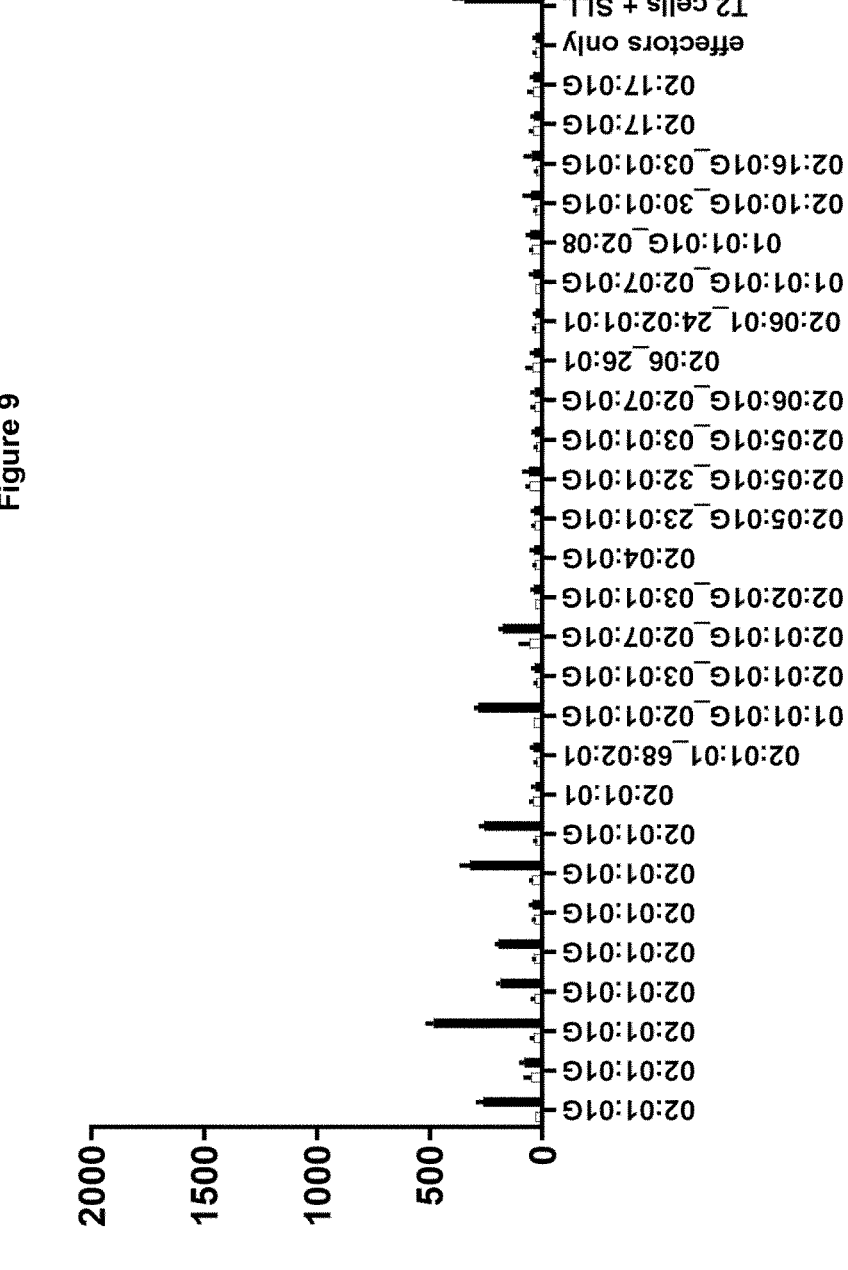
FIG. 9: HLA-A*02 fine typing of TCR 3825. In vitro co-culture of T cells transduced with TCR 3825 with selected HLA-A*02 sub-allele-positive lymphoblastoid cell lines (LCL; EBV-transformed B cells) at an E:T ratio of 1:2 (10.000 effector cells/96-well). All individual LCL are SLL peptide-loaded ($10^{-5}$ M) to determine the unique TCR sub-allele recognition. Unloaded target cells serve as negative control. IFN-gamma secretion was determined using standard ELISA after 20 hours of co-culture.

In sum, the T cell receptor identified by the present inventors is capable of specifically recognizing cells expressing the tumor-associated antigen (TAA) PRAME, and in particular PRAME$_{SLL}$. Said TCR exhibits advantageous effector functions such as cytokine production and cytolysis of target cells. Said T cell receptor is therefore a promising tool for a highly specific and effective cancer treatment. The identified PRAME-specific TCR is thus suitable for adoptive T cell therapy of cancer. The above said allows T cells to be armed ex vivo and re-introduced into the donor, where they can effectively recognize and specifically eliminate PRAME expressing cancer cells (FIGS. 4 and 5). In this context, recognition of different HLA sub-alleles can be advantageous to be able to include patients of different sub-allele types into a study cohort covering different frequencies of the world population (FIG. 7). The herein described TCR receptor recognizes HLA-A*02:01, as well as HLA-A*02:02, and HLA-A*02:04 encoded molecules (FIGS. 8-10). Thus, being a potential cancer treatment for a large population of cancer patients with PRAME expressing tumors. Moreover, the antigen binding regions of the novel TCR provided herein, can be used to design soluble constructs comprising further functional moieties (such as drugs, labels or further binding domains attracting other immune cells) that are readily available for direct administration.

To further prove the effect of the TCRs of the present invention in the light of the state of the art, the inventors compared the TCR recognition motif, tumor cell recognition, functional avidity and killing capacities to TCRs known from the art. Selected were two TCRs from WO2016142783 (46SLL and 54SLL), two TCRs from WO2018234319 (ImCore_Scaffold and ImCorePref-Combi1) and two additional TCRs which were described in WO2018172533 (R11P3D3 and R11P3D3_KE). Table 2 provides an overview of these selected clones and their respective publications.

From FIG. 11 it is apparent that the TCR ImCorePref-Combi1 showed no effector cell expansion and could therefore not be included in subsequent experiments. The selected TCRs were analyzed in a Threonine Scan (FIG. 12), which could prove a different composition of the amino acids forming the respective recognition motif. Importantly, none of the selected TCRs reached an $EC_{50}$ value of the relative IFN-gamma release at lower peptide concentrations than the TCR of the present invention (T23.8-2.1-027-004) in the same experimental setup. In FIG. 13 the $EC_{50}$ values of the best performing TCRs of the prior art are plotted against the TCR of the present invention. The herein described TCR T23.8-2.1-027-004 reached an $EC_{50}$ value at a peptide concentration of $1.16 \times 10^{-8}$ M, in comparison to $3.57 \times 10^{-8}$ M of the TCR 54SLL, and $1.31 \times 10^{-7}$ M of the TCR ImCore_Scaffold. Other TCRs did not perform as good as the TCR of the present invention either; they reached their EC50 values at a peptide concentration of $8.27 \times 10^{-8}$ M (R11P3D3) and $5.73 \times 10^{-8}$ M (R11P3D3_KE). The TCR of the present invention therefore elicits a higher functional avidity than the TCRs of the prior art.

To further investigate the tumor cell recognition, three PRAME expressing tumor cell lines were co-cultured with effector cells transduced with the different TCRs and the respective IFN-gamma release was measured after 20 h of co-culture (FIG. 14 and Table 3). Effector cells transduced with the TCR of the present invention displayed the highest IFN-gamma release after co-culture with the tumor cell lines MelA375, NCI-H1650 and NCI-H1703.

Finally, the PRAME expressing tumor cell lines MelA375_NuclightRed and NCI-H1650_NuclightRed were used to analyze the tumor cell killing. As shown in FIG. 15 and Table 4, effector cells transduced with the TCR of the present invention lysed tumor cells more effectively than effector cells, which were transduced with other state of the art TCRs.

From the above mentioned data it can be concluded that the TCR of the present invention has a higher functional avidity than TCRs disclosed in the prior art, recognizes the tested tumor cell lines best, and lyses PRAME positive tumor cells more efficiently.

Variable Region

CDR3 Domains

In a first aspect the present invention refers to a T cell receptor (TCR) capable of binding to a PRAME peptide having the amino acid sequence SLLQHLIGL (SEQ ID NO: 1) or a portion thereof, or its HLA-A2 bound form, wherein the TCR comprises: a CDR3 of the TCR alpha chain variable region comprising or consisting of the amino acid sequence of (SEQ ID NO: 6), and/or a CDR3 of the TCR beta chain variable region comprising or consisting of the amino acid sequence of (SEQ ID NO: 7). Further envisaged are TCR sequence variants comprising a CDR3 alpha comprising or consisting of an amino acid sequence having at least 80% identity to SEQ ID NO: 6, preferably at least 85% identity, more preferably 90% or 95% identity and/or CDR3beta comprising or consisting of an amino acid sequence having at least 80% identity to SEQ ID NO: 7, preferably at least 85% identity, more preferably 90% or 95% identity, provided that the TCR retains the advantageous capabilities of the TCR evaluated in the appended examples, i.e. is capable of binding to the antigenic target specified herein.

The term "T cell receptor" or "TCR" as used herein includes in all grammatical forms native TCRs as well as TCR variants, fragments and constructs. The term thus includes heterodimers comprising TCR alpha and beta chains as well as multimers and single chain constructs; optionally comprising further domains and/or moieties.

In its native form, the TCR exists as a complex of several proteins on the surface of T cells. The T cell receptor is composed of two (separate) protein chains, which are produced from the independent T cell receptor alpha and beta (TCR $\alpha$ and TCR $\beta$) genes and are called alpha ($\alpha$-) and beta ($\beta$-) chains. Each chain of the TCR possesses one N-terminal immunoglobulin-like (Ig)-variable (V) domain/region, one Ig-constant-like (C) domain/region, a transmembrane/cell membrane-spanning region anchoring the chain in the plasma membrane, and a short cytoplasmic tail at the C-terminal end.

Antigen specificity is conferred by the variable regions of the alpha and beta chain. Both variable domains of the TCR alpha chain and beta chain comprise three hypervariable or complementarity determining regions (CDR1alpha/beta, CDR2alpha/beta and CDR3alpha/beta) surrounded by framework (FR) regions. CDR3 is the prime determinant of antigen recognition and specificity (i.e. the ability to recognize and interact with a specific antigen), whereas CDR1 and CDR2 mainly interact with the MHC molecule presenting the antigenic peptide.

The TCR provided herein is capable of recognizing and specifically recognizing PRAME, in particular PRAME in its MHC bound form as will be discussed somewhere else herein in detail. An antigenic peptide is said to be present in its "MHC bound form" when it forms a complex with an MHC molecule (which may be present on the surface of an antigen presenting cell such as a dendritic cell or a tumor cell, or it may be immobilized by for example coating to a bead or plate.).

Native TCRs recognize antigenic peptides bound to ("presented/displayed on") the major histocompatibility complex (MHC) molecules at the surface of an antigen presenting cell. An antigenic peptide presented on a MHC molecule is also referred to as a "peptide:MHC complex" herein. There are two different classes of MHC molecules: MHC I and MHC II, which present peptides from different cell compartments. MHC class I molecules are expressed on the surface of all nucleated cells throughout the human body and display peptide or protein fragments from intracellular compartments to cytotoxic T cells. In humans, the MHC is also called the human leukocyte antigen (HLA). There are three major types of MHC class I: HLA-A, HLA-B and HLA-C. Once a TCR binds to its specific peptide:MHC complex, the T cell is activated and exerts biological effector functions.

The terms "binding to" and "recognizing" in all grammatical forms are used interchangeably herein. The antigenic target is particularly envisaged to be recognized by the inventive TCR when being bound by an MHC class I molecule, specifically an HLA-A molecule, preferably an HLA-A*02 molecule. In particular the antigenic target is recognized by the TCR of the present invention when presented by an HLA-molecule encoded by the HLA-A*02: 01, HLA-A*02:02 or HLA-A*02:04 allele. Said MHC molecules, i.e. encoded by the HLA-A*02:01, HLA-A*02:02 and HLA-A*02:04 alleles, can be presented on the surface of a cell, for instance the surface of a tumor cell, or on a (solid) carrier. In the context of the present invention, the PRAME$_{SLL}$ peptide is particularly envisaged to be recognized by the inventive TCR when being bound by HLA-A2 which is a HLA-A*02:01, HLA-A*02:02, or HLA-A*02:04 encoded molecule. In a preferred embodiment of the invention, the TCR can specifically recognized PRAME$_{SLL}$ peptide when bound by HLA-A*02:01, HLA-A*02:02 and HLA-A*02:04 encoded molecules, i.e. is capable of binding all three HLA-A*02 allele encoded molecules. That means, the TCR of the present invention is capable of binding to each of the molecules encoded by the HLA alleles HLA-A*02:01, HLA-A*02:02 and HLA-A*02:04. It is however not envisaged that all HLA-A2 molecules are recognized at the same time in one patient, but are to be understood as alternatives.

CDR1 and CDR2 Domains

As noted previously, CDR1 and CDR2 of the TCR alpha and beta chains are thought to be mainly involved in MHC recognition. There is a limited "pool" of CDR1 and CDR2 sequences known to be involved in HLA-A*02-restricted antigen recognition, and it is envisaged that the CDR3 domains of the present invention can in principle be combined with any of the CDR1 and CDR2 domains depicted in SEQ ID NO: 2 to 5, provided that the TCR retains its ability to recognize its antigenic target, preferably in its HLA-A*02

(HLA-A*02:01, HLA-A*02:02 and HLA-A*02:04) bound form, to a similar, the same or even a higher extent as the TCR 3825 evaluated in the examples. Useful examples of CDR1 and CDR2 domains include the CDR1 alpha comprising or consisting of the sequence as depicted in SEQ ID NO: 2, the CDR2 alpha comprising or consisting of the sequence as depicted in SEQ ID NO: 4, the CDR1 beta comprising or consisting of the sequence as depicted in SEQ ID NO: 3, and the CDR2 beta comprising or consisting of the sequence as depicted in SEQ ID NO: 5. Said CDR sequences are also shown in Table 1.

In accordance with the foregoing, the present invention inter alia provides a TCR comprising two polypeptide chains, each of which comprises a human variable region comprising at least one complementarity determining region (i.e. in particular CDR3, and preferably a CDR1, and/or CDR2) of a TCR. A TCR with particular advantageous properties (as shown in the appended examples) comprises a first polypeptide chain comprising a CDR1 comprising or consisting of the amino acid sequence of SEQ ID NO: 2 (CDR1 alpha), a CDR2 comprising or consisting of the amino acid sequence of SEQ ID NO: 4 (CDR2 alpha), and a CDR3 comprising or consisting of the amino acid sequence of SEQ ID NO: 6 (CDR3 alpha), and/or a second polypeptide chain comprising a CDR1 comprising or consisting of the amino acid sequence of SEQ ID NO: 3 (CDR1 beta), a CDR2 comprising or consisting of the amino acid sequence of SEQ ID NO: 5 (CDR2 beta), and a CDR3 comprising or consisting of the amino acid sequence of SEQ ID NO: 7 (CDR3 beta).

Further envisaged are TCR sequence variants of the TCR of the present invention comprising a CDR1 alpha comprising or consisting of an amino acid sequence having at least about 60% identity to SEQ ID NO: 2, preferably at least 80% identity to SEQ ID NO: 2 and/or a CDR1 beta comprising or consisting of an amino acid sequence having at least about 60% identity to SEQ ID NO: 3, preferably at least 80% identity to SEQ ID NO: 3, provided that the TCR retains the advantageous capabilities of the TCR evaluated in the appended examples, i.e. is capable of binding to the antigenic target specified herein. Further envisaged are TCR sequence variants of the TCR of the present invention comprising a CDR2 alpha comprising or consisting of an amino acid sequence having at least about 70% identity to SEQ ID NO: 4, preferably at least 85% identity to SEQ ID NO: 4 and/or a CDR2 beta comprising or consisting of an amino acid sequence having at least about 65% identity to SEQ ID NO: 5, preferably at least 80% identity to SEQ ID NO: 5, provided that the TCR retains the advantageous capabilities of the TCR evaluated in the appended examples, i.e. is capable of binding to the antigenic target specified herein.

Complete Variable Regions

The present invention further provides a TCR comprising a TCR alpha chain variable region comprising or consisting of an amino acid sequence as depicted in SEQ ID NO: 8 and/or a TCR beta chain variable region comprising or consisting of an amino acid sequence as depicted in SEQ ID NO: 9. Said alpha and beta chain sequences are also shown in Table 1.

TCR sequence variants comprising alpha chain variable regions comprising an amino acid sequence having at least 80% identity, more preferably at least 85% identity, more preferably 90% or 95% to SEQ ID NO: 8 and/or a TCR beta chain variable region comprising or consisting of an amino acid sequence having at least 80% identity, more preferably at least 85% identity, more preferably 90% or 95% to SEQ ID NO: 9 are also envisaged herein; provided that the TCR retains the advantageous capabilities of the TCR evaluated in the appended examples, i.e. is capable of binding to the antigenic target specified herein.

Constant Region

The TCR of the present invention comprises an alpha chain constant region and/or a TCR beta chain constant region. The constant region can be a human constant region or derived from another species, yielding a "chimeric" TCR. For instance, human alpha and/or beta chains can be replaced by their murine counterparts ("murinization") which has been found to enhance surface expression of human TCRs by supporting preferential pairing of the TCR alpha and beta chains, and a more stable association with the CD3 co-receptor. Suitable constant regions of the alpha chain can for instance be selected from SEQ ID NOs: 26 (human), 29 (minimal murinized) and 31 (murine). Suitable constant regions of the beta chain can be selected from SEQ ID NOs: 27 (human), 28 (human), 30 (minimal murinized) and 32 (murine). The TCR beta constant region depicted in SEQ ID NOs: 27 and 28 are two human sequences which differ in a few amino acids. They are to be understood as alternatives. Instead of replacing complete human constant regions by their murine counterparts, it is also possible to exchange only some amino acids in the human constant regions for the corresponding amino acids of the murine constant region ("minimal murinization"), as further explained in the section "TCR sequence variants" herein. Further it is envisaged by the present invention that constant and variable regions can be combined in way suitable for the purpose. In this scenario the constant and variable regions may be derived from human, mouse or achieved by the process of minimal murinization as described above.

Alpha and Beta Chains

Useful examples of the TCR of the invention include those comprising an alpha chain comprising or consisting of an amino acid sequence as depicted in SEQ ID NO: 10 and/or a beta chain comprising or consisting of an amino acid sequence as depicted in SEQ ID NO: 11.

TCR sequence variants comprising alpha chains comprising an amino acid sequence having at least 80% identity, more preferably at least 85% identity, more preferably 90% or 95% to SEQ ID NO: 10 and/or a TCR beta chain comprising or consisting of an amino acid sequence having at least 80% identity, more preferably at least 85% identity, more preferably 90% or 95% to SEQ ID NO: 11 are also envisaged herein; provided that the TCR retains the advantageous capabilities of the TCR evaluated in the appended examples, i.e. is capable of binding to the antigenic target specified herein.

Antigenic Target

The TCR provided herein is advantageously capable of binding to (human) PRAME (SEQ ID NO: 1) also called PRAME$_{SLL}$. Hence, said TCRs are specific for PRAME peptide as depicted in SEQ ID NO: 1, also called PRAME$_{SLL}$. The term "specific for" in the context of the present invention means that the TCR is specifically binding to the target. PRAME (Preferentially Expressed Antigen in Melanoma. Uniprot Acc. No. P78395), also referred to as MAPE (melanoma antigen preferentially expressed in tumors) and OIP4 (OPA-interacting protein 4), has been reported a cancer-testis antigen (CTA) with unknown function. PRAME is a Protein Coding gene, associated with Melanoma and Leukemia, and Chronic Myeloid. Gene Ontology (GO) annotations related to this gene include retinoic acid receptor binding. The PRAME protein functions as a transcriptional repressor, inhibiting the signaling of retinoic acid through the retinoic acid receptors RARA, RARB and RARG. It prevents retinoic acid-induced arrest of cell proliferation, differentiation and apoptosis.

Preferably, the inventive TCR specifically binds to its antigenic target. In particular, the present invention provides a TCR that is capable of binding a peptide comprised within the PRAME amino acid sequence as depicted in SEQ ID NO: 1 (see Table 1). The term "capable of binding" means that said peptide is specifically bound by said TCR. The term "specific(ally) binding" generally indicates that a TCR binds via its antigen binding site more readily to its intended antigenic target than to a random, unrelated non-target antigen. Particularly the term "specifically binds" indicates that the binding specificity of the TCR will be at least about 5-fold, preferably 10-fold, more preferably 25-fold, even more preferably 50-fold, and most preferably 100-fold or more, greater for its antigenic target than its binding specificity for a non-target antigen. The PRAME peptide consisting of the amino acid sequence as depicted in SEQ ID NO: 1 is also referred to as "antigenic target" or "SLL peptide" herein. Hence, the PRAME peptide consisting of the amino acid sequence as depicted in SEQ ID NO: 1 is or comprises the targeted epitope of the TCR of the present invention.

The term "epitope" in general refers to a site on an antigen, typically a (poly-) peptide, which a binding domain recognizes. The term "binding domain" in its broadest sense refers to an "antigen binding site", i.e. characterizes a domain of a molecule which binds/interacts with a specific epitope on an antigenic target. An antigenic target may comprise a single epitope, but typically comprises at least two epitopes, and can include any number of epitopes depending on the size, conformation, and type of antigen. The term "epitope" in general encompasses linear epitopes and conformational epitopes. Linear epitopes are contiguous epitopes comprised in the amino acid primary sequence and typically include at least 2 amino acids or more. Conformational epitopes are formed by non-contiguous amino acids juxtaposed by folding of the target antigen, and in particular target (poly-) peptide.

The present inventors have found that the minimal amino acid sequence recognized by the TCR of the invention corresponds to the amino acid sequence of PRAME (SEQ ID NO: 1). Specifically, the inventive TCR has been shown to (specifically) recognize the amino acid sequence comprising or consisting of the amino acid sequence SLLQH-LIGL (SEQ ID NO: 1), or its HLA-A2 bound form as shown in the appended examples. This selective recognition can be obtained by the recognition motif of the T cell receptor, displaying only a few fixed positions (FIG. 3). The amino acids LLQ and especially HLI of the sequence SLLQHLIGL (SEQ ID NO: 1) are part of this recognition motif. Specifically, the TCR described herein is envisaged to recognize at least one epitope within the aforementioned amino acid sequences. Further, the TCRs of the present invention have a recognition motif which differs markedly from the recognition pattern of other TCRs known in the art (FIG. 12).

A native TCR as described herein is envisaged to bind to its antigenic target (i.e. preferably PRAME presented on HLA-A*02:01-, HLA-A*02:02- or HLA-A*02:04-encoded molecules by antigen presenting cells) with a high functional avidity. The term "functional avidity" refers to the capability of TCR expressing cells (in particular T cells expressing native TCRs as described herein) to respond in vitro to a given concentration of a ligand, and is thought to correlate with the in vivo effector capacity of TCR expressing cells. By definition, TCR expressing cells with high functional avidity respond in in vitro tests to very low antigen doses, while such cells of lower functional avidity require higher amounts of antigen before they mount an immune response similar to that of high-avidity TCR expressing cells. The functional avidity can be therefore considered as a quantitative determinant of the activation threshold of a TCR expressing cell. It is determined by exposing such cells in vitro to different amounts of cognate antigen. TCR expressing cells with high functional avidity respond to low antigen doses.

For example, a TCR expressing cell will typically be considered to bind with "high" functional avidity to its antigenic target if it secretes at least about 200 pg/mL or more (e.g. 200 pg/mL or more, 300 pg/mL or more, 400 pg/mL or more, 500 pg/mL or more, 600 pg/mL or more, 700 pg/mL or more, 1000 pg/mL or more, 5,000 pg/mL or more, 7,000 pg/mL or more, 10,000 pg/mL or more, or 20,000 pg/mL or more) of interferon gamma (IFN-gamma) upon co-culture with antigen-negative HLA-A2 expressing target cells loaded with a low concentration of the PRAME peptide ranging from about $10^{-5}$ to about $10^{-11}$ M (i.e. about 0.05 ng/mL to about 5 ng/mL, 0.05 ng/mL, 0.1 ng/mL, 0.5 ng/mL, 1 ng/mL, or 5 ng/mL) with a molecular weight of the PRAME peptide of 956 g/mol. Hence, the TCR of the present invention is a high-avidity TCR causing a half-maximal relative IFN-gamma secretion ($EC_{50}$ value) of less than $10^{-7}$ M, as measured by an IFN-gamma immunoassay. Preferably, the caused half-maximal relative IFN-gamma secretion ($EC_{50}$ value) is less than $10^{-8}$ M, as measured by an IFN-gamma immunoassay (FIG. 2). The high-avidity of the TCRs of the present invention have further been proven in comparison to other TCRs disclosed in the art by determining the $EC_{50}$ values of each TCR (FIG. 13).

It is encompassed by the present invention that the binding to the sequence SLLQHLIGL (SEQ ID NO: 1) or a portion thereof, or its HLA-A2 bound form induces IFN-gamma secretion by cells transduced or transfected with the TCR. The IFN-gamma secretion induced by binding of the inventive TCR expressed on an effector cell to the amino acid sequence of SEQ ID NO: 1, which is presented by an HLA-A*02:01-, HLA-A*02:02- or HLA-A*02:04-encoded molecule, may be more than 100 times higher, preferably 500 times higher, more preferably 2000 times higher when binding to the amino acid sequence of SEQ ID NO: 1, which is presented by the HLA-A*02:01-, HLA-A*02:02- or HLA-A*02:04-encoded molecule, compared to binding to an irrelevant peptide (amino acid sequence GLSNTHVL, depicted in SEQ ID NO: 25), which is presented by the HLA-A*02:01-, HLA-A*02:02- or HLA-A*02:04-encoded molecule. The IFN-gamma secretion may be for example more than 100 pg/ml, such as more than 500 pg/ml or more than 2000 pg/ml.

The cytokine release, such as IFN-gamma secretion, may be measured using an in vitro assay in which K562 cells (Greiner et al., 2006, Blood. 2006 Dec. 15; 108(13):4109-17) are transfected with MRNA or transduced to express the amino acid sequence of SEQ ID NOs: 1 or irrelevant peptide, respectively, and are incubated with CD8$^+$ enriched and/or non-CD8$^+$-enriched PBMC expressing the TCR to be investigated or in an in vitro assay using T2 cells externally loaded with either the SEQ ID NO: 1 or the irrelevant peptide and subsequently co-incubated with CD8$^+$ enriched and/or non-CD8$^+$-enriched PBMC expressing the TCR to be investigated.

Some embodiments refer to an isolated TCR as described herein, polypeptide as described herein or multivalent TCR complex as described herein, wherein IFN-gamma secretion induced by binding of the inventive TCR expressed on an effector cell to the amino acid sequence of SEQ ID NO: 1 or in particular to the amino acid sequence of SEQ ID NO: 1 which is presented by an HLA-A*02:01-, HLA-A*02:02- or HLA-A*02:04-encoded molecule is below a predefined threshold. The threshold may be determined by using a specific Effector to Target ratio of at least 2:1. The "effector cell" may be a peripheral blood lymphocyte (PBL) or a peripheral blood mononuclear cell (PBMC). Typically, the effector cell is an immune effector cell, such as a T cell. Particular suitable effector cells include cytotoxic T lymphocytes (CTLs), CD8+ T cells, CD4+ T cells, natural killer (NK) cells, natural killer T (NKT) cells, gamma/delta-T cells as described elsewhere herein.

The IFN-gamma secretion upon binding of the inventive TCR expressed on an effector cell to amino acid sequence of SEQ ID NO: 1 which is presented by an HLA-A*02:01-, HLA-A*02:02- or HLA-A*02:04-encoded molecule may be induced at a PRAME$_{SLL}$ peptide concentration of at least $10^{-7}$ M, preferably at least $10^{-8}$ M, more preferably $10^{-9}$ M. In specific embodiments, for example when the ratio of TCR-transgenic T cells to T2 cells is 2:1, the IFN-gamma secretion upon by binding of the inventive TCR expressed on an effector cell to amino acid sequence of SEQ ID NO: 1 which is presented by the HLA-A*02:01-encoded molecule may be induced at a PRAME$_{SLL}$ peptide concentration of at least $10^{-7}$ M, preferably at least $10^{-8}$ M, more preferably $10^{-9}$ M. Other methods to determine specific binding of the inventive TCR include the <51>Cr-release assay described by Gertner-Dardenne et al., J Immunol 188(9): 4701-4708, CD107a/b mobilization described by Leisegang et al., Clin. Cancer Res 2010. 16: 2333-2343 and peptide: MHC multimer binding analyses described by Wilde et al., J Immunol 2012; 189:598-605.

Variants

As noted previously, the term "TCR" encompasses TCR variants, which include TCR sequence variants, fragments and constructs. All TCR variants are envisaged to be functional variants of the inventive TCR. The term "functional variant" as used herein refers to a TCR, polypeptide, or protein having substantial or significant sequence identity or similarity to a parent TCR, its variable regions or its antigen-binding regions and shares its biological activity, i.e. its ability to specifically bind to the antigenic target for which the parent TCR of the invention has antigenic specificity to a similar, the same or even a higher extent as the TCR disclosed herein and evaluated in the appended examples. Also encompassed by the present invention are TCR sequence variants.

The term "TCR variants" includes "sequence variants" of the TCR disclosed herein, i.e. variants substantially comprising the amino acid sequence of the inventive TCR as described above (also referred to as the "parent" TCR) but containing at least one amino acid modification (i.e. a substitution, deletion, or insertion) as compared to the "parent" TCR amino acid sequence, provided that the variant preferably retains the antigenic specificity of the inventive "parent" TCR. TCR sequence variants of the invention are typically prepared by introducing appropriate nucleotide changes into the nucleic acids encoding the "parent" TCR, or by peptide synthesis. Generally, the aforementioned amino acid modifications may be introduced into, or present in, the variable region or the constant region of the TCR, and may serve to modulate properties like binding strength and specificity, post-translational processing (e.g. glycosylation), thermodynamic stability, solubility, surface expression or TCR assembly.

As set out previously, amino acid modifications include, for example, deletions from, and/or insertions into, and/or substitutions of, residues within the amino acid sequences of the parent TCR. Exemplary insertional variants of a TCR of the invention include fusion products of said TCR and an enzyme or another functional polypeptide. Exemplary substitutional variants of a TCR of the invention are those including amino acid substitutions in variable regions or CDRs of the alpha and/or beta chain, the framework region or the constant region. Particularly envisaged herein are conservative amino acid substitutions. Conservative amino acid substitutions are known in the art, and include amino acid substitutions in which one amino acid having certain physical and/or chemical properties is exchanged for another amino acid that has the same chemical or physical properties. For instance, the conservative amino acid substitution can be in an acidic amino acid substituted for another acidic amino acid (e.g. Asp or Glu), an amino acid with a nonpolar side chain substituted for another amino acid with a non-polar side chain (e.g. Ala, Gly, Val, He, Leu, Met, Phe, Pro, Trp, Val, etc.), a basic amino acid substituted for another basic amino acid (Lys, Arg, etc.), an amino acid with a polar side chain substituted for another amino acid with a polar side chain (Asn, Cys, Gin, Ser, Thr, Tyr, etc.), etc. that may be made, for instance, on the basis of similarity in polarity, charge, solubility, hydrophobicity, hydrophilicity, and/or the amphipathic nature of the residues involved.

In general, TCR sequence variants are envisaged to comprise at least one of the CDR1, CDR2, CDR3, alpha chain variable regions, beta chain variable regions, alpha chains and/or beta chains as disclosed herein, or comprising or consisting of an amino acid sequence that is at least about 80%, about 85%, about 90%, about 95%, about 96%, about 97%, about 98%, about 99%, or identical to the amino acid sequences disclosed herein, provided that said variants exhibit comparable, the same or improved binding characteristics as compared to TCR evaluated in the appended examples.

As used herein the term "sequence identity" indicates the extent to which two (nucleotide or amino acid) sequences have identical residues at the same positions in an alignment, and is often expressed as a percentage. Preferably, identity is determined over the entire length of the sequences being compared. Thus, two copies of exactly the same sequence have 100% identity, but sequences that are less highly conserved and have deletions, additions, or replacements, may have a lower degree of identity. Those skilled in the art will recognize that several algorithms are available for determining sequence identity using standard parameters, for example Blast (Altschul et al., (1997) Nucleic Acids Res. 25:3389-3402), Blast2 (Altschul et al., (1990) J. Mol. Biol. 215:403-410), Smith-Waterman (Smith et al., (1981) J. Mol. Biol. 147:195-197) and ClustalW.

Accordingly, the amino acid sequences of SEQ ID NOs: 10 or 11, can for instance serve as "subject sequence" or "reference sequence", while the amino acid sequence of a CDR3 different therefrom can serve as "query sequence".

The term "position" when used in accordance with the disclosure means the position of either an amino acid within an amino acid sequence depicted herein or the position of a nucleotide within a nucleic acid sequence depicted herein. The term 'corresponding' as used herein also includes that a position is not only determined by the number of the preceding nucleotides/amino acids, but is rather to be viewed in the context of the circumjacent portion of the sequence. Accordingly, the position of a given amino acid or nucleotide in accordance with the disclosure may vary due to deletion or addition of amino acids or nucleotides elsewhere in the sequence. Thus when a position is referred to as a "corresponding position", in accordance with the disclosure it is understood that nucleotides/amino acids may differ in terms of the specified numeral but may still have similar neighboring nucleotides/amino acids. In order to determine whether an amino acid residue (or nucleotide) in a given sequence corresponds to a certain position in the amino acid sequence of a "parent" amino acid/nucleotide sequence, the skilled person can use means and methods well-known in the art, e.g. sequence alignments, either manually or by using computer programs such as exemplified herein.

A TCR variant used herein as control is the TCR receptor 3825. This variant is based on a PRAME immunized mouse (mouse ID 3825) which expressed a TCR receptor against PRAME, with the CDR3 alpha sequence as depicted in the SEQ ID NO: 23 (CAVEPGGSYIPTF), CDR3 beta sequence as depicted in the SEQ ID NO: 24 (CASSPGLSYEQYF). Through a TCR library with codon optimized oligonucleotides this TCR could be recombinantly expressed and analysed (Weis, Manon (2015): Charakterisierung Antigenspezifischer T-Zellen nach Induktion in TCR-humanisierten Mäusen. Dissertation, LMU München Tierärztliche Fakultät: Veterinary Faculty Ludwigs University of Munich).

Cysteine Modification

The addition of a disulfide bond in the constant region has been reported to foster correct pairing of the TCR alpha and beta chains (Kuball J et al., Blood. 2007 Mar. 15; 109(6): 2331-8.). Thus, the addition of one or more cysteine bonds in the constant region is also envisaged herein.

Murinization

As noted previously, murinization of TCRs (i.e. exchanging the human constant regions in the alpha and beta chain by their murine counterparts) is a technique that is commonly applied in order to improve cell surface expression of TCRs in host cells. Without wishing to be bound by specific theory, it is thought that murinized TCRs associate more effectively with CD3 co-receptors; and/or that preferentially pair with each other and are less prone to form mixed TCRs on human T cells engineered ex vivo to express the TCRs of desired antigenic specificity, but still retaining and expressing their "original" TCRs.

Recently nine amino acids responsible for the improved expression of murinized TCRs have been identified (Sommermeyer and Uckert, J Immunol. 2010 Jun. 1; 184(11): 6223-31) and it is envisaged to substitute one or all of the amino acid residues in the TCRs alpha and//or beta chain constant region for their murine counterpart residues. This technique is also referred to as "minimal murinization", and offers the advantage of enhancing cell surface expression while, at the same time, reducing the number of "foreign" amino acid residues in the amino acid sequence and, thereby, the risk of immunogenicity.

Constructs and Fragments

The term "TCR" as used herein further comprises TCR constructs. The term "construct" includes proteins or polypeptides comprising at least one antigen binding domain of the inventive TCR, but do not necessarily share the basic structure of a native TCR (i.e. variable domains incorporated into a TCR alpha chain and a TCR beta chain forming a heterodimer). TCR constructs and fragments are typically obtained by routine methods of genetic engineering and are often artificially constructed to comprise additional functional protein or polypeptide domains. In accordance with the foregoing, TCR constructs and fragments of the invention are envisaged to comprise at least one CDR3 alpha and/or at least one CDR3 beta as disclosed elsewhere herein. Further envisaged herein are constructs and fragments comprising at least one CDR1 alpha, CDR2 alpha, CDR1 beta, CDR2 beta, alpha chain variable region, beta chain variable region, alpha chain and/or beta chain, or combinations thereof, optionally in combination with further protein domains or moieties as exemplified herein. The TCR constructs and fragments provided herein are envisaged to be capable of specifically binding to the same antigenic target as the inventive TCR described above and evaluated in the appended Examples.

Multimers

The TCR construct of the present invention encompasses heterodimers and multimers in which at least one TCR alpha chain variable region or TCR alpha chain and at least one TCR beta chain variable region are covalently linked to each other to form TCR heterodimers or multimers. A "multimer" as used in the present invention describes a molecule of diverse subunits or functional entities while a heterodimer comprises only two functional entities. In its simplest form a multivalent TCR construct according to the invention comprises a multimer of two or three or four or more TCRs associated (e.g. covalently or otherwise linked) with one another, preferably via a linker molecule. In this context "covalently linked" means a chemical bond between two molecules, sharing electron pairs describing a stable balance between atom bonds.

Suitable linker to a spherical body, preferably a uniform bead, more preferably a polystyrene bead, most preferably a bio-compatible polystyrene bead. Such TCR constructs can also be comprised of an inventive TCR and a bead having a pre-defined fluorescence dye incorporated into the bead. Suitable linker molecules include, but are not limited to, multivalent attachment molecules such as avidin, streptavidin, neutravidin and extravidin, each of which has four binding sites for biotin. Thus, biotinylated TCRs can be formed into multimers having a plurality of TCR binding sites. The number of TCRs in the multimer will depend upon the quantity of TCR in relation to the quantity of linker molecule used to make the multimers, and also on the presence or absence of any other biotinylated molecules. Exemplary multimers are dimeric, trimeric, tetrameric or pentameric or higher-order multimer TCR constructs. Multimers of the invention may also comprise further functional entities such as labels or drugs or (solid) carriers.

Fusion Proteins

A TCR heterodimer or multimer also relates to fusion proteins or polypeptides comprising at least one TCR alpha chain, TCR alpha chain variable region or CDR3 alpha and/or at least one TCR beta chain, TCR beta chain variable region or CDR3 beta; and further one or more fusion component(s). It may be at least one TCR alpha chain as defined herein and/or at least one TCR beta chain as defined herein and/or an antibody or a single chain antibody fragment (scFv) which is directed against an antigen or epitope on the surface of lymphocytes, and also the TCR alpha chain(s) and TCR beta chain(s) are linked to each other and fused, optionally via a linker, to said antibody or scFv. Useful components include Fc receptors; Fc domains (derived from IgA, IgD, IgG, IgE, and IgM); cytokines (such as IL-2 or IL-15); toxins; antibodies or antigen-binding fragments thereof (such as anti-CD3, anti-CD28, anti-CD5, anti-CD16 or anti-CD56 antibodies or antigen-binding fragments thereof); CD247 (CD3-zeta), CD28, CD137, CD134 domains; or any combinations thereof.

Exemplary antibody fragments that can be used as fusion components include fragments of full-length antibodies, such as (s)dAb, Fv, Fd, Fab, Fab', F(ab')2 or "r IgG" ("half antibody"); modified antibody fragments such as scFv, di-scFv or bi(s)-scFv, scFv-Fc, scFv-zipper, scFab, Fab2, Fab3, diabodies, single chain diabodies, tandem diabodies (Tandab's), tandem di-scFv, tandem tri-scFv, minibodies, multibodies such as triabodies or tetrabodies, and single domain antibodies such as nanobodies or single variable domain antibodies comprising only one variable domain, which might be VHH, VH or VL.

TCR constructs of the invention may be fused to one or more antibody or antibody fragments, yielding monovalent, bivalent and polyvalent/multivalent constructs and thus monospecific constructs, specifically binding to only one target antigen as well as bispecific and polyspecific/multispecific constructs, which specifically bind more than one target antigens, e.g. two, three or more, through distinct antigen binding sites.

Optionally, a linker may be introduced between the one or more of the domains or regions of the TCR construct of the invention, i.e. between the TCR alpha chain CDR3, TCR alpha chain variable region, and/or a TCR alpha chain, the TCR beta chain CDR3, TCR beta chain variable region, and/or a TCR beta chain, and/or the one or more fusion component(s) described herein. Linkers are known in the art and have been reviewed, inter alia, by Chen et al., Adv Drug Deliv Rev. 2013 Oct. 15; 65(10): 1357-1369. In general, linkers include flexible, cleavable and rigid linkers and will be selected depending on the type of construct and intended use/application. For example, for therapeutic application, non-immunogenic, flexible linkers are often preferred in order to ensure a certain degree of flexibility or interaction between the domains while reducing the risk of adverse immunogenic reactions. Such linkers are generally composed of small, non-polar (e.g. Gly) or polar (e.g. Ser or Thr) amino acids and include "GS" linkers consisting of stretches of Gly and Ser residues.

Particularly useful TCR constructs envisaged in accordance with the invention are those comprising at least one TCR alpha chain, TCR alpha chain variable region or CDR3 alpha as defined herein, at least one TCR beta chain, TCR beta chain variable region or CDR3 beta as defined herein, optionally linked to each other and fused, optionally via a liker, to at least one antibody or an antibody fragment (such as a single chain antibody fragment (scFv)) directed against an antigen or epitope on the surface of lymphocytes. Useful antigenic targets recognized by the antibody or antibody fragment (e.g. scFv) include CD3, CD28, CD5, CD16 and CD56. Said construct can in general have any structure as long the "TCR portion" (i.e. TCR alpha and beta chain or variable regions or CDR3s thereof) retains its ability to recognize the antigenic target defined herein, and the "antibody portion" binds to the desired surface antigen or epitope, thereby recruiting and targeting the respective lymphocyte to the target cell. Such constructs may advantageously serve as "adapters" joining an antigen presenting cell displaying the antigenic target (such as a tumor cell) and a lymphocyte (such as a cytotoxic T cell or NK cell) together. An example of such a fusion protein is a construct engineered according to the principle of a bi-specific T cell engager (BiTE®) consisting of two single-chain variable fragments (scFvs) of different antibodies, on a single peptide chain of about 55 kilodaltons (kDa). Accordingly, a TCR construct of the invention may comprise at least one TCR antigen binding domain as described herein (for instance a TCR variable alpha and variable beta chain fused to each other) linked to a scFv (or other binding domain) of the desired binding specificity. e.g. CD3 or CD56. The scFv (or other binding domain) binds to T cells such as via the CD3 receptor or to CD56 for NK cell activation, and the other to a tumor cell via an antigenic target specifically expressed on the tumor cell. Also envisaged herein are tribodies comprising at least one TCR antigen binding domain as described herein, an scFv (or other binding domain) and a further domain e.g. for targeting the construct to a site of action within the body (e.g. an Fc domain).

Isolated Form

The TCR of the invention may be provided in "isolated" or "substantially pure" form. "Isolated" or "substantially pure" when used herein means that the TCR has been identified separated and/or recovered from a component of its production environment, such that the "isolated" TCR is free or substantially free of other contaminant components from its production environment that might interfere with its therapeutic or diagnostic use. Contaminant components may include enzymes, hormones, and other proteinaceous or non-proteinaceous solutes. "Isolated" TCRs will thus be prepared by a method for obtaining a TCR through incubating a host cell under conditions causing expression of said TCR, and purifying said TCR thus containing at least one purification step removing or substantially removing these contaminant components. The aforementioned definition is equally applicable to "isolated" polynucleotides/nucleic acids, mutatis mutandis.

Soluble Forms

The TCR of the present invention can be provided in soluble form. Soluble TCRs are useful as diagnostic tools, and carriers or "adapters" that specifically target therapeutic agents or effector cells to, for instance, a cancer cell expressing the antigenic target recognized by the soluble TCR. Soluble TCRs (sTCRs) will typically be fragments or constructs comprising TCR alpha and/or beta chains, or variable regions or CDRs thereof and optionally stabilized via disulfide bonds or covalently linked via a suitable linker molecule, e.g. as described above in the context of TCR constructs of the invention. They will typically not comprise e.g. a transmembrane region. In some circumstances amino acid modifications in the polypeptide sequence may be introduced in order to enhance solubility of the molecules, and/or correct folding and pairing of the alpha and beta chains (if desired), in particular when produced in a recombinant host that does not provide for the aforementioned features. When using E. coli as production host cells for instance folding and pairing of the TCR alpha and beta chains is typically accomplished in vitro. A TCR according to the invention may therefore for instance comprise additional cysteine residues, as described elsewhere herein.

Besides additional cysteine bridges, other useful modifications include, for instance, the addition of leucine zippers and/or ribosomal skipping sequences, e.g. sequence 2A from picorna virus as described in Walseng et al., (2015), PLoS ONE 10(4): e0119559 to increase folding, expression and/or pairing of the TCR alpha and/or beta chains.

Modifications

The TCR of the invention may further comprise one or more modifications as described in the following. The modifications described below will typically be covalent modifications and can be accomplished using standard techniques known in the art. In some circumstances, amino acid modifications in the TCRs may be required in order to facilitate the introduction of said modifications.

Molecular Markers

The TCR, in particular (soluble) TCR, of the invention can be labelled with at least one molecular marker. Useful molecular markers are known in the art and can be coupled to the TCR or TCR variant using routine methods, optionally via linkers of various lengths.

In general, different marker fall into a variety of classes, depending on the assay in which they are to be detected—the following examples include, but are not limited to: isotopic marker, which may be radioactive or heavy isotopes, such as radioisotopes or radionuclides (e.g. $<3>$H, $<14>$, $<15>$N, $<35>$S, $<89>$Zr, $<90>$Y, $<99>$Tc, $<111>$In, $<125>$I, $<131>$I); magnetic marker (e.g. magnetic particles); redox active moieties; optical dyes (including, but not limited to, chromophores, phosphors and fluorophores) such as fluorescent groups (e.g. FITC, rhodamine, lanthanide phosphors), chemiluminescent groups, and fluorophores which can be either "small molecule" fluorophores or proteinaceous fluorophores; enzymatic groups (e.g. horseradish peroxidase, β-galactosidase, luciferase, alkaline phosphatase; biotinylated groups; or predetermined polypeptide epitopes recognized by a secondary reporter (e.g. leucine zipper pair sequences, binding sites for secondary antibodies, metal binding domains, epitope tags, etc.). Labelling with molecular markers is particularly envisaged when the TCR, TCR variants or especially soluble TCR constructs (such as those comprising at least one TCR alpha and/or TCR beta chain as described herein) are intended for diagnostic use.

Functional Moieties

The TCR, in particular soluble TCR, of the invention can be modified by attaching further functional moieties, e.g. for reducing immunogenicity, increasing hydrodynamic size (size in solution) solubility and/or stability (e.g. by enhanced protection to proteolytic degradation) and/or extending serum half-life.

Exemplary functional moieties for use in accordance with the invention include peptides or protein domains binding to other proteins in the human body (such as serum albumin, the immunoglobulin Fc region or the neonatal Fc receptor (FcRn), polypeptide chains of varying length (e.g. XTEN technology or PASylation®), non-proteinaceous polymers, including, but not limited to, various polyols such as polyethylene glycol (PEGylation), polypropylene glycol, polyoxyalkylenes, or copolymers of polyethylene glycol and polypropylene glycol, or of carbohydrates, such as hydroxyethyl starch (e.g. HESylation®) or polysialic acid (e.g. PolyXen® technology).

Other useful functional moieties include "suicide" or "safety switches" that can be used to shut off effector host cells carrying an inventive TCR in a patient's body. An example is the inducible Caspase 9 (iCasp9) "safety switch" described by Gargett and Brown Front Pharmacol. 2014; 5: 235. Briefly, effector host cells are modified by well-known methods to express a Caspase 9 domain whose dimerization depends on a small molecule dimerizer drug such as AP1903/CIP, and results in rapid induction of apoptosis in the modified effector cells. The system is for instance described in EP2173869 (A2). Examples for other "suicide" "safety switches" are known in the art, e.g. Herpes Simplex Virus thymidine kinase (HSV-TK), expression of CD20 and subsequent depletion using anti-CD20 antibody or myc tags (Kieback et al., Proc Natl Acad Sci USA. 2008 Jan. 15; 105(2):623-8). The inventive TCR can also be modified by introducing an inducible so called "on-switch" (as for example described in WO2019175209A1), wherein the modified alpha and beta chains of the inventive TCR only dimerize upon interaction with a small dimerizer drug subsequently resulting in a functional TCR which is only expressed on the cell surface in the presence of the dimerizer drug.

Glycosylation

TCRs with an altered glycosylation pattern are also envisaged herein. As known in the art, glycosylation patterns can depend on the amino acid sequence (e.g. the presence or absence of particular glycosylation amino acid residues, discussed below) and/or the host cell or organism in which the protein is produced. Glycosylation of polypeptides is typically either N-linked or O-linked. N-linked refers to the attachment of the carbohydrate moiety to the side chain of an asparagine residue. Addition of N-linked glycosylation sites to the binding molecule is conveniently accomplished by altering the amino acid sequence such that it contains one or more tri-peptide sequences selected from asparagine-X-serine and asparagine-X-threonine (where X is any amino acid except proline). O-linked glycosylation sites may be introduced by the addition of or substitution by, one or more serine or threonine residues to the starting sequence.

Another means of glycosylation of TCRs is by chemical or enzymatic coupling of glycosides to the protein. Depending on the coupling mode used, the sugar(s) may be attached to (a) arginine and histidine, (b) free carboxyl groups. (c) free sulfhydryl groups such as those of cysteine, (d) free hydroxyl groups such as those of serine, threonine, or hydroxyproline, (e) aromatic residues such as those of phenylalanine, tyrosine, or tryptophan, or (f) the amide group of glutamine.

Similarly, deglycosylation (i.e. removal of carbohydrate moieties present on the binding molecule) may be accomplished chemically, e.g. by exposing the TCRs to trifluoromethanesulfonic acid, or enzymatically by employing endo- and exo-glycosidases.

Drug Conjugates

It is also conceivable to add a drug such as a small molecule compound to the TCR, in particular to the soluble TCR of the present invention. Linkage can be achieved via covalent bonds, or non-covalent interactions such as through electrostatic forces. Various linkers, known in the art, can be employed in order to form the drug conjugates.

Tags

The TCR, in particular soluble TCR, of the disclosure can be modified to introduce additional domains which aid in identification, tracking, purification and/or isolation of the respective molecule (tags). Non-limiting examples of such tags comprise peptide motives known as Myc-tag, HAT-tag, HA-tag, TAP-tag, GST-tag, chitin binding domain (CBD-tag), maltose binding protein (MBP-tag), Flag-tag, Strep-tag and variants thereof (e.g. Strep II-tag), His-tag, CD20, Her2/neu tags, myo-tag, FLAG-tag, T7-tag, HA(hemagglutinin)-tag, or GFP-tags.

Epitope tags are useful examples of tags that can be incorporated into the TCR of the disclosure. Epitope tags are short stretches of amino acids that allow for binding of a specific antibody and therefore enable identification and tracking of the binding and movement of soluble TCRs or host cells within the patient's body or cultivated (host) cells. Detection of the epitope tag, and hence, the tagged TCR, can be achieved using a number of different techniques. Examples of such techniques include: immunohistochemistry, immunoprecipitation, flow cytometry, immunofluorescence microscopy, ELISA, immunoblotting ("Western"), and affinity chromatography. The epitope tags can for instance have a length of 6 to 15 amino acids, in particular 9 to 11 amino acids. It is also possible to include more than one epitope tag in the TCR of the invention.

Tags can further be employed for stimulation and expansion of host cells carrying an inventive TCR by cultivating the cells in the presence of binding molecules (antibodies) specific for said tag.

Nucleic Acid

The present invention further provides nucleic acids encoding the TCR described herein or a polynucleotide encoding a TCR as described herein. These nuclei acids are codon optimized, meaning one protein can be encoded by many alternative nucleic acid sequences which can be selected. Codon preference (codon usage bias) differs in each organism, and it can create challenges for expressing recombinant proteins in heterologous expression systems, resulting in low and unreliable expression. This may also be true for autologous expression, since wild type sequences are not necessarily optimized for expression yield but also for degradation, regulation, and other properties. Thus, codon optimization was used herein to provide an efficient protein expression. The following Table 1 indicates the nucleotide sequences encoding the respective amino acid sequences:

TABLE 1

| Name | SEQ ID NO. | |
|---|---|---|
| | | Nucleic acid sequence |
| PRAME epitope | SEQ ID NO: 12 | agcctgctgcagcatctgattggcctg |
| CDR1 alpha | SEQ ID NO: 13 | agcatatttaacacc |
| CDR1 beta | SEQ ID NO: 14 | tctggagacctctct |
| CDR2 alpha | SEQ ID NO: 15 | ttatataaggctggtgaattg |
| CDR2 beta | SEQ ID NO: 16 | tattataatggagaagag |
| CDR3 alpha | SEQ ID NO: 17 | tgtgctgggcttgctgattatggaggaagcc aaggaaatctcatcttt |
| CDR3 beta | SEQ ID NO: 18 | tgtgccagcagcgtatgggcctccggcggct acgagcagtacttc |
| TCR alpha variable region | SEQ ID NO: 19 | atgctgctggaacatctgctgatcatcctgt ggatgcagctgacctgggtttccggccagca gctgaatcagagccctcagagcatgttcatc caagaaggcgaggacgtttccatgaattgca ccagcagcagcatcttcaacacctggctgtg gtacaagcaggaccctggcgaaggaccagtg ctgctgatcgccttgtacaaagccggcgagc tgaccagcaacggcagactgacagcccagtt cggcattacccggaaggacagcttcctgaac atctccgccagcattccctccgacgtgggca tctatttttgtgcc |
| TCR beta variable region | SEQ ID NO: 20 | atgggcttcagactgctgtgctgcgtggcct tttgtctgcttggagccggacctgtggatag cggcgttacccagacacctaagcacctgatc acagccacaggccagcgcgtgaccctgagat gttctcctagaagcggcgacctgagcgtgta ctggtatcagcagtctctggaccagggcctg cagttcctgatccagtactacaacggcgagg aaagagccaagggcaacatcctggaacggtt cagcgcccagcagttcccagatctgcacagc gagctgaacctgagcagcctggaactgggag atagcgccctgtacttctgtgcctctagcgt g |

TABLE 1-continued

| Name | SEQ ID NO. | |
|---|---|---|
| TCR alpha chain (mmC) | SEQ ID NO: 21 | atgctgctggaacatctgctgatcatcctgt ggatgcagctgacctgggtttccggccagca gctgaatcagagccctcagagcatgttcatc caagaaggcgaggacgtttccatgaattgca ccagcagcagcatcttcaacacctggctgtg gtacaagcaggaccctggcgaaggaccagtg ctgctgatcgccttgtacaaagccggcgagc tgaccagcaacggcagactgacagcccagtt cggcattacccggaaggacagcttcctgaac atctccgccagcattccctccgacgtgggca tctatttttgtgccggcctggccggattacgg cggctctcagggaaatctgatcttcggcaag ggcaccaagctgagcgtgaagcccaacattc agaacccccgatcctgccgtgtaccagctgag agacagcaagagcagcgacaagagcgtgtgc ctgttcaccgacttcgacagccagaccaacg tgtcccagagcaaggacagcgacgtgtacat caccgacaagaccgtgctggacatgcgggagc atggacttcaagagcaacagcgccgtggcct ggtccaacaagagcgatttcgcctgcgccaa cgccttcaacaacagcattatccccgaggac acattcttccccagctccgatgtgccctgcg acgtgaagctggtggaaaagagcttcgagac agacaccaacctgaacttccagaacctgtcc gtgatcggcttcagaatcctgctgctgaagg tggccggcttcaacctgctgatgacactgag actgtggtccagc |
| TCR beta chain (mmC) | SEQ ID NO: 22 | atgggcttcagactgctgtgctgcgtggcct tttgtctgcttggagccggacctgtggatag cggcgttacccagacacctaagcacctgatc acagccacaggccagcgcgtgaccctgagat gttctcctagaagcggcgacctgagcgtgta ctggtatcagcagtctctggaccagggcctg cagttcctgatccagtactacaacggcgagg aaagagccaagggcaacatcctggaacggtt cagcgcccagcagttcccagatctgcacagc gagctgaacctgagcagcctggaactgggag atagcgccctgtacttctgtgcctctagcgt gtgggcctctgGCGGctacgagcagtatttt ggccctggcaccagactgaccgtgaccgagg atctgaagaacgtgttcccccacctgaggtggc cgtgttcgagccttctaaggccgagattgcc cacacacagaaagccacactcgtgtgtctgg ccaccggcttctatcccgatcacgtggaact gtcttggtgggtcaacggcaaagaggtgcac agcggcgtcagcacagatccccagcctctga aagaacagcccgctctgaacgacagccggta ctgtctgagcagcagactgagagtgtccgcc accttctggcagaaccccagaaaccacttca gatgccaggtgcagttctacggcctgagcga gaacgatgagtggacccaggacagagctaag cccgtgacacagatcgtgtctgccgaagctt ggggcagagccgattgtggcatcaccagcag atcttaccaccagggcgtgctgagcgccacc atcctgtatgagatcctgctgggcaaagcca ctctgtacgccgtgctggtgtctgccctggt gctgatggccatggtcaagcggaaggatagc agaggc |
| | | Amino acid sequence |
| PRAME epitope | SEQ ID NO: 1 | SLLQHLIGL |
| CDR1 alpha | SEQ ID NO: 2 | SIFNT |
| CDR1 beta | SEQ ID NO: 3 | SGDLS |
| CDR2 alpha | SEQ ID NO: 4 | LYKAGEL |
| CDR2 beta | SEQ ID NO: 5 | YYNGEE |

TABLE 1-continued

| Name | SEQ ID NO. | |
|------|------------|---|
| CDR3 alpha | SEQ ID NO: 6 | CAGLADYGGSQGNLIF |
| CDR3 beta | SEQ ID NO: 7 | CASSVWASGGYEQYF |
| TCR alpha variable region | SEQ ID NO: 8 | MLLEHLLIILWMQLTWVSGQQLNQSPQSMFI QEGEDVSMNCTSSSIFNTWLWYKQDPGEGPV LLIALYKAGELTSNGRLTAQFGITRKDSFLN ISASIPSDVGIYFCA |
| TCR beta variable region | SEQ ID NO: 9 | MGFRLLCCVAFCLLGAGPVDSGVTQTPKHLI TATGQRVTLRCSPRSGDLSVYWYQQSLDQGL QFLIQYYNGEERAKGNILERFSAQQFPDLHS ELNLSSLELGDSALYFCASSV |
| TCR alpha chain (mmC) | SEQ ID NO: 10 | MLLEHLLIILWMQLTWVSGQQLNQSPQSMFI QEGEDVSMNCTSSSIFNTWLWYKQDPGEGPV LLIALYKAGELTSNGRLTAQFGITRKDSFLN ISASIPSDVGIYFCAGLADYGGSQGNLIFGK GTKLSVKPNIQNPDPAVYQLRDSKSSDKSVC LFTDFDSQTNVSQSKDSDVYITDKTVLDMRS MDFKSNSAVAWSNKSDFACANAFNNSIIPED TFFPSSDVPCDVKLVEKSFETDTNLNFQNLS VIGFRILLLKVAGFNLLMTLRLWSS |
| TCR beta chain (mmC) | SEQ ID NO: 11 | MGFRLLCCVAFCLLGAGPVDSGVTQTPKHLI TATGQRVTLRCSPRSGDLSVYWYQQSLDQGL QFLIQYYNGEERAKGNILERFSAQQFPDLHS ELNLSSLELGDSALYFCASSVWASGGYEQYF GPGTRLTVTEDLKNVFPPEVAVFEPSKAEIA HTQKATLVCLATGFYPDHVELSWWVNGKEVH SGVSTDPQPLKEQPALNDSRYCLSSRLRVSA TFWQNPRNHFRCQVQFYGLSENDEWTQDRAK PVTQIVSAEAWGRADCGITSRSYHQGVLSAT ILYEILLGKATLYAVLVSALVLMAMVKRKDS RG |
| 3825 CDR3 alpha | SEQ ID NO: 23 | CAVEPGGSYIPTF |
| 3825 CDR3 beta | SEQ ID NO: 24 | CASSPGLSYEQYF |
| Irrelevant Peptide | SEQ ID NO: 25 | GLSNTHVL |
| TCR alpha constant hs | SEQ ID NO: 26 | IQNPDPAVYQLRDSKSSDKSVCLFTDFDSQT NVSQSKDSDVYITDKTVLDMRSMDFKSNSAV AWSNKSDFACANAFNNSIIPEDTFFPSPESS CDVKLVEKSFETDTNLNFQNLSVIGFRILLL KVAGFNLLMTLRLWSS |
| TCR beta-01 constant hs | SEQ ID NO: 27 TRBC01 '01 | EDLNKVFPPEVAVFEPSEAEISHTQKATLVC LATGFFPDHVELSWWVNGKEVHSGVSTDPQP LKEQPALNDSRYCLSSRLRVSATFWQNPRNH FRCQVQFYGLSENDEWTQDRAKPVTQIVSAE AWGRADCGFTSVSYQQGVLSATILYEILLGK ATLYAVLVSALVLMAMVKRKDF |
| TCR beta-02 constant hs | SEQ ID NO: 28 TRBC02 '01 | EDLKNVFPPEVAVFEPSEAEISHTQKATLVC LATGFYPDHVELSWWVNGKEVHSGVSTDPQP LKEQPALNDSRYCLSSRLRVSATFWQNPRNH FRCQVQFYGLSENDEWTQDRAKPVTQIVSAE AWGRADCGFTSESYQQGVLSATILYEILLGK ATLYAVLVSALVLMAMVKRKDSRG |
| TCR alpha mm constant | SEQ ID NO: 29 | IQNPDPAVYQLRDSKSSDKSVCLFTDFDSQT NVSQSKDSDVYITDKTVLDMRSMDFKSNSAV AWSNKSDFACANAFNNSIIPEDTFFPSSDVP CDVKLVEKSFETDTNLNFQNLSVIGFRILLL KVAGFNLLMTLRLWSS |

TABLE 1-continued

| Name | SEQ ID NO. | |
|------|------------|---|
| TCR beta mm constant | SEQ ID NO: 30 | EDLKNVFPPEVAVFEPSKAEIAHTQKATLVC LATGFYPDHVELSWWVNGKEVHSGVSTDPQP LKEQPALNDSRYCLSSRLRVSATFWQNPRNH FRCQVQFYGLSENDEWTQDRAKPVTQIVSAE AWGRADCGITSRSYHQGVLSATILYEILLGK ATLYAVLVSALVLMAMVKRKDSRG |
| TCR alpha murC constant | SEQ ID NO: 31 | IQNPEPAVYQLKDPRSQDSTLCLFTDFDSQI NVPKTMESGTFITDKTVLDMKAMDSKSNGAI AWSNQTSFTCQDIFKETNATYPSSDVPCDAT LTEKSFETDMNLNFQNLSVMGLRILLLKVAG FNLLMTLRLWSS |
| TCR beta murC constant | SEQ ID NO: 32 | EDLRNVTPPKVTLFEPSKAEIANKQKATLVC LARGFFPDHVELSWWVNGKEVHSGVSTDPQA YKESNYSYCLSSRLRVSATFWHNPRNHFRCQ VQFHGLSEEDKWPEGSPKPVTQNISAEAWGR ADCGITSASYHQGVLSATILYEILLGKATLY AVLVSGLVLMAMVKKKNS |
| PRAME full-length | SEQ ID NO: 33 | MERRRLWGSIQSRYISMSVWTSPRRLVELAG QSLLKDEALAIAALELLPRELFPPLFMAAFD GRHSQTLKAMVQAWPFTCLPLGVLMKGQHLH LETFKAVLDGLDVLLAQEVRPRRWKLQVLDL RKNSHQDFWTVWSGNRASLYSFPEPEAAQPM TKKRKVDGLSTEAEQPFIPVEVLVDLFLKEG ACDELFSYLIEKVKRKKNVLRLCCKKLKIFA MPMQDIKMILKMVQLDSIEDLEVTCTWKLPT LAKFSPYLGQMINLRRLLLSHIHASSYISPE KEEQYIAQFTSQFLSLQCLQALYVDSLFFLR GRLDQLLRHVMNPLETLSITNCRLSEGDVMH LSQSPSVSQLSVLSLSGVMLTDVSPEPLQAL LERASATLQDLVFDECGITDDQLLALLPSLS HCSQLTTLSFYGNSISISALQSLLQHLIGLS NLTHVLYPVPLESYEDIHGTLHLERLAYLHA RLRELLCELGRPSMVWLSANPCPHCGDRTFY DPEPILCPCFMPN |

Specifically, polynucleotides encoding TCR alpha or beta chains, TCR alpha or beta chain variable regions, and TCR CDR3alpha and CDR3beta, as well as TCR variants, constructs and fragments of the invention are provided herein and sequences are depicted in SEQ ID NOs: 13, 14, 15, 16, 17, 18, 19, 20, 21, and 22.

The term "polynucleotide" or "nucleic acid" as used herein comprises a sequence of polyribonucleotides and polydeoxribonucleotides, e.g. modified or unmodified RNA or DNA, each in single-stranded and/or double-stranded form linear or circular, or mixtures thereof, including hybrid molecules. The nucleic acids according to this invention thus comprise DNA (such as dsDNA, ssDNA, cDNA), RNA (such as dsRNA, ssRNA, mRNA ivtRNA), combinations thereof or derivatives (such as PNA) thereof.

A polynucleotide may comprise a conventional phosphodiester bond or a non-conventional bond (e.g., an amide bond, such as found in peptide nucleic acids (PNA)). The polynucleotides of the invention may also contain one or more modified bases, such as, for example, tritylated bases and unusual bases such as inosine. Other modifications, including chemical, enzymatic, or metabolic modifications, are also conceivable, as long as a binding molecule of the invention can be expressed from the polynucleotide. The polynucleotide may be provided in isolated form as defined elsewhere herein. A polynucleotide may include regulatory sequences such as transcription control elements (including promoters, enhancers, operators, repressors, and transcription termination signals), ribosome binding site, introns, or the like.

In particular, the present invention provides a polynucleotide comprising or consisting of a nucleic acid that is at least about 80%, about 85%, about 90%, about 91%, about 92%, about 93%, about 94%, about 95%, about 96%, about 97%, about 98%, about 99%, or 100% identical to a reference polynucleotide sequence selected from the group consisting of sequences as depicted in SEQ ID NOs: 13, 14, 15, 16, 17, 18, 19, 20, 21, and 22.

The polynucleotides described above may or may not comprise additional or altered nucleotide sequences encoding e.g., altered amino acid residues, a signal peptide to direct secretion of the encoded TCR, constant regions or other heterologous polypeptides as described herein. Such polynucleotides may thus encode fusion polypeptides, fragments, variants and other derivatives of the binding molecules described herein.

The nucleic acid sequences of the present invention may be codon-optimized for optimal expression in the desired host cell, e.g. a human lymphocyte; or for expression in bacterial, yeast or insect cells that are particularly envisaged for the expression of a soluble TCR of the invention. Codon-optimization refers to the exchange in a sequence of interest of codons that are generally rare in highly expressed genes of a given species by codons that are generally frequent in highly expressed genes of such species, such codons encoding the same amino acids as the codons that are being exchanged. Selection of optimum codons thus depends on codon usage of the host genome and the presence of several desirable and undesirable sequence motifs.

Vector

Further provided herein is a vector, comprising one or more of the nucleic acids as described herein. A "vector" is a nucleic acid molecule used as a vehicle to transfer (foreign) genetic material into a host cell where it can for instance be replicated and/or expressed.

The term "vector" encompasses, without limitation plasmids, viral vectors (including retroviral vectors, lentiviral vectors, adenoviral vectors, vaccinia virus vectors, polyoma virus vectors, and adenovirus-associated vectors (AAV)), phages, phagemids, cosmids and artificial chromosomes (including BACs and YACs). The vector itself is generally a nucleotide sequence, commonly a DNA sequence that comprises an insert (transgene) and a larger sequence that serves as the "backbone" of the vector. Engineered vectors typically comprise an origin for autonomous replication in the host cells (if stable expression of the polynucleotide is desired), selection markers, and restriction enzyme cleavage sites (e.g. a multiple cloning site, MCS). Vector may additionally comprise promoters, genetic markers, reporter genes, targeting sequences, and/or protein purification tags. As known to those skilled in the art, large numbers of suitable vectors are known to those of skill in the art and many are commercially available.

Targeting Vectors

Targeting vectors can be used to integrate a polynucleotide into the host cell's chromosome by methods known in the art, such as described by J. Sambrook et al., Molecular Cloning: A Laboratory Manual (4th edition), Cold Spring Harbor Laboratory, Cold Spring Harbor Laboratory Press, New York (2012). Briefly, suitable means include homologous recombination or use of a hybrid recombinase that specifically targets sequences at the integration sites. Targeting vectors are typically circular and linearized before used for homologous recombination. As an alternative, the foreign polynucleotides may be DNA fragments joined by fusion PCR or synthetically constructed DNA fragments which are then recombined into the host cell. It is also possible to use heterologous recombination which results in random or non-targeted integration.

Expression Vectors

The vector of the present invention can also be an expression vector. "Expression vectors" or "expression constructs" can be used for the transcription of heterologous polynucleotide sequences, for instance those encoding the TCR of the invention, and translation of their mRNA in a suitable host cell. This process is also referred to as "expression" of the TCR of the invention herein.

Besides an origin of replication, selection markers, and restriction enzyme cleavage sites, expression vectors typically include one or more regulatory sequences operably linked to the heterologous polynucleotide to be expressed.

The term "regulatory sequence" refers to a nucleic acid sequence necessary for the expression of an operably linked coding sequence of a (heterologous) polynucleotide in a particular host organism or host cell and thus include transcriptional and translational regulatory sequences. Typically, regulatory sequences required for expression of heterologous polynucleotide sequences in prokaryotes include a promoter(s), optionally operator sequence(s), and ribosome binding site(s). In eukaryotes, promoters, polyadenylation signals, enhancers and optionally splice signals are typically required. Moreover, specific initiation and secretory signals also may be introduced into the vector in order to allow for secretion of the polypeptide of interest into the culture medium.

A nucleic acid is "operably linked" when it is placed into a functional relationship with another nucleic acid sequence, in particular on the same polynucleotide molecule. For example, a promoter is operably linked with a coding sequence of a heterologous gene when it is capable of effecting the expression of that coding sequence. The promoter is typically placed upstream of the gene encoding the polypeptide of interest and regulates the expression of said gene.

Exemplary regulatory sequences for mammalian host cell expression include viral elements that direct high levels of protein expression in mammalian cells, such as promoters and/or enhancers derived from cytomegalovirus (CMV) (such as the CMV promoter/enhancer), Simian Virus 40 (SV40) (such as the SV40 promoter/enhancer), adenovirus, (e.g., the adenovirus major late promoter (AdMLP)) and polyoma. As set out before, the expression vectors may also include origins of replication and selectable markers.

As mentioned previously, vectors of the invention may further comprise one or more selection markers. Suitable selection markers for use with eukaryotic host cells include, without limitation, the herpes simplex virus thymidine kinase (tk), hypoxanthine-guanine phosphoribosyltransferase (hgprt), and adenine phosphoribosyltransferase (aprt) genes. Other genes include dhfr (methotrexate resistance), gpt (mycophenolic acid resistance) neo (G-418 resistance) and hygro (hygromycin resistance). Vector amplification can be used to increase expression levels. In general, the selection marker gene can either be directly linked to the polynucleotide sequences to be expressed, or introduced into the same host cell by co-transformation.

In view of the above, the present invention thus further provides one or more of the nucleotide sequences described herein inserted into (i.e. comprised by) a vector. Specifically, the invention provides (replicable) vectors comprising a nucleotide sequence encoding a TCR of the invention, or an alpha or beta chain thereof, or an alpha or beta variable domain, or a CDR3 alpha or CDR3beta operably linked to a promoter.

The skilled person will readily be able to select a suitable expression vector based on, e.g., the host cell intended for TCR expression. Examples for suitable expression vectors are viral vectors, such as retroviral vectors e.g. MP71 vectors or retroviral SIN vectors; and lentiviral vectors or lentiviral SIN vectors. Viral vectors comprising polynucleotides encoding the TCR of the invention are for instance capable of infecting lymphocytes, which are envisaged to subsequently express the heterologous TCR. Another example for a suitable expression vector is the Sleeping Beauty (SB) transposon transposase DNA plasmid system, SB DNA plasmid. The nucleic adds and/or in particular expression constructs of the invention can also be transferred into cells by transient RNA transfection.

Currently used viral vectors for native TCR expression typically link the TCR-alpha and TCR-beta chain genes in one vector with either an internal ribosomal entry site (IRES) sequence or the 2A peptide sequence derived from a porcine tsechovirus, resulting in the expression a single messenger RNA (mRNA) molecule under the control of the viral promoter within the transduced cell.

Host Cell

The present invention further provides a host cell comprising the TCR, nucleic acid or the vector described herein.

A variety of host cells can be used in accordance with the invention. As used herein, the term "host cell" encompasses cells which can be or has/have been recipients of polynucleotides or vectors described herein and/or express (and optionally secreting) the TCR of the present invention. The terms "cell" and "cell culture" are used interchangeably to denote the source of a TCR unless it is clearly specified otherwise. The term "host cell" also includes host cell lines. In general, the term "host cell" includes prokaryotic or eukaryotic cells, and also includes without limitation bacteria, yeast cells, fungi cells, plant cells, and animal cells such as insect cells and mammalian cells, e.g. murine, rat, macaque or human cells.

In view of the above, the invention thus provides, inter alia, host cells comprising a polynucleotide or a vector, e.g. an expression vector comprising a nucleotide sequence encoding a TCR or TCR construct as described herein. Polynucleotides and/or vectors of the invention can be introduced into the host cells using routine methods known in the art, e.g. by transfection, transformation, or the like.

"Transfection" is the process of deliberately introducing nucleic acid molecules or polynucleotides (including vectors) into target cells. An example is RNA transfection, i.e. the process of introducing RNA (such as in vitro transcribed RNA, ivtRNA) into a host cell. The term is mostly used for non-viral methods in eukaryotic cells. The term "transduction" is often used to describe virus-mediated transfer of nucleic acid molecules or polynucleotides. Transfection of animal cells typically involves opening transient pores or "holes" in the cell membrane, to allow the uptake of material. Transfection can be carried out using calcium phosphate, by electroporation, by cell squeezing or by mixing a cationic lipid with the material to produce liposomes, which fuse with the cell membrane and deposit their cargo inside. Exemplary techniques for transfecting eukaryotic host cells include lipid vesicle mediated uptake, heat shock mediated uptake, calcium phosphate mediated transfection (calcium phosphate/DNA co-precipitation), microinjection and electroporation.

The term "transformation" is used to describe non-viral transfer of nucleic acid molecules or polynucleotides (including vectors) into bacteria, and also into non-animal eukaryotic cells, including plant cells. Transformation is hence the genetic alteration of a bacterial or non-animal eukaryotic cell resulting from the direct uptake through the cell membrane(s) from its surroundings and subsequent incorporation of exogenous genetic material (nucleic acid molecules). Transformation can be effected by artificial means. For transformation to happen, cells or bacteria must be in a state of competence, which might occur as a time-limited response to environmental conditions such as starvation and cell density. For prokaryotic transformation, techniques can include heat shock mediated uptake, bacterial protoplast fusion with intact cells, microinjection and electroporation. Techniques for plant transformation include *Agrobacterium* mediated transfer, such as by *A. tumefaciens*, rapidly propelled tungsten or gold microprojectiles, electroporation, microinjection and polyethylene glycol mediated uptake.

In view of the above, the present invention thus further provides host cells comprising at least one polynucleotide sequence and/or vector as described herein.

For expression of the TCR of the invention, a host cell may be chosen that modulates the expression of the inserted polynucleotide sequences, and/or modifies and processes the gene product (i.e. RNA and/or protein) as desired. Such modifications (e.g. glycosylation) and processing (e.g. cleavage) of gene products may be important for the function of the TCR. Different host cells have characteristic and specific mechanisms for the post-translational processing and modification of gene products. Appropriate cell lines or host systems can be chosen to ensure the correct modification and processing of the product. To this end, eukaryotic host cells that possess the cellular machinery for proper processing of the primary transcript, glycosylation, and phosphorylation of the gene product may be used.

It is envisaged herein to provide (a) host cells for expressing and obtaining a TCR of the invention, in particular in soluble form ("production host cells") and (b) host cells expressing a TCR of the invention and having effector function ("effector host cells"). Such "effector host cells" are particularly useful for therapeutic applications and are envisaged for administration to a subject in need thereof. Preferred "effector host cells" include lymphocytes such as cytotoxic T lymphocytes (CTLs), CD8+ T cells, CD4+ T cells, natural killer (NK) cells, natural killer T (NKT) cells, gamma/delta-T cells.

"Production Host Cell"

Cells

"Production host cells" used for the expression of a soluble TCR of the invention are preferably capable of expressing high amounts of recombinant protein.

In accordance with the foregoing, conceivable expressions systems (i.e. host cells comprising an expression vector as described above) include microorganisms such as bacteria (e.g. *E. coli, B. subtilis*) transformed with recombinant bacteriophage DNA, plasmid DNA or cosmid DNA expression vectors; yeast (e.g. *Saccharomyces, Pichia*) transformed with recombinant yeast expression vectors; insect cell systems infected with recombinant virus expression vectors (e.g. baculovirus); plant cell systems infected with recombinant virus expression vectors (e.g. cauliflower mosaic virus, CaMV; tobacco mosaic virus, TMV) or transformed with recombinant plasmid expression vectors (e.g., Ti plasmid). Mammalian expression systems harboring recombinant expression constructs containing promoters derived from the genome of mammalian cells (e.g. metallothionein promoter) or from mammalian viruses (e.g. the adenovirus late promoter; the vaccinia virus 7.5K promoter, the cytomegalovirus (CMV) major immediate-early promoter (MIEP) promoter) are often preferred. Suitable mammalian host cells can be selected from known cell lines (e.g. COS, CHO, BLK, 293, 3T3 cells), however it is also conceivable to use lymphocytes such as cytotoxic T lymphocytes (CTLs), CD8+ T cells, CD4+ T cells, natural killer (NK) cells, natural killer T (NKT) cells, gamma/delta-T-cells.

Exemplary mammalian host cells that can be used for as "production host cells" include Chinese Hamster Ovary (CHO cells) including DHFR minus CHO cells such as DG44 and DUXBI 1, NSO, COS (a derivative of CVI with SV40 T antigen). HEK293 (human kidney), and SP2 (mouse myeloma) cells. Other exemplary host cell lines include, but are not limited to, HELA (human cervical carcinoma), CVI (monkey kidney line), VERY, BHK (baby hamster kidney), MDCK, 293, WI38, R1610 (Chinese hamster fibroblast) BALBC/3T3 (mouse fibroblast), HAK (hamster kidney line), P3×63-Ag3.653 (mouse myeloma), BFA-IcIBPT (bovine endothelial cells), and RAJI (human lymphocyte). Host cell lines are typically available from commercial services, the American Tissue Culture Collection (ATCC) or from published literature.

Non-mammalian cells such as bacterial, yeast, insect or plant cells are also readily available and can also be used as "production host cells" as described above. Exemplary bacterial host cells include Enterobacteriaceae, such *Escherichia coli, Salmonella*; Bacillaceae, such as *Bacillus subtilis*; Pneumococcus; *Streptococcus*, and *Haemophilus* influenza. Other host cells include yeast cells, such as *Saccharomyces cerevisiae*, and *Pichia pastoris*. Insect cells include, without limitation, *Spodoptera frugiperda* cells.

In accordance with the foregoing, the present invention also provides a method for producing and obtaining a TCR as described herein comprising the steps of (a) incubating a host cell (i.e. a production host cell) under conditions causing expression of said TCR and (b) purifying said TCR.

Cultivation

The host cells harboring the expression vector are grown under conditions appropriate for the production of the TCR provided herein, in particular alpha chains and/or beta chains as described elsewhere herein, and assayed for alpha and/or beta chain protein synthesis. For the expression of double-chained TCRs, vectors encoding both the alpha and beta chains may be co-expressed in the host cell for expression of the entire molecule.

Purification

Once a TCR of the invention has been expressed, it may be purified by any purification method known in the art, for example, by chromatography (e.g. ion exchange chromatography (e.g. hydroxylapatite chromatography), affinity chromatography, particularly Protein A, Protein G or lectin affinity chromatography, sizing column chromatography), centrifugation, differential solubility, hydrophobic interaction chromatography, or by any other standard technique for the purification of proteins. The skilled person will readily be able to select a suitable purification method based on the individual characteristics of the TCR to be recovered.

"Effector Host Cell"

As mentioned earlier, the present invention also provides for "effector host cells" comprising a nucleotide sequence, vector or TCR of the invention. Said effector host cells are modified using routine methods to comprise a nucleic acid sequence encoding the TCR of the invention, and are envisaged to express the TCR described herein, in particular on the cell surface. For the purposes of the present invention, "modified host cells expressing a TCR of the invention" generally refers to (effector or production) host cells treated or altered to express a TCR according to the present invention, for instance by RNA transfection as described in the appended Examples. Other methods of modification or transfection or transduction, such as those described elsewhere herein, are also envisaged. The term "modified host cell" thus includes "transfected", "transduced" and "genetically engineered" host cells preferably expressing the TCR of the present invention.

Preferably, such "(modified) effector host cells" (in particular "(modified) effector lymphocytes") are capable of mediating effector functions through intracellular signal transduction upon binding of the TCR to its specific antigenic target. Such effector functions include for instance the release of perforin (which creates holes in the target cell membrane), granzymes (which are proteases that act intracellularly to trigger apoptosis), the expression of Fas ligand (which activates apoptosis in a FAS-bearing target cell) and the release of cytokines, preferably Th1/Tc1 cytokines such as IFN-gamma, IL-2 and TNF-α. Thus, an effector host cell engineered to express the TCR of the invention that is capable recognizing and binding to its antigenic target in the subject to be treated is envisaged to carry out the above-mentioned effector functions, thereby killing the target (e.g. cancer) cells. Cytolysis of target cells can be assessed e.g. with the CTL fluorescent killing assay (CTL, USA) detecting the disappearance of fluorescently labeled target cells during co-culture with TCR-transfected recipient T cells.

In view of the above, effector host cells preferably express a functional TCR, i.e. that typically comprises a TCR alpha and beta chain described herein; and also the signal transducing subunits CD3 gamma, delta, epsilon and zeta (CD3 complex). Moreover, expression of co-receptors CD4 or CD8 may also be desired. Generally, lymphocytes harboring the required genes involved in antigen binding, receptor activation and downstream signaling (e.g. Lck, FYN, CD45, and/or Zap70), T cells are particularly suitable as effector host cells. However, effector host cells expressing the TCR of the invention as a "binding domain" without the CD3 signal transducing subunit and/or aforementioned downstream signaling molecules (i.e. being capable of recognizing the antigenic target described herein, but without effecting functions mediated by CD3 and/or the aforementioned downstream signaling molecules) are also envisaged herein. Such effector cells are envisaged to be capable of recognizing the antigenic target described herein, and optionally of effecting other functions not associated with CD3 signaling and/or signaling of the aforementioned downstream signaling molecules. Examples include NK or NKT cells expressing the inventive TCR and being capable of e.g. releasing cytotoxic granules upon recognition of their antigenic target.

Thus, cytotoxic T lymphocytes (CTLs), CD8+ T cells, CD4+ T cells, natural killer (NK) cells, natural killer T (NKT) cells, gamma/delta-T cells are considered useful lymphocyte effector host cells. Such lymphocytes expressing the recombinant TCR of the invention are also referred to as "modified effector lymphocytes" herein. The skilled person will however readily acknowledge that in general any component of the TCR signaling pathway leading to the desired effector function can be introduced into a suitable host cell by recombinant genetic engineering methods known in the art.

Effector host cells in particular lymphocytes such as T cells can be autologous host cells that are obtained from the subject to be treated and transformed or transduced to express the TCR of the invention. Typically, recombinant expression of the TCR will be accomplished by using a viral vector as described in the appended Examples. Techniques for obtaining and isolating the cells from the patient are known in the art.

As mentioned earlier, the effector host cells provided herein are particularly envisaged for therapeutic applications. Further genetic modifications of the host cells may be desirable in order to increase therapeutic efficacy. E.g. when using autologous CD8+ T cells as "effector host cells" suitable additional modifications include downregulation of the endogenous TCR, CTLA-4 and/or PD-1 expression; and/or amplification of co-stimulatory molecules such as CD28, CD134, CD137. Means and methods for achieving the aforementioned genetic modifications have been described in the art.

Methods for targeted genome engineering of host cells are known in the art and include, besides gene knockdown with siRNA, the use of so-called "programmable nucleases" such as zinc-finger nucleases (ZFNs), transcription activator-like effector nucleases (TALENs) and RNA-guided engineered nucleases (RGENs) derived from the bacterial clustered regularly interspaced short palindromic repeat (CRISPR)-Cas (CRISPR-associated) system, as inter alia reviewed in Kim & Kim Nature Reviews Genetics 15, 321-334 (2014). For instance, programmable nucleases such as TALENs can be employed to cut the DNA regions that code for "unwanted" proteins, such as PD-1, CTLA-4 or an endogenous TCR, and thereby reducing their expression. When T cells are used as (effector) host cells, downregulation of the endogenous TCR has the benefit of reducing unwanted "mispairing" of endogenous and exogenous TCR alpha/beta chains.

Pharmaceutical Composition

The present invention further provides a pharmaceutical composition comprising the TCR, the nucleic acid, the vector and/or the host cell as described herein as one or more active agents, and, optionally, one or more pharmaceutically excipient(s). Accordingly, the use of said TCR, nucleic acid, vector and host cell for the manufacture of a pharmaceutical composition or medicament is also envisaged herein.

The term "pharmaceutical composition" particularly refers to a composition suitable for administering to a human. However, compositions suitable for administration to non-human animals are generally also encompassed by the term.

The pharmaceutical composition envisaged by the present invention may further comprise one or more checkpoint inhibitors, preferably selected from the group consisting of a CTLA-4 inhibitor, a PD-1 inhibitor and a PD-L1 inhibitor. All of the above-mentioned inhibitors are immune checkpoint inhibitors capable of immune response downregulation. The cytotoxic lymphocyte-associated protein 4 (CTLA-4) inhibitor is a constitutively expressed protein receptor in regulatory T cells, but only upregulated in conventional T cells after activation. PD-1 and PD-L1 inhibitors act to inhibit the association of the programmed death-ligand 1 (PD-L1) with its receptor, programmed cell death protein 1 (PD-1). The interaction of these cell surface proteins is involved in the suppression of the immune system and occurs following infection to limit the killing of bystander host cells and prevent autoimmune disease. It thus is preferred that said checkpoint inhibitors are combined to the pharmaceutical composition according to in the present invention.

Further checkpoint inhibitors encompassed by the present invention are LAG3, ICOS, TIM3, VISTA and CEACAM1. LAG3 is an Inhibitory receptor on antigen activated T-cells. The ICOS protein belongs to the CD28 and CTLA-4 cell-surface receptor family. It forms homodimers and plays an important role in cell-cell signalling, immune responses, and regulation of cell proliferation. TIM3 or Hepatitis A Virus Cellular Receptor encodes a protein belonging to the immunoglobulin superfamily, and TIM family of proteins. CD4-positive T helper lymphocytes can be divided into types 1 (Th1) and 2 (Th2) on the basis of their cytokine secretion patterns. VISTA or V-Set Immunoregulatory Receptor encodes an immunoregulatory receptor which inhibits T-cell response. The CEACAM1 gene encodes a member of the carcinoembryonic antigen (CEA) gene family, which belongs to the immunoglobulin superfamily. These checkpoint inhibitors may also be combined with the pharmaceutical composition.

The pharmaceutical composition and its components (i.e. active agents and optionally excipients) are preferably pharmaceutically acceptable, i.e. capable of eliciting the desired therapeutic effect without causing any undesirable local or systemic effects in the recipient. Pharmaceutically acceptable compositions of the invention may for instance be sterile. Specifically, the term "pharmaceutically acceptable" may mean approved by a regulatory agency or other generally recognized pharmacopoeia for use in animals, and more particularly in humans.

The active agent described in the foregoing (for instance the host cell or the TCR) is preferably present in the pharmaceutical composition in a therapeutically effective amount. By "therapeutically effective amount" is meant an amount of the active agent that elicits the desired therapeutic effect. Therapeutic efficacy and toxicity can be determined by standard procedures, e.g. in cell culture or in test animals, e.g. $ED_{50}$ (the dose therapeutically effective in 50% of the population) and $LD_{50}$ (the dose lethal to 50% of the population). The dose ratio between therapeutic and toxic effects is the therapeutic index, and it can be expressed as the ratio, $ED_{50}/LD_{50}$. Pharmaceutical compositions that exhibit large therapeutic indices are preferred.

Dosage

The exact dosage of the TCR polynucleotide, vector or host cell will be ascertainable by one skilled in the art using known techniques. Suitable dosages provide sufficient amounts of the active agent of the invention and are preferably therapeutically effective, i.e. elicit the desired therapeutic effect.

As is known in the art, adjustments for purpose of the treatment (e.g. remission maintenance vs. acute flare of disease), route, time and frequency of administration, time and frequency of administration formulation, age, body weight, general health, sex, diet, severity of the disease state, drug combination(s), reaction sensitivities, and tolerance/response to therapy may be necessary. Suitable dosage ranges, for instance for a soluble TCR as described herein, can be determined using data obtained from cell culture assays and animal studies and may include the $ED_{50}$. Typically, dosage amounts may vary from 0.1 to 100000 micrograms, up to a total dose of about 2 g, depending upon the route of administration. Exemplary dosages of the active agent of the invention are in the range from about 0.01 mg/kg to about 10 mg/kg, from about 0.1 mg/kg to about 10 mg/kg, from about 1 mg/kg to about 10 mg/kg, from about 1 mg/kg to about 5 mg/kg, from about 0.01 mg/kg to about 1 mg/kg, or from about 0.1 mg/kg to about 1 mg/kg. Guidance as to particular dosages and methods of delivery is provided in the literature. It is recognized that treatment may require a single administration of a therapeutically effective dose, or multiple administrations of a therapeutically effective dose of the active agent of the invention. E.g., some pharmaceutical compositions might be administered every 3 to 4 days, every week, or once every two weeks, or once within a month depending on formulation, half-life and clearance rate of the particular composition. As set out previously, the pharmaceutical composition may optionally comprise one or more excipients and/or additional active agents.

Excipients

The term 'excipient' includes fillers, binders, disintegrants, coatings, sorbents, anti-adherents, glidants, preservatives, antioxidants, flavoring, coloring, sweeting agents, solvents, co-solvents, buffering agents, chelating agents, viscosity imparting agents, surface active agents, diluents, humectants, carriers, diluents, preservatives, emulsifiers, stabilizers and tonicity modifiers. It is within the knowledge of the skilled person to select suitable excipients for preparing the desired pharmaceutical composition of the invention. Exemplary carriers for use in the pharmaceutical composition of the invention include saline, buffered saline, dextrose, and water. Typically, choice of suitable excipients will inter alia depend on the active agent used, the disease to be treated, and the desired formulation of the pharmaceutical composition.

Additional Active Agents

The present invention further provides pharmaceutical compositions comprising one or more of the inventive active agents specified above (for instance a host cell or a TCR construct), and one or more additional active agents that are suitable for treatment and/or prophylaxis of the disease to be treated. Preferred examples of active ingredients suitable for combinations include known anti-cancer drugs such as cisplatin, maytansine derivatives, rachelmycin, calicheamicin, docetaxel, etoposide, gemcitabine, ifosfamide, irinotecan, melphalan, mitoxantrone, sorfimer sodiumphotofrin II, temozolmide, topotecan, trimetreate glucuronate, auristatin E vincristine and doxorubicin; and peptide cytotoxins such as ricin, diphtheria toxin, *pseudomonas* bacterial exotoxin A, DNAase and RNAase; radio-nuclides such as iodine 131, rhenium 186, indium 111, yttrium 90, bismuth 210 and 213, actinium 225 and astatine 213; prodrugs, such as antibody directed enzyme pro-drugs; immuno-stimulants, such as IL-2, chemokines such as IL-8, platelet factor 4, melanoma growth stimulatory protein, etc., antibodies or fragments thereof such as anti-CD3 antibodies or fragments thereof, complement activators, xenogeneic protein domains, allogeneic protein domains, viral/bacterial protein domains and viral/bacterial peptides.

Administration

A variety of routes are applicable for administration of the pharmaceutical composition according to the present invention. Typically, administration will be accomplished parentally. Methods of parenteral delivery include topical, intra-arterial, intramuscular, subcutaneous, intramedullary, intrathecal, intraventricular, intravenous, intraperitoneal, intrauterine, intravaginal, sublingual or intranasal administration.

Formulation

The pharmaceutical compositions of the invention can be formulated in various forms, depending inter alia on the active agent used (e.g. soluble TCR), e.g. in solid, liquid, gaseous or lyophilized form and may be, inter alia, in the form of an ointment, a cream, transdermal patches, a gel, powder, a tablet, solution, an aerosol, granules, pills, suspensions, emulsions, capsules, syrups, liquids, elixirs, extracts, tincture or fluid extracts or in a form which is particularly suitable for the desired method of administration. Processes known per se for producing medicaments are indicated in 22nd edition of Remington's Pharmaceutical Sciences (Ed. Maack Publishing Co, Easton, Pa., 2012) and may include, for instance conventional mixing, dissolving, granulating, dragee-making, levigating, emulsifying, encapsulating, entrapping or lyophilizing processes. Pharmaceutical compositions comprising, for instance, host cells or soluble TCR as described herein will typically be provided in a liquid form, and preferably comprise a pharmaceutically acceptable buffer.

After pharmaceutical compositions of the invention have been prepared they can be placed in an appropriate container and labeled for treatment of an indicated condition. Such labeling would for instance include amount, frequency and method of administration.

Treatment

In view of the foregoing the present invention thus provides a TCR, nucleic acid, vector and/or host cell as described herein for use as a medicament in detection, diagnosis, prognosis, prevention and/or treatment of cancer.

The TCR, nucleic acid, vector and/or host cell can in general be employed for treatment detection, diagnosis, prognosis, prevention and/or treatment of diseases or disorders. The term "treatment" in all its grammatical forms includes therapeutic or prophylactic treatment of a subject in need thereof. A "therapeutic or prophylactic treatment" comprises prophylactic treatments aimed at the complete prevention of clinical and/or pathological manifestations or therapeutic treatment aimed at amelioration or remission of clinical and/or pathological manifestations. The term "treatment" thus also includes the amelioration or prevention of diseases.

Such diseases envisaged to be treated when using the pharmaceutical composition of the present invention are preferably cancer selected from the group consisting of melanoma, bladder carcinoma, colon carcinoma, and breast adenocarcinoma, sarcoma, prostate cancer, uterine cancer, uveal cancer, uveal melanoma, squamous head and neck cancer, synovial carcinoma, Ewing's sarcoma, triple negative breast cancer, thyroid cancer, testicular cancer, renal cancer, pancreatic cancer, ovarian cancer, esophageal cancer, non-small-cell lung cancer, non-Hodgkin's lymphoma, multiple myeloma, melanoma, hepatocellular carcinoma, head and neck cancer, gastric cancer, endometrial cancer, colorectal cancer, cholangiocarcinoma, breast cancer, bladder cancer, myeloid leukemia and acute lymphoblastic leukemia, preferably wherein the cancer is selected from the group consisting of NSCLC, SCLC, breast, ovarian or colorectal cancer, sarcoma or osteosarcoma.

The terms "subject" or "individual" or "animal" or "patient" are used interchangeably herein to refer to any subject, particularly a mammalian subject, for whom therapy is desired. Mammalian subjects generally include humans, non-human primates, dogs, cats, guinea pigs, rabbits, rats, mice, horses, cattle, cows, and the like. However, it will readily be understood that the TCR, nucleic acids, vectors, host cells and pharmaceutical compositions provided herein are especially envisaged for treatment of human subjects, in particular those that are HLA-A2-positive.

Direct Administration

For therapy, a TCR—in particular a soluble TCR of the invention—, nucleic acids, vectors (such as viral vectors) or host cells of the invention can be administered directly to the subject in need thereof. Thus the present invention provides a TCR, nucleic acid, vector or host cells for use in a method of detecting, diagnosing, prognosing, preventing and/or treating of cancer. Said method can comprise the steps of (a) providing one or more of (i) a TCR (ii), a nucleic acid, (iii)

a vector, (iv) a host cell, and/or (v) a pharmaceutical composition of the present invention; and (b) administering one or more of (i)-(v) to the subject in need thereof. Optionally, the method can comprise a further step of cancer therapy, e.g. radiation, or administration of one or more anti-cancer agents.

Ex Vivo Treatment

Treatment according to the invention may also comprise the steps of (a) providing a sample of a subject, said sample comprising lymphocytes; (b) providing one or more of (i) the TCR, (ii) nucleic acid, (ii) vector (iv) host cell and/or (v) pharmaceutical composition of the invention (c) introducing of one or more of (i) to (v) of step (b) into the lymphocytes of step (a) and, thereby, obtaining modified lymphocytes, (d) administering the modified lymphocytes of step (c) to a subject or patient in need thereof.

The lymphocytes provided in step (a) are particularly envisaged to be "effector host cells" as described in the foregoing and are advantageously selected from T cells, NK cells and/or NKT cells, especially CD8$^+$ T cells; and can be obtained in a previous step from a sample—in particular a blood sample—of the subject by routine methods known in the art. It is however also conceivable to use other lymphocytes that are preferably capable of expressing the TCR of the present invention and exert the desired biological effector functions as described herein. Moreover, said lymphocytes will typically be selected for compatibility with the subject's immune system, i.e. they will preferably not elicit an immunogenic response. For instance, it is conceivable to use a "Universal Recipient cells", i.e. universally compatible lymphocytes exerting the desired biological effector functions that can be grown and expanded in vitro. Use of such cells will thus obviate the need for obtaining and providing the subject's own lymphocytes in step (a).

The ex vivo introduction of step (c) can be carried out by introducing a nucleic acid or vector described herein via electroporation into the lymphocytes, or by infecting the lymphocytes with a viral vector, such as a lentiviral or retroviral vector as described previously in the context of the effector host cell. Other conceivable methods include the use of by transfection reagents, such as liposomes, or transient RNA transfection. The transfer of antigen-specific TCR genes into (primary) T cells by e.g. (retro-)viral vectors or transient RNA transfection represents a promising tool for generating tumor-associated antigen-specific T cells that can subsequently be re-introduced into the donor, where they specifically target and destroy tumor cells expressing said antigen. In the present invention, said tumor-associated antigen is PRAME as defined herein, particularly in its HLA-A*02 bound form.

Treatment according to the invention may also comprise the steps of (a) providing a sample of a subject, said sample comprising lymphocytes; while the treatment consists of (b) providing one or more of (i) the TCR; (ii) the nucleic acid; (iii) the vector; (iv) the host cell; and (v) the pharmaceutical composition; (c) introducing of one or more of (i) to (v) of step (b) into the lymphocytes of step and, thereby, obtaining modified lymphocytes, (d) administering the modified lymphocytes of step (c) to a subject or patient in need thereof.

In view of the above, a further aspect of the present invention is thus the use of a TCR, a nucleic acid sequence, a vector and/or a host cell as described elsewhere herein for generating modified lymphocytes. Means and methods for introducing, e.g. a nucleic acid and a vector into the lymphocytes have been described elsewhere herein.

Diagnostic Composition

The present invention also provides a diagnostic composition comprising, as one or more diagnostic agent(s), the TCR, nucleic acid, the vector and/or the host cell as described herein. Typically, said diagnostic agent will comprise means for detecting its binding to its antigenic target, for instance a label as described in the context of the TCR constructs of the invention. As regards the host cell, it is for instance conceivable to use modified host cells comprising a dye or a contrast agent that is released (instead of cytotoxic granules) upon antigen recognition.

Use

The present invention envisages the use of the diagnostic agents described in the foregoing for detecting, diagnosing and/or prognosing cancer in a subject which can be accomplished in vivo or in vitro.

Thus the invention provides a diagnostic composition for use in detecting, diagnosing cancer in a subject in vivo, said composition comprising, as a diagnostic agent, the TCR, the nucleic acid, the vector and/or the host cell of the invention. The method will typically comprise (a) administering said diagnostic agent to the subject and (b) detecting binding of said diagnostic agent to its antigenic target.

Moreover, the invention provides a method of detecting, diagnosing and/or prognosing cancer in a subject in vitro. In accordance the present invention also provides a method of detecting the presence of a cancer in a subject, comprising the steps of (a) providing a sample of a subject, said sample comprising one or more cells; (b) contacting said sample with the TCR, host cell and/or the pharmaceutical composition of the invention; thereby forming a complex, and (c) detecting the complex. Said complex is envisaged to be indicative for binding of the diagnostic agent to its antigenic target and is of the presence of a (cancer) cell expressing said antigenic target.

In both methods binding of the diagnostic agent to its antigenic target is detectable by using routine methods known in the art and will inter alia depend on the specific diagnostic agent used. Suitable labels that can be coupled to the diagnostic agent of the invention are exemplified in the section relating to labeled TCR constructs.

Further it is envisaged by the present invention to comprise the use of a TCR, nucleic acid or vector as described herein for the generation of modified lymphocytes. As described somewhere else herein preferred lymphocytes include but not limited to cytotoxic T lymphocytes (CTLs), CD8+ T cells, CD4+ T cells, natural killer (NK) cells, natural killer T (NKT) cells, gamma/delta-T cells.

It must be noted that as used herein, the singular forms "a", "an", and "the", include plural references unless the context clearly indicates otherwise. Thus, for example, reference to "a reagent" includes one or more of such different reagents and reference to "the method" includes reference to equivalent steps and methods known to those of ordinary skill in the art that could be modified or substituted for the methods described herein.

Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the present invention.

The term "and/or" wherever used herein includes the meaning of "and", "or" and "all or any other combination of the elements connected by said term".

The term "about" or "approximately" as used herein means within 20%, preferably within 10%, and more preferably within 5% of a given value or range. It includes, however, also the concrete number, e.g. "about 20" includes 20.

The term "less than" or "greater than" includes the concrete number. For example, less than 20 means less than or equal to. Similarly, more than or greater than means more than or equal to, or greater than or equal to, respectively.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step. When used herein the term "comprising" can be substituted with the term "containing" or "including" or sometimes when used herein with the term "having".

When used herein "consisting of" excludes any element, step, or ingredient not specified in the claim element. When used herein, "consisting essentially of" does not exclude materials or steps that do not materially affect the basic and novel characteristics of the claim.

In each instance herein any of the terms "comprising", "consisting essentially of" and "consisting of" may be replaced with either of the other two terms.

It should be understood that this invention is not limited to the particular methodology, protocols, material, reagents, and substances, etc., described herein and as such can vary. The terminology used herein is for the purpose of describing particular embodiments only, and is not intended to limit the scope of the present invention, which is defined solely by the claims.

All publications and patents cited throughout the text of this specification (including all patents, patent applications, scientific publications, manufacturers specifications, instructions, etc.), whether supra or infra, are hereby incorporated by reference in their entirety. Nothing herein is to be construed as an admission that the invention is not entitled to antedate such disclosure by virtue of prior invention. To the extent the material incorporated by reference contradicts or is inconsistent with this specification, the specification will supersede any such material.

A better understanding of the present invention and of its advantages will be obtained from the following example, offered for illustrative purposes only. The example is not intended to limit the scope of the present invention in any way.

EXAMPLES OF THE INVENTION

The following Examples illustrate the invention, but are not to be construed as limiting the scope of the invention.

TABLE 2

Overview of the TCRs tested in the Examples.

| Name | Company | Inter-national Publication Number | Seq ID NO alpha full length (aa) | Seq ID NO beta full length (aa) |
|---|---|---|---|---|
| T23.8-2.1-027-004 46SLL | Medigene AG Leiden University Medical Center | WO 2016/ 142783 A2 | 37 | 43 |

TABLE 2-continued

Overview of the TCRs tested in the Examples.

| Name | Company | Inter-national Publication Number | Seq ID NO alpha full length (aa) | Seq ID NO beta full length (aa) |
|---|---|---|---|---|
| 54SLL | Leiden University Medical Center | WO 2016/ 142783 A2 | 13 | 19 |
| ImCore_Scaffold | Immunocore Limited | WO 2018/ 234319 A1 | 2 | 3 |
| ImCorePrefCombi1 | Immunocore Limited | WO 2018/ 234319 A1 | 39, 40, 45 (CDR1-3) | 42, 48, 51 (CDR1-3) |
| R11P3D3 | Immatics Biotechnologies GmbH | WO 2018/ 172533 A2 | 6 | 12 |
| R11P3D3_KE | Immatics Biotechnologies GmbH | WO 2018/ 172533 A2 | 132 | 138 |

Example 1: Peptide Specificity

T2 cells were either loaded with the specific SLL peptide (SLLQHLIGL (SEQ ID NO: 1)) or an irrelevant peptide (GLSNTHVL (SEQ ID NO: 25)) at a concentration of $10^{-5}$ M for 1.5 hours at 37° Celsius. These cells were then co-cultured with TCR-transduced T cells in an Effector: Target ratio of 1:1 (using 10.000 effector cells/96-well). After 20 hours, the IFN-gamma level in the cell culture supernatant was measured using a standard IFN-gamma ELISA. All TCR-transduced effector cells, except the negative control (neg. contr.) TCR show recognition of the specific SLL peptide, but not the irrelevant peptide when loaded on T2 cells (FIG. 1).

Example 2: Functional Avidity

The aim of the experiment was to measure functional avidity of the SLL peptide-specific TCR. Functional avidity refers to the accumulated strength of multiple affinities of individual non-covalent binding interactions, such as between the transgenic TCR and the pMHC complex. Functional avidities of TCR-transgenic T cell populations are measured as the half-maximal relative IFN-gamma release ($EC_{50}$ values) in co-culture with T2 cells (Effector:Target of 1:1, 10.000 effector cells/96-well) loaded with graded (titrated) amounts of SLL peptide ($10^{-5}$ M to $10^{-12}$ M; loading performed for 1.5 hours at 37° Celsius).

Readout used is a standard IFN-gamma ELISA after 20 hours of co-culture (values above 4000 pg are extrapolated using a third-degree polynomial).

Result:

027-004 TCR-transduced T cells show a higher functional avidity compared to 3825 TCR-transduced T cells, indicating a higher sensitivity for very low amounts of the target peptide (FIG. 2).

027-004 TCR-transduced T cells show a higher functional avidity compared to T cells transduced with TCRs disclosed in the art, indicating a higher sensitivity for very low amounts of the target peptide (FIG. 13).

Example 3: TCR Recognition Motif (Serine and Threonine Scan)

The aim of the experiment is to assess critical residues within the SLL epitope sequence that are either essential for direct recognition by the TCR or for peptide binding to the HLA-A*02:01-encoded molecule. Amino acid substitution scanning was used to define critical amino acids in the epitope sequence that abolish recognition by the TCR whenever these residues are exchanged for the amino-acid Serine or Threonine. These "fixed" amino acids can be used to define unique TCR recognition motifs. Serine or Threonine residues are used to systematically replace individual amino acids in the PRAME peptide (Serine and Threonine Scan).

In vitro co-culture of TCR-transduced T cells with T2 cells separately loaded (for 1.5 hours at 37° C.) with $10^{-5}$ M of the different peptides at an E:T ratio of 1:1 (10.000 effector cells/96-well).

Readout: standard IFN-gamma ELISA after 20 hours of co-culture (values above 4000 pg are extrapolated using a third-degree polynomial).

Result:

027-004 TCR-transduced T cells show a different recognition motif with less fixed positions compared to 3825 TCR-transduced T cells in the Serine Scan (FIG. 3).

027-004 TCR-transduced T cells show a different recognition motif in the Threonine Scan than other TCRs disclosed in the art (FIG. 12).

TABLE 3

Overview of target cells used for tumor cell recognition.
*Data derived from http://celllines.tron-mainz.de/.

| Tumor Cell Line | HLA-A*02:01 Status | PRAME Expression | Disease |
|---|---|---|---|
| MelA375 | + | 448.7 RPKM | Melanoma |
| NCI-H1650 | + | 119.4 RPKM | Bronchioloalveolar Carcinoma |
| NCI-H1703 | + | 118.0 RPKM | Lung Adenocarcinoma |

TABLE 4

Overview of target cells used for tumor cell killing.
*Data derived from http://celllines.tron-mainz.de/.

| Tumor Cell Line | HLA-A*02:01 Status | PRAME Expression | Disease |
|---|---|---|---|
| MelA375_NuclightRed | + | 448.7 RPKM | Melanoma |
| NCI-H1650_ NuclightRed | + | 119.4 RPKM | Bronchioloalveolar Carcinoma |

Example 4: Tumor Cell Recognition and Tumor Cell Killing

For tumor cell recognition, the effector cells transduced with either TCR 027-004 or TCR 3825 were co-cultured with $PRAME_{SLL}$-positive or $PRAME_{SLL}$-negative tumor cells at an E:T ratio of 1:1 (10.000 effector cells/96-well) for 20 hours at 37° C., 6% $CO_2$. IFN-gamma secretion of effector cells was determined using standard IFN-gamma ELISA (values above 4000 pg are extrapolated using a third-degree polynomial).

Result:

TCR 027-004 transduced effector cells show better recognition of tumor cells, e.g. of MelA375 compared to 3825 TCR transduced T cells (FIG. 4).

TCR 027-004 transduced effector cells show better recognition of tumor cells (MelA375, NCI-H1650 and NCI-H1703) compared to T cells, which were transduced with TCRs known from the art (FIG. 14).

For tumor cell killing, IncuCyte® NucLight Red Lentivirus-transduced tumor cells were seeded in flat-bottom wells one day prior to the start of the co-culture.

After addition of 20.000 effector cells per well, tumor cells were added (in case 647V 2.500 cells, for all other tumor cell lines 5.000 cells) and the culture plates were transferred to an IncuCyte ZOOM® device and expansion of red fluorescent cells were monitored over 100 hours at 37° C. and 6% $CO_2$ with pictures taken every 4 hours.

All TCR transduced effector cells lyse $PRAME_{SLL}$-positive tumor cells (PRAME-pos), and do not influence the growth of $PRAME_{SLL}$-negative tumor cells (PRAME-neg).

Result:

TCR 027-004 transduced effector cells show better killing of tumor cells, e.g. of MelA375 compared to 3825 TCR transduced T cells (FIG. 5).

TCR 027-004 transduced effector cells show better killing of tumor cells (MelA375 and NCI-H1650) compared to T cells, which were transduced with TCRs known from the art (FIG. 15).

Example 5: Normal Cell Recognition

The aim of this set of experiments is to assess potential on-target/off-tumor and off-target toxicities that could be caused by PRAME-specific TCR-transduced effector cells. For this, HLA-A*02:01-expressing primary cells and induced pluripotent stem cell (iPS)-derived cell lines representing essential tissues or organs were tested for recognition by TCR-transduced T cells.

In vitro co-culture experiments were conducted at adapted E:T ratios according to the individual target cell types (40.000 effector cells/96-well). In line with the properties of the individual targets, cells were seeded one to seven days prior to start of the co-culture at cell densities as per manufacturer's instructions and cultivated in monolayers in flat bottom wells. HLA-A2 expression on neurons was induced using low dose IFN-gamma in the culture medium.

PRAME mRNA expression of all tested normal cells was analyzed by quantitative real-time polymerase chain reaction (qPCR) in order to distinguish on-target/off-tumor from potential off-target toxicities. $10^{-5}$ M peptide-loaded target cells served as internal positive control (SLL peptide).

Readout: Standard IFN-gamma/IL-2 ELISA after 20 hours of co-culture.

Result: TCR transduced T cell populations do not recognize unloaded normal cells in a way that results in high levels of IFN-gamma production. However, if the cells are loaded with the specific SLL peptide they are recognized. Only co-culture with unloaded RPTEC results in minimal IFN-gamma production in both samples, what is due to the known endogenous expression of PRAME in this cell type (FIG. 6).

Example 6: HLA-A*02 Fine-Typing

The aim of the experiments was to determine common HLA-A2 sub-alleles (HLA-A*02:xx; allele designation according to: www.hla.alleles.org) other than HLA-A*02: 01, that are able to present the $PRAME_{SLL}$ epitope and can be recognized by the individual SLL-specific TCRs (HLA-restriction fine-typing). Patients expressing these recognized HLA-A2 sub-alleles could therefore also be included in the study cohort (FIG. 7).

In vitro co-culture of TCR-transduced T cells with selected HLA-A2 sub-allele-positive lymphoblastoid cell lines (LCL; EBV-transformed B cells) at an E:T ratio of 1:2 (10.000 effector cells/96-well) for 20 hours at 37° C., 6% $CO_2$. As effector cells, TCR-transduced PBL of one donor were used. All individual LCL are $10^{-5}$ M SLL peptide-loaded for 1.5 hours at 37° C. and co-cultured with the respective effector cells and tested for IFN-gamma secretion to determine the unique TCR sub-allele recognition of the transduced T cells. Unloaded target cells serve as negative control.

Readout: standard IFN-gamma ELISA after 20 hours of co-culture.

Result: 027-004 efficiently recognizes the PRAME peptide presented by 3 out of 10 tested HLA-A2 sub-alleles (A*02:xx) the HLA-A2 sub-alleles A*02:02 and A*02:04 are recognized at equal levels compared to A*02:01. The control 3825 efficiently recognizes the PRAME peptide presented by 1 out of 10 tested HLA-A2 sub-alleles (A*02:xx), namely the HLA-A2 sub-allele A*02:01 is recognized (FIGS. 8-10).

REFERENCES

Altschul, et al., (1997) Nucleic Acids Res. 25:3389-3402.
Altschul, et al., (1990) J. Mol. Biol. 215:403-410,
Chen et al., Adv Drug Deliv Rev. 2013 Oct. 15: 65(10): 1357-1369
Cold Spring Harbor Laboratory, Cold Spring Harbor Laboratory Press, New York (2012)
EP2173869 (A2)
Gargett and Brown Front Pharmacol. 2014; 5: 235
Kieback et al. Proc Natl Acad Sci USA. 2008 Jan. 15; 105(2):623-8
Maack Publishing Co, Easton, Pa., 2012
Sambrook et al., Molecular Cloning: A Laboratory Manual (4th edition),
Schmitt et al., Hum Gene Ther. 2009 November; 20(11): 1240-1248
Smith, et al., (1981) J. Mol. Biol. 147:195-197
Sommermeyer and Uckert, J Immunol. 2010 Jun. 1; 184 (11):6223-31
Walseng et al., (2015), PLoS ONE 10(4): e0119559
Weis, Manon (2015): Charakterisierung Antigen-spezifischer T-Zellen nach Induktion in TCR-humanisierten Mäusen. Dissertation, LMU München Tierärztliche Fakultät: Veterinary Faculty Ludwigs University of Munich.
Xue et al., Clin Exp Immunol. 2005 February: 139(2): 167-172;
Fiedl et al., Clin Cancer Res 2016 March; 22(5): 1234-1242 for DLBCL
Mitsuhashi et al., Hematology 2014, January 2014
Al-Khadairi et al., Journal of Translational Medicine 2019; 17: 9
WO2019/175209A1

The invention claimed is:

1. A T cell receptor (TCR), wherein the TCR comprises:
   a) a CDR3 of the TCR alpha chain variable region comprising or consisting of the amino acid sequence of SEQ ID NO: 6, a CDR1 of the TCR alpha chain variable region comprising or consisting of the amino acid sequence of SEQ ID NO: 2, and a CDR2 of the TCR alpha chain variable region comprising or consisting of the amino acid sequence of SEQ ID NO: 4, and
   b) a CDR3 of the TCR beta chain variable region comprising or consisting of the amino acid sequence of SEQ ID NO: 7, a CDR1 of the TCR beta chain variable region comprising or consisting of the amino acid sequence of SEQ ID NO: 3, and a CDR2 of the TCR beta chain variable region comprising or consisting of the amino acid sequence of SEQ ID NO: 5.

2. The TCR according to claim 1, wherein the TCR comprises:
   a) a TCR alpha chain comprising a CDR1 having the amino acid sequence of SEQ ID NO: 2, a CDR2 having the amino acid sequence of SEQ ID NO: 4 and a CDR3 having the amino acid sequence of SEQ ID NO: 6, and
   b) a TCR beta chain comprising a CDR1 having the amino acid sequence of SEQ ID NO: 3, a CDR2 having the amino acid sequence of SEQ ID NO: 5 and a CDR3 having the amino acid sequence of SEQ ID NO: 7.

3. The TCR according to claim 1, comprising
   a) a TCR alpha chain variable region comprising or consisting of the amino acid sequence of SEQ ID NO: 8, and
   b) a TCR beta chain variable region comprising or consisting of the amino acid sequence of SEQ ID NO: 9.

4. The TCR according to claim 1, comprising
   a) a TCR alpha chain comprising or consisting of an amino acid sequence selected from SEQ ID NO: 10; or an amino acid sequence having at least 80% identity to SEQ ID NO: 10; and
   b) a TCR beta chain comprising or consisting of an amino acid sequence selected from of SEQ ID NO: 11, or an amino acid sequence having at least 80% identity to SEQ ID NO: 11.

5. The TCR according to claim 1, further comprising one or more fusion component(s) optionally selected from Fc receptors; Fc domains, including IgA, IgD, IgG, IgE, and IgM; cytokines, including IL-2 or IL-15; toxins; antibodies or antigen-binding fragments thereof, including anti-CD3, anti-CD28, anti-CD5, anti-CD16 or anti-CD56 antibodies or antigen-binding fragments thereof, CD247 (CD3-zeta), CD28, CD137, CD134 domain, or combinations thereof, and optionally further comprising at least one linker.

6. The TCR according to claim 1, comprising
   a) at least one TCR alpha chain comprising the CDRs as defined in claim 1; and
   b) at least one TCR beta chain comprising the CDRs as defined in claim 1; and
   c) an antibody or a single chain antibody fragment (scFv) which is directed against an antigen or epitope on the surface of lymphocytes,
   wherein the TCR alpha chain(s) and TCR beta chain(s) are linked to each other and fused, optionally via a linker, to said antibody or scFv.

7. The TCR according to claim 6, wherein said antigen is selected from CD3, CD28, CD5, CD16 or CD56.

8. A nucleic acid encoding the TCR according to claim 1.

9. The nucleic acid according to claim 8, comprising the nucleic acid sequence of SEQ ID NO: 13, 14, 15, 16, 17, 18, 19, 20, 21, or 22.

10. A vector comprising the nucleic acid according to claim 8.

11. A host cell comprising the TCR according to claim 1.

12. A method for obtaining a TCR according to claim 1, comprising
   a) incubating a host cell according to claim 11 under conditions causing expression of said TCR, and
   b) purifying said TCR.

13. A pharmaceutical composition comprising the TCR according to claim 1, and, optionally, pharmaceutically excipient(s).

14. The pharmaceutical composition according to claim 13, further comprising a checkpoint inhibitor.

15. The TCR according to claim 1, comprising:
   a) a TCR alpha chain comprising or consisting of an amino acid sequence having at least 90% identity to SEQ ID NO: 10; and
   b) a TCR beta chain comprising or consisting of an amino acid sequence having at least 90% identity to SEQ ID NO: 11.

16. The TCR according to claim 1, comprising:

a) a TCR alpha chain comprising or consisting of an amino acid sequence having at least 95% identity to SEQ ID NO: 10; and b) a TCR beta chain comprising or consisting of an amino acid sequence having at least 95% identity to SEQ ID NO: 11.

17. The TCR according to claim 1, comprising:

a) a TCR alpha chain comprising or consisting of the amino acid sequence of SEQ ID NO: 10; and b) a TCR beta chain comprising or consisting of the amino acid sequence of SEQ ID NO: 11.

* * * * *

SEQUENCE LISTING

```
<160> NUMBER OF SEQ ID NOS: 33

<210> SEQ ID NO 1
<211> LENGTH: 9
<212> TYPE: PRT
<213> ORGANISM: artificial
<220> FEATURE:
<223> OTHER INFORMATION: PRAME epitope, tumor associated antigene

<400> SEQUENCE: 1

Ser Leu Leu Gln His Leu Ile Gly Leu
1               5

<210> SEQ ID NO 2
<211> LENGTH: 5
<212> TYPE: PRT
<213> ORGANISM: artificial
<220> FEATURE:
<223> OTHER INFORMATION: CDR1 alpha, human modified

<400> SEQUENCE: 2

Ser Ile Phe Asn Thr
1               5

<210> SEQ ID NO 3
<211> LENGTH: 5
<212> TYPE: PRT
<213> ORGANISM: artificial
<220> FEATURE:
<223> OTHER INFORMATION: CDR1 beta, human modified

<400> SEQUENCE: 3

Ser Gly Asp Leu Ser
1               5
```

```
<210> SEQ ID NO 4
<211> LENGTH: 7
<212> TYPE: PRT
<213> ORGANISM: artificial
<220> FEATURE:
<223> OTHER INFORMATION: CDR2 alpha, human modified

<400> SEQUENCE: 4

Leu Tyr Lys Ala Gly Glu Leu
1               5

<210> SEQ ID NO 5
<211> LENGTH: 6
<212> TYPE: PRT
<213> ORGANISM: artificial
<220> FEATURE:
<223> OTHER INFORMATION: CDR2 beta, human modified

<400> SEQUENCE: 5

Tyr Tyr Asn Gly Glu Glu
1               5

<210> SEQ ID NO 6
<211> LENGTH: 16
<212> TYPE: PRT
<213> ORGANISM: artificial
<220> FEATURE:
<223> OTHER INFORMATION: CDR3 alpha, human modified

<400> SEQUENCE: 6

Cys Ala Gly Leu Ala Asp Tyr Gly Gly Ser Gln Gly Asn Leu Ile Phe
1               5                   10                  15

<210> SEQ ID NO 7
<211> LENGTH: 15
<212> TYPE: PRT
<213> ORGANISM: artificial
<220> FEATURE:
<223> OTHER INFORMATION: CDR3 beta, human modified

<400> SEQUENCE: 7

Cys Ala Ser Ser Val Trp Ala Ser Gly Gly Tyr Glu Gln Tyr Phe
1               5                   10                  15

<210> SEQ ID NO 8
<211> LENGTH: 108
<212> TYPE: PRT
<213> ORGANISM: artificial
<220> FEATURE:
<223> OTHER INFORMATION: TCR alpha variable region, human modified

<400> SEQUENCE: 8

Met Leu Leu Glu His Leu Leu Ile Ile Leu Trp Met Gln Leu Thr Trp
1               5                   10                  15

Val Ser Gly Gln Gln Leu Asn Gln Ser Pro Gln Ser Met Phe Ile Gln
            20                  25                  30

Glu Gly Glu Asp Val Ser Met Asn Cys Thr Ser Ser Ile Phe Asn
        35                  40                  45

Thr Trp Leu Trp Tyr Lys Gln Asp Pro Gly Glu Gly Pro Val Leu Leu
    50                  55                  60

Ile Ala Leu Tyr Lys Ala Gly Glu Leu Thr Ser Asn Gly Arg Leu Thr
65                  70                  75                  80

Ala Gln Phe Gly Ile Thr Arg Lys Asp Ser Phe Leu Asn Ile Ser Ala
                85                  90                  95
```

```
Ser Ile Pro Ser Asp Val Gly Ile Tyr Phe Cys Ala
            100                 105

<210> SEQ ID NO 9
<211> LENGTH: 114
<212> TYPE: PRT
<213> ORGANISM: artificial
<220> FEATURE:
<223> OTHER INFORMATION: TCR beta variable region, human modified

<400> SEQUENCE: 9

Met Gly Phe Arg Leu Leu Cys Cys Val Ala Phe Cys Leu Leu Gly Ala
1               5                   10                  15

Gly Pro Val Asp Ser Gly Val Thr Gln Thr Pro Lys His Leu Ile Thr
            20                  25                  30

Ala Thr Gly Gln Arg Val Thr Leu Arg Cys Ser Pro Arg Ser Gly Asp
        35                  40                  45

Leu Ser Val Tyr Trp Tyr Gln Gln Ser Leu Asp Gln Gly Leu Gln Phe
    50                  55                  60

Leu Ile Gln Tyr Tyr Asn Gly Glu Glu Arg Ala Lys Gly Asn Ile Leu
65                  70                  75                  80

Glu Arg Phe Ser Ala Gln Gln Phe Pro Asp Leu His Ser Glu Leu Asn
                85                  90                  95

Leu Ser Ser Leu Glu Leu Gly Asp Ser Ala Leu Tyr Phe Cys Ala Ser
            100                 105                 110

Ser Val

<210> SEQ ID NO 10
<211> LENGTH: 273
<212> TYPE: PRT
<213> ORGANISM: artificial
<220> FEATURE:
<223> OTHER INFORMATION: TCR alpha chain (mmC), human modified

<400> SEQUENCE: 10

Met Leu Leu Glu His Leu Leu Ile Ile Leu Trp Met Gln Leu Thr Trp
1               5                   10                  15

Val Ser Gly Gln Gln Leu Asn Gln Ser Pro Gln Ser Met Phe Ile Gln
            20                  25                  30

Glu Gly Glu Asp Val Ser Met Asn Cys Thr Ser Ser Ser Ile Phe Asn
        35                  40                  45

Thr Trp Leu Trp Tyr Lys Gln Asp Pro Gly Glu Gly Pro Val Leu Leu
    50                  55                  60

Ile Ala Leu Tyr Lys Ala Gly Glu Leu Thr Ser Asn Gly Arg Leu Thr
65                  70                  75                  80

Ala Gln Phe Gly Ile Thr Arg Lys Asp Ser Phe Leu Asn Ile Ser Ala
                85                  90                  95

Ser Ile Pro Ser Asp Val Gly Ile Tyr Phe Cys Ala Gly Leu Ala Asp
            100                 105                 110

Tyr Gly Gly Ser Gln Gly Asn Leu Ile Phe Gly Lys Gly Thr Lys Leu
            115                 120                 125

Ser Val Lys Pro Asn Ile Gln Asn Pro Asp Pro Ala Val Tyr Gln Leu
        130                 135                 140

Arg Asp Ser Lys Ser Ser Asp Lys Ser Val Cys Leu Phe Thr Asp Phe
145                 150                 155                 160

Asp Ser Gln Thr Asn Val Ser Gln Ser Lys Asp Ser Asp Val Tyr Ile
                165                 170                 175
```

Thr Asp Lys Thr Val Leu Asp Met Arg Ser Met Asp Phe Lys Ser Asn
            180                 185                 190

Ser Ala Val Ala Trp Ser Asn Lys Ser Asp Phe Ala Cys Ala Asn Ala
            195                 200                 205

Phe Asn Asn Ser Ile Ile Pro Glu Asp Thr Phe Phe Pro Ser Ser Asp
    210                 215                 220

Val Pro Cys Asp Val Lys Leu Val Glu Lys Ser Phe Glu Thr Asp Thr
225                 230                 235                 240

Asn Leu Asn Phe Gln Asn Leu Ser Val Ile Gly Phe Arg Ile Leu Leu
            245                 250                 255

Leu Lys Val Ala Gly Phe Asn Leu Leu Met Thr Leu Arg Leu Trp Ser
            260                 265                 270

Ser

<210> SEQ ID NO 11
<211> LENGTH: 312
<212> TYPE: PRT
<213> ORGANISM: artificial
<220> FEATURE:
<223> OTHER INFORMATION: TCR beta chain mmC, human modified

<400> SEQUENCE: 11

Met Gly Phe Arg Leu Leu Cys Cys Val Ala Phe Cys Leu Leu Gly Ala
1               5                   10                  15

Gly Pro Val Asp Ser Gly Val Thr Gln Thr Pro Lys His Leu Ile Thr
            20                  25                  30

Ala Thr Gly Gln Arg Val Thr Leu Arg Cys Ser Pro Arg Ser Gly Asp
            35                  40                  45

Leu Ser Val Tyr Trp Tyr Gln Gln Ser Leu Asp Gln Gly Leu Gln Phe
    50                  55                  60

Leu Ile Gln Tyr Tyr Asn Gly Glu Glu Arg Ala Lys Gly Asn Ile Leu
65                  70                  75                  80

Glu Arg Phe Ser Ala Gln Gln Phe Pro Asp Leu His Ser Glu Leu Asn
            85                  90                  95

Leu Ser Ser Leu Glu Leu Gly Asp Ser Ala Leu Tyr Phe Cys Ala Ser
            100                 105                 110

Ser Val Trp Ala Ser Gly Gly Tyr Glu Gln Tyr Phe Gly Pro Gly Thr
            115                 120                 125

Arg Leu Thr Val Thr Glu Asp Leu Lys Asn Val Phe Pro Pro Glu Val
    130                 135                 140

Ala Val Phe Glu Pro Ser Lys Ala Glu Ile Ala His Thr Gln Lys Ala
145                 150                 155                 160

Thr Leu Val Cys Leu Ala Thr Gly Phe Tyr Pro Asp His Val Glu Leu
            165                 170                 175

Ser Trp Trp Val Asn Gly Lys Glu Val His Ser Gly Val Ser Thr Asp
            180                 185                 190

Pro Gln Pro Leu Lys Glu Gln Pro Ala Leu Asn Asp Ser Arg Tyr Cys
            195                 200                 205

Leu Ser Ser Arg Leu Arg Val Ser Ala Thr Phe Trp Gln Asn Pro Arg
    210                 215                 220

Asn His Phe Arg Cys Gln Val Gln Phe Tyr Gly Leu Ser Glu Asn Asp
225                 230                 235                 240

Glu Trp Thr Gln Asp Arg Ala Lys Pro Val Thr Gln Ile Val Ser Ala
            245                 250                 255

Glu Ala Trp Gly Arg Ala Asp Cys Gly Ile Thr Ser Arg Ser Tyr His
            260                 265                 270

Gln Gly Val Leu Ser Ala Thr Ile Leu Tyr Glu Ile Leu Leu Gly Lys
        275                 280                 285

Ala Thr Leu Tyr Ala Val Leu Val Ser Ala Leu Val Leu Met Ala Met
    290                 295                 300

Val Lys Arg Lys Asp Ser Arg Gly
305                 310

<210> SEQ ID NO 12
<211> LENGTH: 27
<212> TYPE: DNA
<213> ORGANISM: artificial
<220> FEATURE:
<223> OTHER INFORMATION: PRAME epitope, tumor associated antigen

<400> SEQUENCE: 12
agcctgctgc agcatctgat tggcctg                                        27

<210> SEQ ID NO 13
<211> LENGTH: 15
<212> TYPE: DNA
<213> ORGANISM: artificial
<220> FEATURE:
<223> OTHER INFORMATION: CDR1 alpha, human modified

<400> SEQUENCE: 13
agcatattta acacc                                                     15

<210> SEQ ID NO 14
<211> LENGTH: 15
<212> TYPE: DNA
<213> ORGANISM: artificial
<220> FEATURE:
<223> OTHER INFORMATION: CDR1 beta, human modified

<400> SEQUENCE: 14
tctggagacc tctct                                                     15

<210> SEQ ID NO 15
<211> LENGTH: 21
<212> TYPE: DNA
<213> ORGANISM: artificial
<220> FEATURE:
<223> OTHER INFORMATION: CDR2 alpha, human modified

<400> SEQUENCE: 15
ttatataagg ctggtgaatt g                                              21

<210> SEQ ID NO 16
<211> LENGTH: 18
<212> TYPE: DNA
<213> ORGANISM: artificial
<220> FEATURE:
<223> OTHER INFORMATION: CDR2 beta, human modified

<400> SEQUENCE: 16
tattataatg gagaagag                                                  18

<210> SEQ ID NO 17
<211> LENGTH: 48
<212> TYPE: DNA
<213> ORGANISM: artificial
<220> FEATURE:
<223> OTHER INFORMATION: CDR3 alpha, human modified

<400> SEQUENCE: 17
tgtgctgggc ttgctgatta tggaggaagc caaggaaatc tcatcttt                       48

<210> SEQ ID NO 18
<211> LENGTH: 45
<212> TYPE: DNA
<213> ORGANISM: artificial
<220> FEATURE:
<223> OTHER INFORMATION: CDR3 beta, human modified

<400> SEQUENCE: 18
tgtgccagca gcgtatgggc ctccggcggc tacgagcagt acttc                          45

<210> SEQ ID NO 19
<211> LENGTH: 324
<212> TYPE: DNA
<213> ORGANISM: artificial
<220> FEATURE:
<223> OTHER INFORMATION: TCR alpha variable region, human modified

<400> SEQUENCE: 19
atgctgctgg aacatctgct gatcatcctg tggatgcagc tgacctgggt ttccggccag          60
cagctgaatc agagccctca gagcatgttc atccaagaag gcgaggacgt ttccatgaat         120
tgcaccagca gcagcatctt caacacctgg ctgtggtaca gcaggaccc tggcgaagga          180 ccagtgctgc tgatcgcctt gtacaaagcc ggcgagctga ccagcaacgg cagactgaca         240
gcccagttcg gcattacccg gaaggacagc ttcctgaaca tctccgccag cattccctcc         300
gacgtgggca tctattttg tgcc                                                  324

<210> SEQ ID NO 20
<211> LENGTH: 342
<212> TYPE: DNA
<213> ORGANISM: artificial
<220> FEATURE:
<223> OTHER INFORMATION: TCR beta variable region, human modified

<400> SEQUENCE: 20
atgggcttca gactgctgtg ctgcgtggcc ttttgtctgc ttggagccgg acctgtggat          60
agcggcgtta cccagacacc taagcacctg atcacagcca caggccagcg cgtgaccctg         120
agatgttctc ctagaagcgg cgacctgagc gtgtactggt atcagcagtc tctgaccag          180 ggcctgcagt cctgatcca gtactacaac ggcgaggaaa agccaaggg caacatcctg           240 gaacggttca gcgcccagca gttcccagat ctgcacagcg agctgaacct gagcagcctg         300
gaactgggag atagcgccct gtacttctgt gcctctagcg tg                            342

<210> SEQ ID NO 21
<211> LENGTH: 819
<212> TYPE: DNA
<213> ORGANISM: artificial
<220> FEATURE:
<223> OTHER INFORMATION: TCR alpha chain (mmC), human modified

<400> SEQUENCE: 21
atgctgctgg aacatctgct gatcatcctg tggatgcagc tgacctgggt ttccggccag          60
cagctgaatc agagccctca gagcatgttc atccaagaag gcgaggacgt ttccatgaat         120
tgcaccagca gcagcatctt caacacctgg ctgtggtaca gcaggaccc tggcgaagga          180 ccagtgctgc tgatcgcctt gtacaaagcc ggcgagctga ccagcaacgg cagactgaca         240

```
gcccagttcg gcattacccg gaaggacagc ttcctgaaca tctccgccag cattccctcc        300
gacgtgggca tctattttgtg tgccggcctg gccgattacg gcggctctca gggaaatctg        360
atcttcggca agggcaccaa gctgagcgtg aagcccaaca ttcagaaccc cgatcctgcc        420
gtgtaccagc tgagagacag caagagcagc gacaagagcg tgtgcctgtt caccgacttc        480
gacagccaga ccaacgtgtc ccagagcaag gacagcgacg tgtacatcac cgacaagacc        540
gtgctggaca tgcggagcat ggacttcaag agcaacagcg ccgtggcctg gtccaacaag        600
agcgatttcg cctgcgccaa cgccttcaac aacagcatta tccccgagga cacattcttc        660
cccagctccg atgtgccctg cgacgtgaag ctggtggaaa agagcttcga cagacacacc        720
aacctgaact tccagaacct gtccgtgatc ggcttcagaa tcctgctgct gaaggtggcc        780
ggcttcaacc tgctgatgac actgagactg tggtccagc                             819
```

<210> SEQ ID NO 22
<211> LENGTH: 936
<212> TYPE: DNA
<213> ORGANISM: artificial
<220> FEATURE:
<223> OTHER INFORMATION: TCR beta chain (mmC), human modified

<400> SEQUENCE: 22

```
atgggcttca gactgctgtg ctgcgtggcc ttttgtctgc ttggagccgg acctgtggat         60
agcggcgtta cccagacacc taagcacctg atcacagcca caggccagcg cgtgaccctg        120
agatgttctc ctagaagcgg cgacctgagc gtgtactggt atcagcagtc tctggaccag        180
ggcctgcagt tcctgatcca gtactacaac ggcgaggaaa gagccaaggg caacatcctg        240
gaacggttca gcgcccagca gttcccagat ctgcacagcg agctgaacct gagcagcctg        300
gaactgggag atagcgccct gtacttctgt gcctctagcg tgtgggcctc tggcggctac        360
gagcagtatt ttggccctgg caccagactg accgtgaccg aggatctgaa gaacgtgttc        420
ccacctgagg tggccgtgtt cgagccttct aaggccgaga ttgcccacac acagaaagcc        480
acactcgtgt gtctggccac cggcttctat cccgatcacg tggaactgtc ttggtgggtc        540
aacggcaaag aggtgcacag cggcgtcagc acagatcccc agcctctgaa agaacagccc        600
gctctgaacg acagccggta ctgtctgagc agcagactga gagtgtccgc cacctctgg         660 cagaacccca gaaaccactt cagatgccag gtgcagttct acggcctgag cgagaacgat        720
gagtggaccc aggacagagc taagcccgtg acacagatcg tgtctgccga gcttggggc         780 agagccgatt gtggcatcac cagcagatct taccaccagg gcgtgctgag cgccaccatc        840
ctgtatgaga tcctgctggg caaagccact ctgtacgccg tgctggtgtc tgccctggtg        900
ctgatggcca tggtcaagcg gaaggatagc agaggc                                 936
```

<210> SEQ ID NO 23
<211> LENGTH: 13
<212> TYPE: PRT
<213> ORGANISM: artificial
<220> FEATURE:
<223> OTHER INFORMATION: 3825 CDR3 alpha, derived from mus musculus

<400> SEQUENCE: 23

```
Cys Ala Val Glu Pro Gly Gly Ser Tyr Ile Pro Thr Phe
1                 5                   10
```

<210> SEQ ID NO 24
<211> LENGTH: 13
<212> TYPE: PRT

-continued

```
<213> ORGANISM: artificial
<220> FEATURE:
<223> OTHER INFORMATION: 3825 CDR3 beta, derived from mus musculus

<400> SEQUENCE: 24

Cys Ala Ser Ser Pro Gly Leu Ser Tyr Glu Gln Tyr Phe
1               5               10

<210> SEQ ID NO 25
<211> LENGTH: 8
<212> TYPE: PRT
<213> ORGANISM: artificial
<220> FEATURE:
<223> OTHER INFORMATION: Irrelevant paptide, human

<400> SEQUENCE: 25

Gly Leu Ser Asn Thr His Val Leu
1               5

<210> SEQ ID NO 26
<211> LENGTH: 140
<212> TYPE: PRT
<213> ORGANISM: artificial
<220> FEATURE:
<223> OTHER INFORMATION: TCR alpha constant, derived from human

<400> SEQUENCE: 26

Ile Gln Asn Pro Asp Pro Ala Val Tyr Gln Leu Arg Asp Ser Lys Ser
1               5               10              15

Ser Asp Lys Ser Val Cys Leu Phe Thr Asp Phe Asp Ser Gln Thr Asn
            20              25              30

Val Ser Gln Ser Lys Asp Ser Asp Val Tyr Ile Thr Asp Lys Thr Val
        35              40              45

Leu Asp Met Arg Ser Met Asp Phe Lys Ser Asn Ser Ala Val Ala Trp
    50              55              60

Ser Asn Lys Ser Asp Phe Ala Cys Ala Asn Ala Phe Asn Asn Ser Ile
65              70              75              80

Ile Pro Glu Asp Thr Phe Phe Pro Ser Pro Glu Ser Ser Cys Asp Val
                85              90              95

Lys Leu Val Glu Lys Ser Phe Glu Thr Asp Thr Asn Leu Asn Phe Gln
            100             105             110

Asn Leu Ser Val Ile Gly Phe Arg Ile Leu Leu Leu Lys Val Ala Gly
        115             120             125

Phe Asn Leu Leu Met Thr Leu Arg Leu Trp Ser Ser
    130             135             140

<210> SEQ ID NO 27
<211> LENGTH: 177
<212> TYPE: PRT
<213> ORGANISM: artificial
<220> FEATURE:
<223> OTHER INFORMATION: TCR beta-01 constant, derived from human

<400> SEQUENCE: 27

Glu Asp Leu Asn Lys Val Phe Pro Pro Glu Val Ala Val Phe Glu Pro
1               5               10              15

Ser Glu Ala Glu Ile Ser His Thr Gln Lys Ala Thr Leu Val Cys Leu
            20              25              30

Ala Thr Gly Phe Phe Pro Asp His Val Glu Leu Ser Trp Trp Val Asn
        35              40              45

Gly Lys Glu Val His Ser Gly Val Ser Thr Asp Pro Gln Pro Leu Lys
```

-continued

```
         50                  55                  60

Glu Gln Pro Ala Leu Asn Asp Ser Arg Tyr Cys Leu Ser Ser Arg Leu
65                  70                  75                  80

Arg Val Ser Ala Thr Phe Trp Gln Asn Pro Arg Asn His Phe Arg Cys
                85                  90                  95

Gln Val Gln Phe Tyr Gly Leu Ser Glu Asn Asp Glu Trp Thr Gln Asp
                100                 105                 110

Arg Ala Lys Pro Val Thr Gln Ile Val Ser Ala Glu Ala Trp Gly Arg
            115                 120                 125

Ala Asp Cys Gly Phe Thr Ser Val Ser Tyr Gln Gln Gly Val Leu Ser
        130                 135                 140

Ala Thr Ile Leu Tyr Glu Ile Leu Leu Gly Lys Ala Thr Leu Tyr Ala
145                 150                 155                 160

Val Leu Val Ser Ala Leu Val Leu Met Ala Met Val Lys Arg Lys Asp
                165                 170                 175

Phe
```

<210> SEQ ID NO 28
<211> LENGTH: 179
<212> TYPE: PRT
<213> ORGANISM: artificial
<220> FEATURE:
<223> OTHER INFORMATION: TCR beta-02 constant, derived from human

<400> SEQUENCE: 28

```
Glu Asp Leu Lys Asn Val Phe Pro Pro Glu Val Ala Val Phe Glu Pro
1               5                   10                  15

Ser Glu Ala Glu Ile Ser His Thr Gln Lys Ala Thr Leu Val Cys Leu
                20                  25                  30

Ala Thr Gly Phe Tyr Pro Asp His Val Glu Leu Ser Trp Trp Val Asn
            35                  40                  45

Gly Lys Glu Val His Ser Gly Val Ser Thr Asp Pro Gln Pro Leu Lys
        50                  55                  60

Glu Gln Pro Ala Leu Asn Asp Ser Arg Tyr Cys Leu Ser Ser Arg Leu
65                  70                  75                  80

Arg Val Ser Ala Thr Phe Trp Gln Asn Pro Arg Asn His Phe Arg Cys
                85                  90                  95

Gln Val Gln Phe Tyr Gly Leu Ser Glu Asn Asp Glu Trp Thr Gln Asp
                100                 105                 110

Arg Ala Lys Pro Val Thr Gln Ile Val Ser Ala Glu Ala Trp Gly Arg
            115                 120                 125

Ala Asp Cys Gly Phe Thr Ser Glu Ser Tyr Gln Gln Gly Val Leu Ser
        130                 135                 140

Ala Thr Ile Leu Tyr Glu Ile Leu Leu Gly Lys Ala Thr Leu Tyr Ala
145                 150                 155                 160

Val Leu Val Ser Ala Leu Val Leu Met Ala Met Val Lys Arg Lys Asp
                165                 170                 175

Ser Arg Gly
```

<210> SEQ ID NO 29
<211> LENGTH: 140
<212> TYPE: PRT
<213> ORGANISM: artificial
<220> FEATURE:
<223> OTHER INFORMATION: TCR alpha constant, derived from mus musculus

<400> SEQUENCE: 29

-continued

```
Ile Gln Asn Pro Asp Pro Ala Val Tyr Gln Leu Arg Asp Ser Lys Ser
1               5                   10                  15

Ser Asp Lys Ser Val Cys Leu Phe Thr Asp Phe Asp Ser Gln Thr Asn
            20                  25                  30

Val Ser Gln Ser Lys Asp Ser Asp Val Tyr Ile Thr Asp Lys Thr Val
        35                  40                  45

Leu Asp Met Arg Ser Met Asp Phe Lys Ser Asn Ser Ala Val Ala Trp
    50                  55                  60

Ser Asn Lys Ser Asp Phe Ala Cys Ala Asn Ala Phe Asn Asn Ser Ile
65                  70                  75                  80

Ile Pro Glu Asp Thr Phe Phe Pro Ser Ser Asp Val Pro Cys Asp Val
                85                  90                  95

Lys Leu Val Glu Lys Ser Phe Glu Thr Asp Thr Asn Leu Asn Phe Gln
            100                 105                 110

Asn Leu Ser Val Ile Gly Phe Arg Ile Leu Leu Leu Lys Val Ala Gly
        115                 120                 125

Phe Asn Leu Leu Met Thr Leu Arg Leu Trp Ser Ser
    130                 135                 140
```

<210> SEQ ID NO 30
<211> LENGTH: 179
<212> TYPE: PRT
<213> ORGANISM: artificial
<220> FEATURE:
<223> OTHER INFORMATION: TCR beta constant, derived from mus musculus

<400> SEQUENCE: 30

```
Glu Asp Leu Lys Asn Val Phe Pro Pro Glu Val Ala Val Phe Glu Pro
1               5                   10                  15

Ser Lys Ala Glu Ile Ala His Thr Gln Lys Ala Thr Leu Val Cys Leu
            20                  25                  30

Ala Thr Gly Phe Tyr Pro Asp His Val Glu Leu Ser Trp Trp Val Asn
            35                  40                  45

Gly Lys Glu Val His Ser Gly Val Ser Thr Asp Pro Gln Pro Leu Lys
    50                  55                  60

Glu Gln Pro Ala Leu Asn Asp Ser Arg Tyr Cys Leu Ser Ser Arg Leu
65                  70                  75                  80

Arg Val Ser Ala Thr Phe Trp Gln Asn Pro Arg Asn His Phe Arg Cys
                85                  90                  95

Gln Val Gln Phe Tyr Gly Leu Ser Glu Asn Asp Glu Trp Thr Gln Asp
            100                 105                 110

Arg Ala Lys Pro Val Thr Gln Ile Val Ser Ala Glu Ala Trp Gly Arg
            115                 120                 125

Ala Asp Cys Gly Ile Thr Ser Arg Ser Tyr His Gln Gly Val Leu Ser
    130                 135                 140

Ala Thr Ile Leu Tyr Glu Ile Leu Leu Gly Lys Ala Thr Leu Tyr Ala
145                 150                 155                 160

Val Leu Val Ser Ala Leu Val Leu Met Ala Met Val Lys Arg Lys Asp
                165                 170                 175

Ser Arg Gly
```

<210> SEQ ID NO 31
<211> LENGTH: 136
<212> TYPE: PRT
<213> ORGANISM: artificial
<220> FEATURE:

<223> OTHER INFORMATION: TCR alpha murC constant, murinized

<400> SEQUENCE: 31

Ile Gln Asn Pro Glu Pro Ala Val Tyr Gln Leu Lys Asp Pro Arg Ser
1               5                   10                  15

Gln Asp Ser Thr Leu Cys Leu Phe Thr Asp Phe Asp Ser Gln Ile Asn
            20                  25                  30

Val Pro Lys Thr Met Glu Ser Gly Thr Phe Ile Thr Asp Lys Thr Val
            35                  40                  45

Leu Asp Met Lys Ala Met Asp Ser Lys Ser Asn Gly Ala Ile Ala Trp
        50                  55                  60

Ser Asn Gln Thr Ser Phe Thr Cys Gln Asp Ile Phe Lys Glu Thr Asn
65                  70                  75                  80

Ala Thr Tyr Pro Ser Ser Asp Val Pro Cys Asp Ala Thr Leu Thr Glu
                85                  90                  95

Lys Ser Phe Glu Thr Asp Met Asn Leu Asn Phe Gln Asn Leu Ser Val
            100                 105                 110

Met Gly Leu Arg Ile Leu Leu Leu Lys Val Ala Gly Phe Asn Leu Leu
            115                 120                 125

Met Thr Leu Arg Leu Trp Ser Ser
        130                 135

<210> SEQ ID NO 32
<211> LENGTH: 173
<212> TYPE: PRT
<213> ORGANISM: artificial
<220> FEATURE:
<223> OTHER INFORMATION: TCR beta murC constant, murinized

<400> SEQUENCE: 32

Glu Asp Leu Arg Asn Val Thr Pro Pro Lys Val Thr Leu Phe Glu Pro
1               5                   10                  15

Ser Lys Ala Glu Ile Ala Asn Lys Gln Lys Ala Thr Leu Val Cys Leu
            20                  25                  30

Ala Arg Gly Phe Phe Pro Asp His Val Glu Leu Ser Trp Trp Val Asn
        35                  40                  45

Gly Lys Glu Val His Ser Gly Val Ser Thr Asp Pro Gln Ala Tyr Lys
    50                  55                  60

Glu Ser Asn Tyr Ser Tyr Cys Leu Ser Ser Arg Leu Arg Val Ser Ala
65                  70                  75                  80

Thr Phe Trp His Asn Pro Arg Asn His Phe Arg Cys Gln Val Gln Phe
                85                  90                  95

His Gly Leu Ser Glu Glu Asp Lys Trp Pro Glu Gly Ser Pro Lys Pro
            100                 105                 110

Val Thr Gln Asn Ile Ser Ala Glu Ala Trp Gly Arg Ala Asp Cys Gly
            115                 120                 125

Ile Thr Ser Ala Ser Tyr His Gln Gly Val Leu Ser Ala Thr Ile Leu
        130                 135                 140

Tyr Glu Ile Leu Leu Gly Lys Ala Thr Leu Tyr Ala Val Leu Val Ser
145                 150                 155                 160

Gly Leu Val Leu Met Ala Met Val Lys Lys Lys Asn Ser
                165                 170

<210> SEQ ID NO 33
<211> LENGTH: 509
<212> TYPE: PRT
<213> ORGANISM: artificial

```
<220> FEATURE:
<223> OTHER INFORMATION: PRAME full-length, derived from human

<400> SEQUENCE: 33

Met Glu Arg Arg Arg Leu Trp Gly Ser Ile Gln Ser Arg Tyr Ile Ser
1               5                   10                  15

Met Ser Val Trp Thr Ser Pro Arg Arg Leu Val Glu Leu Ala Gly Gln
            20                  25                  30

Ser Leu Leu Lys Asp Glu Ala Leu Ala Ile Ala Ala Leu Glu Leu Leu
        35                  40                  45

Pro Arg Glu Leu Phe Pro Pro Leu Phe Met Ala Ala Phe Asp Gly Arg
    50                  55                  60

His Ser Gln Thr Leu Lys Ala Met Val Gln Ala Trp Pro Phe Thr Cys
65                  70                  75                  80

Leu Pro Leu Gly Val Leu Met Lys Gly Gln His Leu His Leu Glu Thr
                85                  90                  95

Phe Lys Ala Val Leu Asp Gly Leu Asp Val Leu Leu Ala Gln Glu Val
            100                 105                 110

Arg Pro Arg Arg Trp Lys Leu Gln Val Leu Asp Leu Arg Lys Asn Ser
            115                 120                 125

His Gln Asp Phe Trp Thr Val Trp Ser Gly Asn Arg Ala Ser Leu Tyr
        130                 135                 140

Ser Phe Pro Glu Pro Glu Ala Ala Gln Pro Met Thr Lys Lys Arg Lys
145                 150                 155                 160

Val Asp Gly Leu Ser Thr Glu Ala Glu Gln Pro Phe Ile Pro Val Glu
                165                 170                 175

Val Leu Val Asp Leu Phe Leu Lys Glu Gly Ala Cys Asp Glu Leu Phe
            180                 185                 190

Ser Tyr Leu Ile Glu Lys Val Lys Arg Lys Lys Asn Val Leu Arg Leu
        195                 200                 205

Cys Cys Lys Lys Leu Lys Ile Phe Ala Met Pro Met Gln Asp Ile Lys
    210                 215                 220

Met Ile Leu Lys Met Val Gln Leu Asp Ser Ile Glu Asp Leu Glu Val
225                 230                 235                 240

Thr Cys Thr Trp Lys Leu Pro Thr Leu Ala Lys Phe Ser Pro Tyr Leu
                245                 250                 255

Gly Gln Met Ile Asn Leu Arg Arg Leu Leu Leu Ser His Ile His Ala
            260                 265                 270

Ser Ser Tyr Ile Ser Pro Glu Lys Glu Glu Gln Tyr Ile Ala Gln Phe
        275                 280                 285

Thr Ser Gln Phe Leu Ser Leu Gln Cys Leu Gln Ala Leu Tyr Val Asp
    290                 295                 300

Ser Leu Phe Phe Leu Arg Gly Arg Leu Asp Gln Leu Leu Arg His Val
305                 310                 315                 320

Met Asn Pro Leu Glu Thr Leu Ser Ile Thr Asn Cys Arg Leu Ser Glu
                325                 330                 335

Gly Asp Val Met His Leu Ser Gln Ser Pro Ser Val Ser Gln Leu Ser
            340                 345                 350

Val Leu Ser Leu Ser Gly Val Met Leu Thr Asp Val Ser Pro Glu Pro
        355                 360                 365

Leu Gln Ala Leu Leu Glu Arg Ala Ser Ala Thr Leu Gln Asp Leu Val
    370                 375                 380

Phe Asp Glu Cys Gly Ile Thr Asp Asp Gln Leu Leu Ala Leu Leu Pro
385                 390                 395                 400
```

-continued

```
Ser Leu Ser His Cys Ser Gln Leu Thr Thr Leu Ser Phe Tyr Gly Asn
            405                 410                 415

Ser Ile Ser Ile Ser Ala Leu Gln Ser Leu Leu Gln His Leu Ile Gly
            420                 425                 430

Leu Ser Asn Leu Thr His Val Leu Tyr Pro Val Pro Leu Glu Ser Tyr
        435                 440                 445

Glu Asp Ile His Gly Thr Leu His Leu Glu Arg Leu Ala Tyr Leu His
    450                 455                 460

Ala Arg Leu Arg Glu Leu Leu Cys Glu Leu Gly Arg Pro Ser Met Val
465                 470                 475                 480

Trp Leu Ser Ala Asn Pro Cys Pro His Cys Gly Asp Arg Thr Phe Tyr
            485                 490                 495

Asp Pro Glu Pro Ile Leu Cys Pro Cys Phe Met Pro Asn
        500                 505
```